(12) United States Patent
Eng et al.

(10) Patent No.: US 7,670,775 B2
(45) Date of Patent: Mar. 2, 2010

(54) METHOD FOR DIFFERENTIATING MALIGNANT FROM BENIGN THYROID TISSUE

(75) Inventors: Charis Eng, Beachwood, OH (US); Frank Weber, Cleveland, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 216 days.

(21) Appl. No.: 11/675,375

(22) Filed: Feb. 15, 2007

(65) Prior Publication Data

US 2008/0274457 A1   Nov. 6, 2008

Related U.S. Application Data

(60) Provisional application No. 60/773,477, filed on Feb. 15, 2006.

(51) Int. Cl.
*C12Q 1/68* (2006.01)
*G01N 33/53* (2006.01)
*C07H 21/02* (2006.01)
*C07H 21/04* (2006.01)

(52) U.S. Cl. .......................... 435/6; 435/7.1; 536/23.1; 536/24.3

(58) Field of Classification Search .................. 435/6, 435/7.1; 536/23.1, 24.3
See application file for complete search history.

(56) References Cited

U.S. PATENT DOCUMENTS

2005/0053496 A1 *  3/2005  Danielsson et al. ..... 417/423.14
2008/0213805 A1 *  9/2008  Riggins et al. ............. 435/7.23

OTHER PUBLICATIONS

Aldred et al., Papillary and follicular thyroid carcinomas show distinctly different microarray expression profiles and can be distinguished by a minimum of five genes. Journal of Clinical Oncology 22(17) : 3531-3539 (2004).*
Aldred et al. Peroxisome proliferator-activated receptor gamma is frequently downregulated in a diversity of sporadic nonmedullary thyroid carcinomas. Oncogene 22(22) : 3412-6(2003).*
Eszlinger et al., Perspectives and limitations of microarray-based gene expression profiling of thyroid tumors. Endocrine Reviews 28(3) : 322-338 (2007).*
Huang et al;. Gene expression in papillary thyroid carcinoma reveals highly consistent profiles. PNAS 98(26) : 15044-15049 (2001).*
Umbricht et al., Human telomerase reverse transcriptase gene expression and the surgical management of suspicious thyroid tumors. Clinical Cancer Research 10(17) : 5762-5768(Sep. 2004).*
Weber et al. Genetic classification of benign and malignant thyroid follicular neoplasia based on a three-gene combination. Journal of Clinical Endocrinology & Metabolism 90(5) : 2512-2521 (2005).*

* cited by examiner

*Primary Examiner*—Ethan Whisenant
(74) *Attorney, Agent, or Firm*—Calfee, Halter & Griswold LLP

(57) ABSTRACT

Methods of identifying malignant thyroid tissue comprising testing a thyroid tissue sample for the expression of at least two genes chosen from CCND2, PCSK2, and PLAB. Kits for use in the disclosed methods are also provided.

8 Claims, 47 Drawing Sheets

CCND2 (cyclin D2)

mRNA sequence:
```
agagcgagca ggggagagcg agaccagttt taaggggagg accggtgcga gtgaggcagc cccgaggctc
tgctcgccca ccacccaatc ctcgcctccc ttctgctcca ccttctctct ctgccctcac ctctccccccg
aaaaccccct atttagccaa aggaaggagg tcaggggaac gctctcccct ccccttccaa aaaacaaaaa
cagaaaaacc cttttccagg ccggggaaag caggagggag aggggccgcc gggctggcca tggagctgct
gtgccacgag gtggacccgg tccgcagggc cgtgcgggac cgcaacctgc tccgagacga ccgcgtcctg
cagaacctgc tcaccatcga ggagcgctac cttccgcagt gctcctactt caagtgcgtg cagaaggaca
tccaacccta catgcgcaga atggtggcca cctggatgct ggaggtctgt gaggaacaga agtgcgaaga
agaggtcttc cctctggcca tgaattacct ggaccgtttc ttggctgggg tcccgactcc gaagtcccat
ctgcaactcc tgggtgctgt ctgcatgttc ctggcctcca aactcaaaga gaccagcccg ctgaccgcgg
agaagctgtg catttacacc gacaactcca tcaagcctca ggagctgctg gagtgggaac tggtggtgct
ggggaagttg aagtggaacc tggcagctgt cactcctcat gacttcattg agcacatctt gcgcaagctg
ccccagcagc gggagaagct gtctctgatc cgcaagcatg ctcagacctt cattgctctg tgtgccaccg
actttaagtt tgccatgtac ccaccgtcga tgatcgcaac tggaagtgtg ggagcagcca tctgtgggct
ccagcaggat gaggaagtga gctcgctcac ttgtgatgcc ctgactgagc tgctggctaa gatcaccaac
acagacgtgg attgtctcaa agcttgccag gagcagattg aggcggtgct cctcaatagc ctgcagcagt
accgtcagga ccaacgtgac ggatccaagt cggaggatga actggaccaa gccagcaccc tacagacgt
gcgggatatc gacctgtgag gatgccagtt gggccgaaag agagagacgc gtccataatc tggtctcttc
ttctttctgg ttgttttttgt tctttgtgtt ttagggtgaa acttaaaaaa aaaattctgc ccccacctag
atcatattta aagatctttt agaagtgaga gaaaaaggtc ctacgaaaac ggaataataa aaagcatttg
gtgcctattt gaagtacagc ataagggaat cccttgtata tgcgaacagt tattgtttga ttatgtaaaa
gtaatagtaa aatgcttaca ggaaaacctg cagagtagtt agagaatatg tatgcctgca atatgggaac
aaattagagg agacttttt ttttcatgtt atgagctagc acatacaccc ccttgtagta taatttcaag
gaactgtgta cgccatttat ggcatgatta gattgcaaag caatgaactc aagaaggaat tgaaataagg
agggacatga tggggaagga gtacaaaaca atctctcaac atgattgaac catttgggat ggagaagcac
ctttgctctc agccacctgt tactaagtca ggagtgtagt tggatctcta cattaatgtc ctcttgctgt
ctacagtagc tgctacctaa aaaagatgt tttattttgc cagttggaca caggtgattg gctcctgggt
ttcatgttct gtgacatcct gcttcttctt ccaaatgcag ttcattgcag acaccaccat attgctatct
aatggggaaa tgtagctatg gccataacc aaaactcaca tgaaacggag gcagatggag accaagggtg
ggatccagaa tggagtcttt tctgttattg tatttaaaag ggtaatgtgg ccttggcatt tcttcttaga
aaaaaactaa tttttggtgc tgattggcat gtctggttca cagtttagca ttgttataaa ccattccatt
cgaaaagcac tttgaaaaat tgttcccgag cgatagatgg gatggtttat gcaagtcatg ctgaatactc
ctccctctt ctcttttgcc ccctcccttc ctgcccccag tctgggttac tcttcgcttc tggtatctgg
cgttctttgg tacacagttc tggtgttcct accaggactc aagagacacc ccttcctgct gacattccca
tcacaacatt cctcagacaa gcctgtaaac taaaatctgt taccattctg atggcacaga aggatcttaa
ttcccatctc tatacttctc ctttggacat ggaaagaaaa gttattgctg gtgcaaagat agatggctga
acatcagggt gtggcatttt gttccctttt ccgtttttttt tttttttatt gttgttgtta attttattgc
aaagttgtat tcagcgtact tgaatttttc ttcctctcca cttcttagag gcattcagtt agcaaagagg
ttggagcaac aacttttttt ttttttttg cacaattgta attgacaggt aatgaagcta tttgttaaaa
tatttgcctt tttaagtaaa aaagaaaaat cagaacaggg ctatttgaag aattatttta tacacagatt
ctgccttgtt tcatagtatg agggttgaag acggaaaaca atctaagggt ctctcatttt tttaattttg
ttttgttcag tttggttttt tttttttttt gcgctgctaa gaagctaaag tcatccatcc ttattcacgt
tgacagtacc tagctgtaat gtttcacaga gtgtgctgct attttataaa catttttata atatattatt
ttactgctta aattccaagt cctgaagtag atggttgaga tatgagttct tcgtactgga aagcccttc
cgtagtttgt tttcttctgg tagcatattc atggttgttt tttttttct ttttggttt tttggttttt
ttttttcct ctgatcacat tcttcaaaga cggagtattc tttacctcag gtttactgga caaaatcaat
aactacaaaa ggcaatgatt cacgcttttg ttttcataat acctcacaac cgtacagttt ctgcttggga
gcccattcgc atgaggaata cagaagcagt gtgagcaggg ctgactccct ctcaggtgga aggcagggcg
gtctcactcc cagggacctt tttggtcatg gaggccatcg ggctcccagt tagaccctgg tatcctcatc
atgatggaaa aaatacattg aaccaaggga tcctcccctcc ccttcaaggc agacgttcag tacaaacatt
```

Figure 5

```
tatgcggtag gctcagatgt cgtaatttgc acttaggtac caggtgtcag gaaacagact aaaaagaatt
ccaccaggct gtttggagat cctcatcttg gagctttttc aaaagcgggg cttcatctgc aaagggccct
ttcatcttga agttttttccc ctccgtcttt cccctcccct ggcatggaca ccttgtgttt aggatcatct
ctgcaggttt cctaggtctg aatctgcgag tagatgaacc tgcagcaagc agcgtttatg gtgcttcctt
ctccctcctc tgtctcaaac tgcgcaggca agcactatgc aagcccaggc cctctgctga gcggtactaa
acggtcgggt tttcaatcac actgaattgg caggataaga aaaataggtc agataagtat gggatgatag
ttgaagggag gtgaagaggc tgcttctcta cagaggtgaa attccagatg agtcagtctc ttgggaagtg
tgtttagaag ggttcaggac tttgtgagtt agcatgaccc taaaattcta ggggatttct ggtgggacaa
tgggtggtga attttgaagt tttggagagg gaagtggagc agccagcaag taagctagcc agagttttct
caagagccag ctttgctcag cacactctcc tgggcccaa ggagtcccac ggaatgggga aagtgggaac
cctggagttc ttgggaatct tggagcctaa agagaaaccg aggtgcaaat tcatttcatg gtgactgacc
cttgagctta aacagaagca gcaaatgaaa gaaccggaca aataaggaag ggcacaagcc tacccgactc
tatttacagt ctgtaacttt ccactcttcc tgtagtcccg aggcccctgg gtccttctag cttttctctt
tcccatcctt ggggccttgt gtgatgatgg gtgtggggct gccgatggga aagtcggggg ttgttaggct
tttctgcctg ctcctgctta aacacaagaa ggaatcctgg attttgccct ctccttagct cttagtctct
ttggtaggag ttttgttcca gaggagctct ccccttgga tttgaacttg ctcttttgt tgttgttgtt
ctttctcttc ttttcttac ctcccactaa aggggttcca aattatcctg gtctttttct accttgttgt
gtttctatct cgtctttact tccatctgtt tgttttttc tccatcagtg ggggccgagt tgttccccca
gcctgccaaa ttttgatcct tcccctcttt tggccaaatc ctaggggaa gaaatcctag tatgccaaaa
atatatgcta agcataatta aactccatgc gggtccataa cagccaagaa gcctgcagga gaaagccaag
ggcagttccc tccgcagaac accccatgcg tgctgagagg cgagctcctt gaagaagggg ctgttcttcc
aggaggcctt attttgaact gcctcaggac cccactggag agcacagcat gccttactac tgggtcatcc
ttggtctatg tgctctgtac tggaggctct gttctgcctc ttatcagcca ggtcagggc acacatggct
taagtgacaa agccagagga gaagacaacc ctgacagcat cacgctgcat cccattgcta gcaggattgg
caactcttca gacggagctg cgcttccctg cagtctagca cctctagggc ctctccagac tgtgccctgg
gagctctggg actgaaaggt taagaacata aggcaggatc agatgactct ctccaagagg gcaggggaat
tttctctcca tgggccacag gggacagggc tgggagaaga aatagacttg caccttatgt catgtaaata
attgattttc tagttcaaga agataatatt ggtagtgtgg gaattggagg taggaagggg aggaagtctg
agtaagccag ttggcttcta agccaaaagg attcctcttt gtttatctct gagacagtcc aaccttgaga
atagctttaa aagggaaatt aatgctgaga tgataaagtc cccttaagcc aacaaaccct ctgtagctat
agaatgagtg caggtttcta ttggtgtgga ctcagagcaa tttacaagag ctgttcatgc agccatccat
ttgtgcaaaa tagggtaaga agattcaaga ggatatttat tacttcctca taccacatgg cttttgatga
ttctggattc taaacaaccc agaatggtca tttcaggcac aacgatacta cattcgtgtg tgtctgcttt
taaacttggc tgggctatca gaccctattc tcggctcagg ttttgagaag ccatcagcaa atgtgtacgt
gcatgctgta gctgcagcct gcatcccttc gcctgcagcc tactttgggg aaataaagtg ccttactgac
tgtagccatt acagtatcca atgtcttttg acaggtgcct gtccttgaaa aacaaagttt ctatttttat
ttttaattgg tttagttctt aactgctggc caactcttac atccccagca aatcatcggg ccattggatt
ttttccatta tgttcatcac ccttatatca tgtacctcag atctctctct ctctcctctc tctcagttat
atagtttctt gtcttggact ttttttttct tttcttttc tttttttttt tgctttaaaa caagtgtgat
gccatatcaa gtccatgtta ttctctcaca gtgtactcta taagaggtgt gggtgtctgt ttggtcagga
tgttagaaag tgctgataag tagcatgatc agtgtatgcg aaaaggtttt taggaagtat ggcaaaaatg
ttgtattggc tatgatggtg acatgatata gtcagctgcc ttttaagagg tcttatctgt tcagtgttaa
gtgatttaaa aaaataataa cctgttttct gactagttta aagatggatt tgaaaatggt tttgaatgca
attaggttat gctatttgga caataaactc accttgacct
```

Figure 5 continued

CCND2 (cyclin D2) (SEQ ID NO: 2)

Amino acid sequence:
```
MELLCHEVDP VRRAVRDRNL LRDDRVLQNL LTIEERYLPQ CSYFKCVQKD IQPYMRRMVA TWMLEVCEEQ
KCEEEVFPLA MNYLDRFLAG VPTPKSHLQL LGAVCMFLAS KLKETSPLTA EKLCIYTDNS IKPQELLEWE
LVVLGKLKWN LAAVTPHDFI EHILRKLPQQ REKLSLIRKH AQTFIALCAT DFKFAMYPPS MIATGSVGAA
ICGLQQDEEV SSLTCDALTE LLAKITNTDV DCLKACQEQI EAVLLNSLQQ YRQDQRDGSK SEDELDQAST
PTDVRDIDL
```

Figure 6

PCSK2 (proprotein convertase subtilisin/kexin type 2) (SEQ ID NO: 3)

mRNA sequence:
```
gagctgagga ggagctgaaa atgcagattt agcatcaagc acagacctac actcgctctt tctctccggt
acacacagct ccccacattc gcacccctgc ccgcgcgccg ggccgcctga ctgcacggct tcccctccag
ccagatgctg gagaacacac actgattcgc tgctttccaa gaccctgttc agtctctttc tctatacaaa
gattttttta aaaactatat ataagaattc tttatttgca ccctccctcc gagtcccctg ctccgccagc
ctgcgcgcct cctagcacca cttttcactc ccaaagaagg atgaagggtg gttgtgtctc ccagtggaag
gcggccgccg ggttcctctt ctgtgtcatg gtttttgcat ctgctgagcg accggtcttc acgaatcatt
ttcttgtgga gttgcataaa gggggagagg acaaagctcg ccaagttgca gcagaacacg gctttggagt
ccgaaagctt cccttttgctg aaggtctgta ccactttat cacaatggcc ttgcaaaggc aagagaaga
cgcagcctac accacaagca gcagctggag agaccccca gggtaaagat ggctttgcag caggaaggat
ttgaccgaaa aaagcgaggt tacagagaca tcaatgagat cgacatcaac atgaacgatc ctcttttttac
aaagcagtgg tatctgatca atactgggca agctgatggc actcctggcc ttgatttgaa tgtggctgaa
gcctgggagc tgggatacac agggaaaggt gttaccattg gaattatgga tgatgggatt gactatctcc
acccggacct ggcctccaac tataatgccg aagcaagtta cgacttcagc agcaacgacc ctatcctta
ccctcggtac acagatgact ggtttaacag ccacgggacc cgatgtgcag agaagtttc tgctgccgcc
aacaacaata tctgtggagt tggagtagca tacaactcca aggttgcagg catccggatg ctggaccagc
cattcatgac agacatcatc gaggcctcct ccatcagtca tatgccacag ctgattgaca ctacagcgc
cagctggggc cccacagaca acggcaagac agtggatggg ccccgggagc tcacgctgca ggccatgcc
gatggcgtga caagggccg cggcggcaaa ggcagcatct acgtgtgggc ctccggggac ggcggcagct
atgacgactg caactgcgac ggctacgcct ccagcatgtg gaccatctcc atcaactcag ccatcaacga
cggcaggact gcctgtacg acgagagctg ctcttccacc ttggcttcca ccttcagcaa cgggaggaaa
aggaaccccg aggccggtgt ggcaaccaca gatttgtacg gcaactgcac tctgaggcat ctgggacat
ctgcagctgc ccccgaggca gctggtgtgt ttgcactggc tctggaggct aacctgggtc tgacctggcg
ggacatgcag catctgactg tgctcacctc caaacggaac cagcttcacg acgaggtcca tcagtggcgg
cgcaatgggg tcggcctgga atttaatcac ctctttggct acggggtcct tgatgcaggt gccatggtga
aatggctaa agactggaaa accgtgcctg agagattcca ctgtgtggga ggctccgtgc aggaccctga
gaaaatacca tccactgca agttggtgct gacactcaca accgacgcct gtgaggggaa ggaaaatttt
gtccgctacc tggagcatgt ccaggctgtc atcacggtca acgcaaccag aagaggggag ctgaacatca
acatgacttc ccctatgggc accaagtcca ttttgctgag ccggcgtcca agggatgacg actccaaggt
gggctttgac aagtggcctt tcatgaccac tcacacgtgg ggggaagacg cccgaggcac ctggaccctg
gagctgggat tgtcggcag cgccccgcag aaggggggtgc tgaaggagtg gaccctgatg ctgcatggca
ctcagagtgc cccgtacatc gaccaggtgg tgcgggatta ccagtccaag ttggccatgt ccaagaaaga
ggagctggag gaagagctgg acgaagccgt ggagagaagc ctgaaaagca tccttaacaa gaactagcgc
tgcacatccg cctttcccac cgccctccct cccagctcc gcctctgtcc tcgctccacg tttcaggcag
gcacctagca attccatcac ccgtacaggc aattccgtct tcttaatctg aagcttcact cactgtcaat
gattatttc attacaatgg aaacaatctt ttttactcta tgccccaaat atagcgttcc caacaacatc
catgtcctat gtgtgactct aaattcttta tttctgtcat tcaaatgggt gatatcctga aaaaaaaaa
aaaaaaaaa ctgggacagc tttccctca tttttttttt tgtttctgag aaaagaacgt attttaaag
ccacatagag tgactccaag aacaattgtc catggtctca acaaggggc tgttacataa caagaaaatc
aaagctgagg acagggtgtg agcgccacat ctctgaaagc acaggagaca ctgtgctata atcctttgg
ggagcgatgt tttgaattta gtgagattta ccaggatgt agattaaggt gatgtgattc aaaagatgcc
attcatagag agccctagtt actgcatggg gaaagagatc caggaagcat gagtgctgga tattttacta
ccaatgccaa gataattcac tctactcagc cggcgtggca aatataaaac ttacagagcg tggctgtgct
ctcaccagct gctgctctga gttatgttaa aatccgctag agcagcccaa attttctca gtttgtatag
agttcatccc agccccaatt ttctggggct cctcacatag ctacccaaaa gagaaaaaaa attaagacaa
gcctggcaac acctggtg aagagtagtt tactagcttt tcaaacaaga atgtccctttt tcctaagtca
ctttgaggtg tctcaatctg atctgagtga gaggcgacag gagtatttt ttttttttac agctttacac
acacagatgt gggctttgat ttccaagtaa tataatggaa gagaaatctc atactccccc acagtttgat
gtcattaatg tgttgggaaa aaggcctctg tcccggaaga gtcatgggag gtgaaggggg cacgtttgaa
gatgcgagcg ctatcttcac atagttctcc agttgtatgg agcctcttct gccaagagag ggccatgcaa
ttcatcccag aggaacctga ggcctgaagg aggtgagaga agacctctgt gaggaaagca cacagtcacc
ttctcggcaa ctaagcagtc cctgagacca tttaacatgc aacccgaagg ttatggtcaa tcccaaaagt
```

Figure 7

```
caccactcca ttcccaacta gacattacca aagtgaccta cccagagatt gcttctcatc cccagtccca
atgcacatcc attcccaaga aatgctttgt cttcagcctc tccaggcacc atctcccttc ctgtgggagc
agagagctta gcctggagca cctttccttc aagccagcaa cacagagcac taggttcaat tccctgaagg
tggccacttt aagagagaaa tctgaaaacc ccatttgctt tcttttctcc catattggca tggatttctg
tcttctctaa caccttgtga ccttctctat atcatgcttt aaagtgtaat aatatgattt tttaaaagaa
atttattact tgttgcaaag gtcttttaa accagtttag atttcaagaa aaaataaatg gaaatcatcg
aaaattcatt tcacattaat ggtctaaaaa taaaccaaag gacattatgt gtgcatgtgt gtataagtgc
acacagaaat atatatacat atgtagacta tatacatgtg tgtatatatg tgtatatata catacacttg
tataaatgta tatacacata tacctataat gtgtgtatgt gtatttattg aagaaacaga taccatactc
atttctaaaa gaatattcag agaatatcaa gatgattctg gctgaaaaag gccagtggaa attcaggtga
aaatgttcat caattcccat tgcatcacct ctgtaatttt tcagctctct gtataaacat taaatgtctt
atatagcagc aaaaatataa aatagttgtc catattttca caggtgtggt gtaatttata aaattagaaa
gcaacttatc agctacttaa gagaaatggc aagttttgat atgagtatac aatatataaa aatatatata
gtgctatata tataaatatt tggtctctat ttcattttt gcatcagtat taatactaaa atatgtctcg
ctagtgatgt ttttatgata tccctgatcc taactgaaga gacagttatt tatagtcatt tattttaaaa
aatgaaaata agtgaataat aattaggtta acattgttgc tccctgtgac aaaattttat aagcaaattt
caaaagacat gttgtaaatt aggaggctca acaataaaac attatgctcc agaaa
```

Figure 7 continued

PCSK2 (proprotein convertase subtilisin/kexin type 2) (SEQ ID NO: 4)

Amino acid sequence:
```
MKGGCVSQWK AAAGFLFCVM VFASAERPVF TNHFLVELHK GGEDKARQVA AEHGFGVRKL PFAEGLYHFY
HNGLAKAKRR RSLHHKQQLE RDPRVKMALQ QEGFDRKKRG YRDINEIDIN MNDPLFTKQW YLINTGQADG
TPGLDLNVAE AWELGYTGKG VTIGIMDDGI DYLHPDLASN YNAEASYDFS SNDPYPYPRY TDDWFNSHGT
RCAGEVSAAA NNNICGVGVA YNSKVAGIRM LDQPFMTDII EASSISHMPQ LIDIYSASWG PTDNGKTVDG
PRELTLQAMA DGVNKGRGGK GSIYVWASGD GGSYDDCNCD GYASSMWTIS INSAINDGRT ALYDESCSST
LASTFSNGRK RNPEAGVATT DLYGNCTLRH SGTSAAAPEA AGVFALALEA NLGLTWRDMQ HLTVLTSKRN
QLHDEVHQWR RNGVGLEFNH LFGYGVLDAG AMVKMAKDWK TVPERFHCVG GSVQDPEKIP STGKLVLTLT
TDACEGKENF VRYLEHVQAV ITVNATRRGD LNINMTSPMG TKSILLSRRP RDDDSKVGFD KWPFMTTHTW
GEDARGTWTL ELGFVGSAPQ KGVLKEWTLM LHGTQSAPYI DQVVRDYQSK LAMSKKEELE EELDEAVERS
LKSILNKN
```

Figure 8

PLAB (SEQ ID NO: 5)

mRNA sequence:
```
cggaacgagg gcaacctgca cagccatgcc cgggcaagaa ctcaggacgg tgaatggctc tcagatgctc
ctggtgttgc tggtgctctc gtggctgccg catggggggcg ccctgtctct ggccgaggcg agccgcgcaa
gtttcccggg accctcagag ttgcactccg aagactccag attccgagag ttgcggaaac gctacgagga
cctgctaacc aggctgcggg ccaaccagag ctgggaagat tcgaacaccg acctcgtccc ggcccctgca
gtccggatac tcacgccaga agtgcggctg ggatccggcg gccacctgca cctgcgtatc tctcgggccg
cccttcccga ggggctcccc gaggcctccc gccttcaccg ggctctgttc cggctgtccc cgacggcgtc
aaggtcgtgg gacgtgacac gaccgctgcg gcgtcagctc agccttgcaa gaccccaagc gcccgcgctg
cacctgcgac tgtcgccgcc gccgtcgcag tcggaccaac tgctggcaga atcttcgtcc gcacggcccc
agctggagtt gcacttgcgg ccgcaagccg ccaggggggcg ccgcagagcg cgtgcgcgca acggggacga
ctgtccgctc gggcccgggc gttgctgccg tctgcacacg gtccgcgcgt cgctggaaga cctgggctgg
gccgattggg tgctgtcgcc acgggaggtg caagtgacca tgtgcatcgg cgcgtgcccg agccagttcc
gggcggcaaa catgcacgcg cagatcaaga cgagcctgca ccgcctgaag cccgacacgg agccagcgcc
ctgctgcgtg cccgccagct acaatcccat ggtgctcatt caaaagaccg acaccggggt gtcgctccag
acctatgatg acttgttagc caaagactgc cactgcatat gagcagtcct ggtccttcca ctgtgcacct
gcgcggggga ggcgacctca gttgtcctgc cctgtggaat gggctcaagg ttcctgagac acccgattcc
tgcccaaaca gctgtattta taagtctg ttatttatta ttaatttatt ggggtgacct tcttggggac
tcggggctg gtctgatgga actgtgtatt tatttaaaac tctggtgata aaataaagc tgtctgaact
gttaaaaaaa aaaa
```

Figure 9

PLAB (SEQ ID NO: 6)

Amino acid sequence:
```
MPGQELRTVN GSQMLLVLLV LSWLPHGGAL SLAEASRASF PGPSELHSED SRFRELRKRY EDLLTRLRAN
QSWEDSNTDL VPAPAVRILT PEVRLGSGGH LHLRISRAAL PEGLPEASRL HRALFRLSPT ASRSWDVTRP
LRRQLSLARP QAPALHLRLS PPPSQSDQLL AESSSARPQL ELHLRPQAAR GRRRARARNG DDCPLGPGRC
CRLHTVRASL EDLGWADWVL SPREVQVTMC IGACPSQFRA ANMHAQIKTS LHRLKPDTEP APCCVPASYN
PMVLIQKTDT GVSLQTYDDL LAKDCHCI
```

Figure 10 hTERT (human telomerase reverse transcriptase) (SEQ ID NO: 7)

mRNA sequence of variant #1:
```
gcagcgctgc gtcctgctgc gcacgtggga agccctggcc ccggccaccc ccgcgatgcc gcgcgctccc
cgctgccgag ccgtgcgctc cctgctgcgc agccactacc gcgaggtgct gccgctggcc acgttcgtgc
ggcgcctggg gccccagggc tggcggctgg tgcagcgcgg ggacccggcg gctttccgcg cgctggtggc
ccagtgcctg gtgtgcgtgc cctgggacgc acggccgccc cccgccgccc cctccttccg ccaggtgtcc
tgcctgaagg agctggttgc ccgagtgctg cagaggctgt gcgagcgcgg cgcgaagaac gtgctggcct
tcggcttcgc gctgctggac ggggcccgcg ggggccccc cgaggccttc accaccagcg tgcgcagcta
cctgcccaac acggtgaccg acgcactgcg ggggagcggg gcgtggggc tgctgctgcg ccgcgtgggc
gacgacgtgc tggttcacct gctggcacgc tgcgcgctct ttgtgctggt ggctcccagc tgcgcctacc
aggtgtgcgg gccgccgctg taccagctcg gcgctgccac tcaggcccgg ccccgccac acgctagtgg
accccgaagg cgtctgggat gcgaacgggc ctggaaccat agcgtcaggg aggccgggt ccccctgggc
ctgccagccc cgggtgcgag gaggcgcggg ggcagtgcca gccgaagtct gccgttgccc aagaggccca
ggcgtggcgc tgccctgag ccggagcgga cgcccgttgg gcaggggtcc tgggcccacc cgggcaggac
gcgtggaccg agtgaccgtg gtttctgtgt ggtgtcacct gccagacccg ccgaagaagc cacctctttg
gagggtgcgc tctctggcac gcgccactcc cacccatccg tgggccgcca gcaccacgcg ggccccccat
ccacatcgcg gccaccacgt ccctgggaca cgccttgtcc cccggtgtac gccgagacca agcacttcct
ctactcctca ggcgacaagg agcagctgcg gccctccttc ctactcagct ctctgaggcc cagcctgact
ggcgctcgga ggctcgtgga gaccatcttt ctgggttcca ggccctggat gccagggact ccccgcaggt
tgccccgcct gccccagcgc tactggcaaa tgcggcccct gtttctggag ctgcttggga accacgcgca
gtgcccctac ggggtgctcc tcaagacgca ctgccgctg cgagctgcgg tcaccccagc agccggtgtc
tgtgcccggg agaagcccca gggctctgtg gcggcccccg aggaggagga cacagacccc cgtcgcctgg
tgcagctgct ccgccagcac agcagcccct ggcaggtgta cggcttcgtg cgggcctgcc tgcgccggct
ggtgccccca ggcctctggg gctccaggca caacgaacgc cgcttcctca ggaacaccaa gaagttcatc
tccctgggga agcatgccaa gctctcgctg caggagctga cgtggaagat gagcgtgcgg gactgcgctt
ggctgcgcag gagcccaggg gttggctgtg ttccggccgc agagcaccgt ctgcgtgagg agatcctggc
caagttcctg cactggctga tgagtgtgta cgtcgtcgag ctgctcaggt cttcttttta tgtcacggag
accacgtttc aaaagaacag gctctttttc taccggaaga gtgtctggag caagttgcaa agcattggaa
tcagacagca cttgaagagg gtgcagctgc gggagctgtc ggaagcagag gtcaggcagc atcgggaagc
caggcccgcc ctgctgacgt ccagactccg cttcatcccc aagcctgacg gctgcggcc gattgtgaac
atggactacg tcgtgggagc cagaacgttc gcagagaaa agagggccga gcgtctcacc tcgagggtga
aggcactgtt cagcgtgctc aactacgagc gggcgcggcg ccccggcctc ctgggcgcct ctgtgctggg
cctggacgat atccacaggg cctggcgcac cttcgtgctg cgtgtgcggg cccaggaccc gccgcctgag
ctgtactttg tcaaggtgga tgtgacgggc gcgtacgaca ccatcccca ggacaggctc acggaggtca
tcgccagcat catcaaaccc cagaacacgt actgcgtgcg tcggtatgcc gtggtccaga aggccgccca
tgggcacgtc cgcaaggcct tcaagagcca cgtctctacc ttgacagacc tccagccgta catgcgacag
ttcgtggctc acctgcagga ccagccccg ctgagggatg ccgtcgtcat cgagcagagc tcctcctga
atgaggccag cagtggcctc ttcgacgtct tcctacgctt catgtgccac cacgccgtgc gcatcagggg
caagtcctac gtccagtgcc aggggatccc gcaggctcc atcctctcca cgctgctctg cagcctgtgc
tacggcgaca tggagaacaa gctgtttgcg gggattcggc gggacgggct gctcctgcgt ttggtggatg
atttccttgtt ggtgacacct cacctcaccc acgcgaaaac cttcctcagg accctggtcc gaggtgtccc
tgagtatggc tgcgtggtga acttgcggaa gacagtggtg aacttccctg tagaagacga ggcctgggt
ggcacggctt ttgttcagat gccggccac ggcctattcc cctggtgcgg cctgctgctg gatacccgga
ccctggaggt gcagagcgac tactccagct atgcccggac tccatcaga gccagtctca ccttcaaccg
cggcttcaag gctgggagga catgcgtcg caaactcttt ggggtcttgc ggctgaagtg tcacagcctg
tttctggatt tgcaggtgaa cagcctccag acggtgtgca ccaacatcta caagatcctc ctgctgcagg
cgtacaggtt tcacgcatgt gtgctgcagc tcccatttca tcagcaagtt tggaagaacc ccacatttttt
cctgcgcgtc atctctgaca cggcctccct ctgctactcc atcctgaaag ccaagaacgc agggatgtcg
```

Figure 11

```
ctggggcca aggcgccgc cggccctctg ccctccgagg ccgtgcagtg gctgtgccac caagcattcc
tgctcaagct gactcgacac cgtgtcacct acgtgccact cctggggtca ctcaggacag cccagacgca
gctgagtcgg aagctcccgg ggacgacgct gactgccctg gaggccgcag ccaacccggc actgccctca
gacttcaaga ccatcctgga ctgatggcca cccgcccaca gccaggccga gagcagacac cagcagccct
gtcacgccgg gctctacgtc cagggaggg aggggcggcc cacacccagg cccgcaccgc tgggagtctg
aggcctgagt gagtgtttgg ccgaggcctg catgtccggc tgaaggctga gtgtccggct gaggcctgag
cgagtgtcca gccaagggct gagtgtccag cacacctgcc gtcttcactt ccccacaggc tggcgctcgg
ctccacccca gggccagctt ttcctcacca ggagcccggc ttccactccc cataggaa tagtccatcc
ccagattcgc cattgttcac ccctcgccct gccctccttt gccttccacc ccaccatcc aggtggagac
cctgagaagg accctgggag ctctgggaat ttggagtgac caaaggtgtg ccctgtacac aggcgaggac
cctgcacctg gatggggtc cctgtgggtc aaattggggg gaggtgctgt gggagtaaaa tactgaatat
atgagttttt cagttttgaa aaaaa
```

Figure 11 continued hTERT (human telomerase reverse transcriptase) (SEQ ID NO: 8)

Amino acid sequence of isoform 1:
```
MPRAPRCRAV RSLLRSHYRE VLPLATFVRR LGPQGWRLVQ RGDPAAFRAL VAQCLVCVPW DARPPPAAPS
FRQVSCLKEL VARVLQRLCE RGAKNVLAFG FALLDGARGG PPEAFTTSVR SYLPNTVTDA LRGSGAWGLL
LRRVGDDVLV HLLARCALFV LVAPSCAYQV CGPPLYQLGA ATQARPPPHA SGPRRRLGCE RAWNHSVREA
GVPLGLPAPG ARRRGGSASR SLPLPKRPRR GAAPEPERTP VGQGSWAHPG RTRGPSDRGF CVVSPARPAE
EATSLEGALS GTRHSHPSVG RQHHAGPPST SRPPRPWDTP CPPVYAETKH FLYSSGDKEQ LRPSFLLSSL
RPSLTGARRL VETIFLGSRP WMPGTPRRLP RLPQRYWQMR PLFLELLGNH AQCPYGVLLK THCPLRAAVT
PAAGVCAREK PQGSVAAPEE EDTDPRRLVQ LLRQHSSPWQ VYGFVRACLR RLVPPGLWGS RHNERRFLRN
TKKFISLGKH AKLSLQELTW KMSVRDCAWL RRSPGVGCVP AAEHRLREEI LAKFLHWLMS VYVVELLRSF
FYVTETTFQK NRLFFYRKSV WSKLQSIGIR QHLKRVQLRE LSEAEVRQHR EARPALLTSR LRFIPKPDGL
RPIVNMDYVV GARTFRREKR AERLTSRVKA LFSVLNYERA RRPGLLGASV LGLDDIHRAW RTFVLRVRAQ
DPPPELYFVK VDVTGAYDTI PQDRLTEVIA SIIKPQNTYC VRRYAVVQKA AHGHVRKAFK SHVSTLTDLQ
PYMRQFVAHL QETSPLRDAV VIEQSSSLNE ASSGLFDVFL RFMCHHAVRI RGKSYVQCQG IPQGSILSTL
LCSLCYGDME NKLFAGIRRD GLLLRLVDDF LLVTPHLTHA KTFLRTLVRG VPEYGCVVNL RKTVVNFPVE
DEALGGTAFV QMPAHGLFPW CGLLLDTRTL EVQSDYSSYA RTSIRASLTF NRGFKAGRNM RRKLFGVLRL
KCHSLFLDLQ VNSLQTVCTN IYKILLLQAY RFHACVLQLP FHQQVWKNPT FFLRVISDTA SLCYSILKAK
NAGMSLGAKG AAGPLPSEAV QWLCHQAFLL KLTRHRVTYV PLLGSLRTAQ TQLSRKLPGT TLTALEAAAN
PALPSDFKTI LD
```

Figure 12 hTERT (human telomerase reverse transcriptase) (SEQ ID NO: 9)

mRNA sequence of variant #2:

```
gcagcgctgc gtcctgctgc gcacgtggga agccctggcc ccggccaccc ccgcgatgcc gcgcgctccc
cgctgccgag ccgtgcgctc cctgctgcgc agccactacc gcgaggtgct gccgctggcc acgttcgtgc
ggcgcctggg gccccagggc tggcggctgg tgcagcgcgg ggacccggcg gctttccgcg cgctggtggc
ccagtgcctg gtgtgcgtgc cctgggacgc acggccgccc ccgccgccc cctccttccg ccaggtgtcc
tgcctgaagg agctggtggc ccgagtgctg cagaggctgt gcgagcgcgg cgcgaagaac gtgctggcct
tcggcttcgc gctgctggac ggggcccgcg ggggccccc cgaggccttc accaccagcg tgcgcagcta
cctgcccaac acggtgaccg acgcactgcg ggggagcggg gcgtggggc tgctgctgcg ccgcgtgggc
gacgacgtgc tggttcacct gctggcacgc tgcgcgctct ttgtgctggt ggctcccagc tgcgcctacc
aggtgtgcgg gccgccgctg taccagctcg gcgctgccac tcaggcccgg ccccgccac acgctagtgg
accccgaagg cgtctgggat gcgaacgggc tggaaccat agcgtcaggg aggccgggt ccccctgggc
ctgccagccc cgggtgcgag gaggcgcggg ggcagtgcca gccgaagtct gccgttgccc aagaggccca
ggcgtggcgc tgcccctgag ccggagcgga cgcccgttgg gcaggggtcc tgggcccacc cgggcaggac
gcgtggaccg agtgaccgtg gtttctgtgt ggtgtcacct gccagacccg ccgaagaagc cacctctttg
gagggtgcgc tctctggcac gcgccactcc cacccatccg tgggccgcca gcaccacgcg ggccccccat
ccacatcgcg gccaccacgt ccctgggaca cgccttgtcc cccgtgtac gccgagacca agcacttcct
ctactcctca ggcgacaagg agcagctgcg gccctccttc ctactcagct ctctgaggcc cagcctgact
ggcgctcgga ggctcgtgga gaccatcttt ctgggttcca ggccctggat gccagggact ccccgcaggt
tgccccgcct gccccagcgc tactggcaaa tgcggccccct gtttctggag ctgcttggga accacgcgca
gtgcccctac ggggtgctcc tcaagacgca ctgccgctg cgagctgcgg tcaccccagc agccggtgtc
tgtgcccggg agaagcccca gggctctgtg gcggccccg aggaggagga cacagacccc cgtcgcctgg
tgcagctgct ccgccagcac agcagcccct ggcaggtgta cggcttcgtg cgggcctgcc tgcgccggct
ggtgccccca ggcctctggg gctccaggca caacgaacgc cgcttcctca ggaacaccaa gaagttcatc
tccctgggga agcatgccaa gctctcgctg caggagctga cgtggaagat gagcgtgcgg gactgcgctt
ggctgcgcag gagcccaggg gttggctgtg ttccggccgc agagcaccgt ctgcgtgagg agatcctggc
caagttcctg cactggctga tgagtgtgta cgtcgtcgag ctgctcaggt cttctcttta tgtcacggag
accacgtttc aaaagaacag gctctttttc taccggaaga gtgtctggag caagttgcaa agcattggaa
tcagacagca cttgaagagg gtgcagctgc gggagctgtc ggaagcagag gtcaggcagc atcgggaagc
caggcccgcc ctgctgacgt ccagactccg cttcatcccc aagcctgacg gctgcggcc gattgtgaac
atggactacg tcgtgggagc cagaacgttc cgcagagaaa agagggccga gcgtctcacc tcgagggtga
aggcactgtt cagcgtgctc aactacgagc gggcgcggcg ccccggcctc ctgggcgcct ctgtgctggg
cctggacgat atccacaggg cctggcgcac cttcgtgctg cgtgtgcggg cccaggaccc gccgcctgag
ctgtactttg tcaaggacag gctcacggag gtcatcgcca gcatcatcaa ccccagaac acgtactgcg
tgcgtcggta tgccgtggtc cagaaggccg cccatgggca cgtccgcaag gccttcaaga gccacgtctc
taccttgaca gacctccagc cgtacatgcg acagttcgtg gctcacctgc aggagaccag cccgctgagg
gatgccgtcg tcatcgagca gagctcctcc ctgaatgagg ccagcagtgg cctcttcgac gtcttcctac
gcttcatgtg ccaccacgcc gtgcgcatca ggggcaagtc ctacgtccag tgccaggga tcccgcaggg
ctccatcctc tccacgctgc tctgcagcct gtgctacggc gacatggaga caagctgtt tgcgggatt
cggcgggacg ggctgctcct gcgtttggtg gatgatttct tgttggtgac acctcacctc acccacgcga
aaaccttcct caggaccctg gtccgaggtg tccctgagta tggctgcgtg gtgaacttgc ggaagacagt
ggtgaacttc cctgtagaag acgaggccct gggtggcacg gcttttgttc agatgccggc ccacggccta
ttccctggt gcggcctgct gctggatacc cggaccctgg aggtgcagag cgactactcc agctatgccc
ggacctccat cagagccagt ctcaccttca accgcggctt caaggctggg aggaacatgc gtcgcaaact
ctttgggtc ttgcggctga gtgtcacag cctgtttctg gatttgcagg tgaacagcct ccagacggtg
tgcaccaaca tctacaagat cctcctgctg caggcgtaca ggtttcacgc atgtgtgctg cagctcccat
```

Figure 13

```
ttcatcagca agtttggaag aaccccacat ttttcctgcg cgtcatctct gacacggcct ccctctgcta
ctccatcctg aaagccaaga acgcagggat gtcgctgggg gccaagggcg ccgccggccc tctgccctcc
gaggccgtgc agtggctgtg ccaccaagca ttcctgctca agctgactcg acaccgtgtc acctacgtgc
cactcctggg gtcactcagg acagcccaga cgcagctgag tcggaagctc ccggggacga cgctgactgc
cctggaggcc gcagccaacc cggcactgcc ctcagacttc aagaccatcc tggactgatg gccacccgcc
cacagccagg ccgagagcag acaccagcag ccctgtcacg ccgggctcta cgtcccaggg agggaggggc
ggcccacacc caggcccgca ccgctgggag tctgaggcct gagtgagtgt ttggccgagg cctgcatgtc
cggctgaagg ctgagtgtcc ggctgaggcc tgagcgagtg tccagccaag ggctgagtgt ccagcacacc
tgccgtcttc acttccccac aggctggcgc tcggctccac cccagggcca gcttttcctc accaggagcc
cggcttccac tccccacata ggaatagtcc atcccagat cgccattgt tcaccctcg ccctgccctc
ctttgccttc caccccacc atccaggtgg agacctgag aaggaccctg ggagctctgg gaatttggag
tgaccaaagg tgtgccctgt acacaggcga ggaccctgca cctggatggg ggtccctgtg ggtcaaattg
ggggaggtg ctgtgggagt aaaatactga atatatgagt ttttcagttt tgaaaaaaa
```

Figure 13 continued hTERT (human telomerase reverse transcriptase) (SEQ ID NO: 10)

Amino acid sequence of isoform 2:

```
MPRAPRCRAV RSLLRSHYRE VLPLATFVRR LGPQGWRLVQ RGDPAAFRAL VAQCLVCVPW DARPPPAAPS
FRQVSCLKEL VARVLQRLCE RGAKNVLAFG FALLDGARGG PPEAFTTSVR SYLPNTVTDA LRGSGAWGLL
LRRVGDDVLV HLLARCALFV LVAPSCAYQV CGPPLYQLGA ATQARPPPHA SGPRRRLGCE RAWNHSVREA
GVPLGLPAPG ARRRGGSASR SLPLPKRPRR GAAPEPERTP VGQGSWAHPG RTRGPSDRGF CVVSPARPAE
EATSLEGALS GTRHSHPSVG RQHHAGPPST SRPPRPWDTP CPPVYAETKH FLYSSGDKEQ LRPSFLLSSL
RPSLTGARRL VETIFLGSRP WMPGTPRRLP RLPQRYWQMR PLFLELLGNH AQCPYGVLLK THCPLRAAVT
PAAGVCAREK PQGSVAAPEE EDTDPRRLVQ LLRQHSSPWQ VYGFVRACLR RLVPPGLWGS RHNERRFLRN
TKKFISLGKH AKLSLQELTW KMSVRDCAWL RRSPGVGCVP AAEHRLREEI LAKFLHWLMS VYVVELLRSF
FYVTETTFQK NRLFFYRKSV WSKLQSIGIR QHLKRVQLRE LSEAEVRQHR EARPALLTSR LRFIPKPDGL
RPIVNMDYVV GARTFRREKR AERLTSRVKA LFSVLNYERA RRPGLLGASV LGLDDIHRAW RTFVLRVRAQ
DPPPELYFVK DRLTEVIASI IKPQNTYCVR RYAVVQKAAH GHVRKAFKSH VSTLTDLQPY MRQFVAHLQE
TSPLRDAVVI EQSSSLNEAS SGLFDVFLRF MCHHAVRIRG KSYVQCQGIP QGSILSTLLC SLCYGDMENK
LFAGIRRDGL LLRLVDDFLL VTPHLTHAKT FLRTLVRGVP EYGCVVNLRK TVVNFPVEDE ALGGTAFVQM
PAHGLFPWCG LLLDTRTLEV QSDYSSYART SIRASLTFNR GFKAGRNMRR KLFGVLRLKC HSLFLDLQVN
SLQTVCTNIY KILLLQAYRF HACVLQLPFH QQVWKNPTFF LRVISDTASL CYSILKAKNA GMSLGAKGAA
GPLPSEAVQW LCHQAFLLKL TRHRVTYVPL LGSLRTAQTQ LSRKLPGTTL TALEAAANPA LPSDFKTILD
```

Figure 14 hTERT (human telomerase reverse transcriptase) (SEQ ID NO: 11)

mRNA sequence of variant #3:
```
gcagcgctgc gtcctgctgc gcacgtggga agccctggcc ccggccaccc ccgcgatgcc gcgcgctccc
cgctgccgag ccgtgcgctc cctgctgcgc agccactacc gcgaggtgct gccgctggcc acgttcgtgc
ggcgcctggg gccccagggc tggcggctgg tgcagcgcgg ggacccggcg gctttccgcg cgctggtggc
ccagtgcctg gtgtgcgtgc cctgggacgc acggccgccc ccgcgcgccc cctccttccg ccaggtgtcc
tgcctgaagg agctggtggc ccgagtgctg cagaggctgt gcgagcgcgg cgcgaagaac gtgctggcct
tcggcttcgc gctgctggac ggggcccgcg ggggcccccc cgaggccttc accaccagcg tgcgcagcta
cctgcccaac acggtgaccg acgcactgcg ggggagcggg gcgtggggc tgctgctgcg ccgcgtgggc
gacgacgtgc tggttcacct gctggcacgc tgcgcgctct ttgtgctggt ggctcccagc tgcgcctacc
aggtgtgcgg gccgccgctg taccagctcg gcgctgccac tcaggcccgg ccccgccac acgctagtgg
accccgaagg cgtctgggat gcgaacgggc ctggaaccat agcgtcaggg aggccggggt cccctgggc
ctgccagccc cgggtgcgag gaggcgcggg ggcagtgcca gccgaagtct gccgttgccc aagaggccca
ggcgtggcgc tgcccctgag ccggagcgga cgccgttgg gcaggggtcc tgggcccacc cgggcaggac
gcgtggaccg agtgaccgtg gtttctgtgt ggtgtcacct gccagacccg ccgaagaagc cacctctttg
gagggtgcgc tctctggcac gcgccactcc cacccatccg tgggccgcca gcaccacgcg gccccccat
ccacatcgcg gccaccacgt ccctgggaca cgccttgtcc cccggtgtac gccgagacca agcacttcct
ctactcctca ggcgacaagg agcagctgcg gccctccttc ctactcagct ctctgaggcc cagcctgact
ggcgctcgga ggctcgtgga gaccatcttt ctggttcca ggccctggat gccagggact ccccgcaggt
tgccccgcct gccccagcgc tactggcaaa tgcggcccct gtttctggag ctgcttggga accacgcgca
gtgcccctac ggggtgctcc tcaagacgca ctgccgctg cgagctgcgg tcacccagc agccggtgtc
tgtgcccggg agaagcccca gggctctgtg gcggccccg aggaggagga cacagacccc cgtcgcctgg
tgcagctgct ccgccagcac agcagcccct ggcaggtgta cggcttcgtg cgggcctgcc tgcgccggct
ggtgccccca ggcctctggg gctccaggca caacgaacgc cgcttcctca ggaacaccaa gaagttcatc
tccctgggga agcatgccaa gctctcgctg caggagctga cgtggaagat gagcgtgcgg gactgcgctt
ggctgcgcag gagcccaggg gttggctgtg ttccggccgc agagcaccgt ctgcgtgagg agatcctggc
caagttcctg cactggctga tgagtgtgta cgtcgtcgag ctgctcaggt ctttctttta tgtcacggag
accacgtttc aaaagaacag gctcttttc taccggaaga gtgtctggag caagttgcaa agcattggaa
tcagacagca cttgaagagg gtgcagctgc gggagctgtc ggaagcagag gtcaggcagc atcgggaagc
caggcccgcc ctgctgacgt ccagactccg cttcatcccc aagcctgacg gctgcggcc gattgtgaac
atggactacg tcgtgggagc cagaacgttc cgcagagaaa agagggccga gcgtctcacc tcgagggtga
aggcactgtt cagcgtgctc aactacgagc gggcgcggcg ccccggcctc tgggcgcct ctgtgctggg
cctggacgat atccacaggg cctggcgcac cttcgtgctg cgtgtgcggg cccaggaccc gccgcctgag
ctgtactttg tcaaggtgga tgtgacgggc gcgtacgaca ccatccccca ggacaggctc acggaggtca
tcgccagcat catcaaaccc cagaacacgt actgcgtgcg tcggtatgcc gtggtccaga ggccgcccca
tgggcacgtc cgcaaggcct tcaagagcca cgtcctacgt ccagtgccag gggatccgc agggctccat
cctctccacg ctgctctgca gcctgtgcta cggcgacatg gagaacaagc tgtttgcggg gattcggcgg
gacgggctgc tcctgcgttt ggtggatgat ttcttgttgg tgacacctca cctcacccac gcgaaaacct
tcctcagcta tgcccggacc tccatcagag ccagtctcac cttcaaccgc ggcttcaagg ctgggaggaa
catgcgtcgc aaactctttg ggtcttgcg gctgaagtgt cacagcctgt ttctggattt gcaggtgaac
agcctccaga cggtgtgcac caacatctac aagatcctcc tgctgcaggc gtacaggttt cacgcatgtg
tgctgcagct cccatttcat cagcaagttt ggaagaaccc cacatttttc ctgcgcgtca tctctgacac
ggcctccctc tgctactcca tcctgaaagc caagaacgca gggatgtcgc tggggccaa ggcgccgcc
ggccctctgc cctccgaggc cgtgcagtgg ctgtgccacc aagcattcct gctcaagctg actcgacacc
gtgtcaccta cgtgccactc ctgggtcac tcaggacagc ccagacgcag ctgagtcgga gctcccggg
gacgacgctg actgccctgg aggccgcagc caacccggca ctgccctcag acttcaagac catcctggac
tgatggccac ccgcccacag ccaggccgag agcagacacc agcagccctg tcacgccggg ctctacgtcc
```

Figure 15

```
cagggaggga ggggcggccc acacccaggc ccgcaccgct gggagtctga ggcctgagtg agtgtttggc
cgaggcctgc atgtccggct gaaggctgag tgtccggctg aggcctgagc gagtgtccag ccaagggctg
agtgtccagc acacctgccg tcttcacttc cccacaggct ggcgctcggc tccacccag ggccagcttt
tcctcaccag gagcccggct tccactcccc acataggaat agtccatccc cagattcgcc attgttcacc
cctcgccctg ccctcctttg ccttccaccc ccaccatcca ggtggagacc ctgagaagga ccctgggagc
tctgggaatt tggagtgacc aaaggtgtgc cctgtacaca ggcgaggacc ctgcacctgg atgggggtcc
ctgtgggtca aattgggggg aggtgctgtg ggagtaaaat actgaatata tgagttttc agttttgaaa
aaaa
```

Figure 15 continued hTERT (human telomerase reverse transcriptase) (SEQ ID NO: 12)

Amino acid sequence of isoform 3:
```
MPRAPRCRAV RSLLRSHYRE VLPLATFVRR LGPQGWRLVQ RGDPAAFRAL VAQCLVCVPW DARPPPAAPS
FRQVSCLKEL VARVLQRLCE RGAKNVLAFG FALLDGARGG PPEAFTTSVR SYLPNTVTDA LRGSGAWGLL
LRRVGDDVLV HLLARCALFV LVAPSCAYQV CGPPLYQLGA ATQARPPPHA SGPRRRLGCE RAWNHSVREA
GVPLGLPAPG ARRRGGSASR SLPLPKRPRR GAAPEPERTP VGQGSWAHPG RTRGPSDRGF CVVSPARPAE
EATSLEGALS GTRHSHPSVG RQHHAGPPST SRPPRPWDTP CPPVYAETKH FLYSSGDKEQ LRPSFLLSSL
RPSLTGARRL VETIFLGSRP WMPGTPRRLP RLPQRYWQMR PLFLELLGNH AQCPYGVLLK THCPLRAAVT
PAAGVCAREK PQGSVAAPEE EDTDPRRLVQ LLRQHSSPWQ VYGFVRACLR RLVPPGLWGS RHNERRFLRN
TKKFISLGKH AKLSLQELTW KMSVRDCAWL RRSPGVGCVP AAEHRLREEI LAKFLHWLMS VYVVELLRSF
FYVTETTFQK NRLFFYRKSV WSKLQSIGIR QHLKRVQLRE LSEAEVRQHR EARPALLTSR LRFIPKPDGL
RPIVNMDYVV GARTFRREKR AERLTSRVKA LFSVLNYERA RRPGLLGASV LGLDDIHRAW RTFVLRVRAQ
DPPPELYFVK VDVTGAYDTI PQDRLTEVIA SIIKPQNTYC VRRYAVVQKA AHGHVRKAFK SHVLRPVPGD
PAGLHPLHAA LQPVLRRHGE QAVCGDSAGR AAPAFGG
```

Figure 16 hTERT (human telomerase reverse transcriptase) (SEQ ID NO: 13)

mRNA sequence of variant #4:
```
gcagcgctgc gtcctgctgc gcacgtggga agccctggcc ccggccaccc ccgcgatgcc gcgcgctccc
cgctgccgag ccgtgcgctc cctgctgcgc agccactacc gcgaggtgct gccgctggcc acgttcgtgc
ggcgcctggg gccccagggc tggcggctgg tgcagcgcgg ggacccggcg gctttccgcg cgctggtggc
ccagtgcctg gtgtgcgtgc cctgggacgc acggccgccc cccgccgccc cctccttccg ccaggtgtcc
tgcctgaagg agctggtggc ccgagtgctg cagaggctgt gcgagcgcgg cgcgaagaac gtgctggcct
tcggcttcgc gctgctggac ggggcccgcg ggggcccccc cgaggccttc accaccagcg tgcgcagcta
cctgcccaac acggtgaccg acgcactgcg ggggagcggg gcgtgggggc tgctgctgcg ccgcgtgggc
gacgacgtgc tggttcacct gctggcacgc tgcgcgctct ttgtgctggt ggctcccagc tgcgcctacc
aggtgtgcgg gccgccgctg taccagctcg gcgctgccac tcaggcccgg ccccgccac acgctagtgg
accccgaagg cgtctgggat gcgaacgggc tggaaccat agcgtcaggg aggccggggt ccccctgggc
ctgccagccc cgggtgcgag gaggcgcggg ggcagtgcca gccgaagtct gccgttgccc aagaggccca
ggcgtggcgc tgcccctgag ccggagcgga cgccgttgg gcaggggtcc tgggcccacc cgggcaggac
gcgtggaccg agtgaccgtg gtttctgtgt ggtgtcacct gccagacccg ccgaagaagc cacctctttg
gagggtgcgc tctctggcac gcgccactcc cacccatccg tgggccgcca gcaccacgcg gcccccccat
ccacatcgcg gccaccacgt ccctgggaca cgccttgtcc cccggtgtac gccgagacca agcacttcct
ctactcctca ggcgacaagg agcagctgcg gccctccttc ctactcagct ctctgaggcc cagcctgact
ggcgctcgga ggctcgtgga gaccatcttt ctgggttcca ggccctggat gccagggact ccccgcaggt
tgccccgcct gccccagccg tactgcgcaaa tgcggccgct gttctggag ctgcttggga accacggcgca
gtgcccctac ggggtgctcc tcaagacgca ctgcccgctg cgagctgcgg tcacccccagc agccggtgtc
tgtgcccggg agaagcccca gggctctgtg gcgcccccg aggaggagga cacagacccc cgtcgcctgg
tgcagctgct ccgccagcac agcagcccct ggcaggtgta cggcttcgtg cgggccgcc tgcgccggct
ggtgcccca ggcctctggg gctccaggca aacgaacgc cgcttcctca ggaacaccaa gaagttcatc
tccctgggga agcatgccaa gctctcgctg caggagctga cgtggaagat gagcgtgcgg gactgcgctt
ggctgcgcag gagcccaggg gttggctgtg ttccggccgc agagcaccgt ctgcgtgagg agatcctggc
caagttcctg cactggctga tgagtgtgta cgtcgtcgag ctgctcaggt cttctctttta tgtcacggag
accacgtttc aaaagaacag gctctttttc taccggaaga gtgtctggag caagttgcaa agcattggaa
tcagacagca cttgaagagg gtgcagctgc gggagctgtc ggaagcagag gtcaggcagc atcgggaagc
caggcccgcc ctgctgacgt ccagactccg cttcatcccc aagcctgacg gctgcggcc gattgtgaac
atggactacg tcgtgggagc cagaacgttc cgcagagaaa agagggccga gcgtctcacc tcgagggtga
aggcactgtt cagcgtgctc aactacgagc gggcgcggcg ccccggcctc ctgggcgcct ctgtgctggg
cctggacgat atccacaggg cctggcgcac cttcgtgctg cgtgtgcggg cccaggaccc gccgcctgag
ctgtactttg tcaaggacag gctcacggag gtcatcgcca gcatcatcaa ccccagaac acgtactgcg
tgcgtcggta tgccgtggtc cagaaggccg cccatgggca cgtccgcaag gccttcaaga gccacgtcct
acgtccagtg ccagggatcc ccgcaggct ccatcctctc cacgctgctc tgcagcctgt gctacggcga
catggagaac aagctgtttg cggggattcg gcgggacggg ctgctcctgc gtttggtgga tgatttcttg
ttggtgacac ctcacctcac ccacgcgaaa accttcctca gctatgcccg gacctccatc agagccagtc
tcaccttcaa ccgcggcttc aaggctggga ggaacatgcg tcgcaaactc tttggggtct gcggctgaa
gtgtcacagc ctgtttctgg atttgcaggt gaacagcctc cagacggtgt gcaccaacat ctacaagatc
ctcctgctgc aggcgtacag gtttcacgca tgtgtgctgc agctcccatt tcatcagcaa gtttggaaga
accccacatt tttcctgcgc gtcatctctg acacggcctc cctctgctac tccatcctga agccaagaa
cgcagggatg tcgctggggg ccaagggcgc cgccggccct ctgccctccg aggccgtgca gtggctgtgc
caccaagcat tcctgctcaa gctgactcga caccgtgtca cctacgtgcc actcctgggg tcactcagga
cagcccagac gcagctgagt cggaagctcc cggggacgac gctgactgcc ctggaggccg cagccaaccc
ggcactgccc tcagacttca agaccatcct ggactgatgg ccacccgccc acagccaggc cgagagcaga
caccagcagc cctgtcacgc cgggctctac gtcccaggga gggagggcg cccacaccc aggcccgcac
```

Figure 17

```
cgctgggagt ctgaggcctg agtgagtgtt tggccgaggc ctgcatgtcc ggctgaaggc tgagtgtccg
gctgaggcct gagcgagtgt ccagccaagg gctgagtgtc cagcacacct gccgtcttca cttccccaca
ggctggcgct cggctccacc ccagggccag cttttcctca ccaggagccc ggcttccact ccccacatag
gaatagtcca tccccagatt cgccattgtt caccccctcgc cctgccctcc tttgccttcc accccacca
tccaggtgga gaccctgaga aggaccctgg gagctctggg aatttggagt gaccaaaggt gtgccctgta
cacaggcgag gaccctgcac ctggatgggg gtccctgtgg gtcaaattgg ggggaggtgc tgtgggagta
aaatactgaa tatatgagtt tttcagtttt gaaaaaaa
```

Figure 17 continued hTERT (human telomerase reverse transcriptase) (SEQ ID NO: 14)

Amino acid sequence of isoform 4:

```
MPRAPRCRAV RSLLRSHYRE VLPLATFVRR LGPQGWRLVQ RGDPAAFRAL VAQCLVCVPW DARPPPAAPS
FRQVSCLKEL VARVLQRLCE RGAKNVLAFG FALLDGARGG PPEAFTTSVR SYLPNTVTDA LRGSGAWGLL
LRRVGDDVLV HLLARCALFV LVAPSCAYQV CGPPLYQLGA ATQARPPPHA SGPRRRLGCE RAWNHSVREA
GVPLGLPAPG ARRRGGSASR SLPLPKRPRR GAAPEPERTP VGQGSWAHPG RTRGPSDRGF CVVSPARPAE
EATSLEGALS GTRHSHPSVG RQHHAGPPST SRPPRPWDTP CPPVYAETKH FLYSSGDKEQ LRPSFLLSSL
RPSLTGARRL VETIFLGSRP WMPGTPRRLP RLPQRYWQMR PLFLELLGNH AQCPYGVLLK THCPLRAAVT
PAAGVCAREK PQGSVAAPEE EDTDPRRLVQ LLRQHSSPWQ VYGFVRACLR RLVPPGLWGS RHNERRFLRN
TKKFISLGKH AKLSLQELTW KMSVRDCAWL RRSPGVGCVP AAEHRLREEI LAKFLHWLMS VYVVELLRSF
FYVTETTFQK NRLFFYRKSV WSKLQSIGIR QHLKRVQLRE LSEAEVRQHR EARPALLTSR LRFIPKPDGL
RPIVNMDYVV GARTFRREKR AERLTSRVKA LFSVLNYERA RRPGLLGASV LGLDDIHRAW RTFVLRVRAQ
DPPPELYFVK DRLTEVIASI IKPQNTYCVR RYAVVQKAAH GHVRKAFKSH VLRPVPGDPA GLHPLHAALQ
PVLRRHGEQA VCGDSAGRAA PAFGG
```

Figure 18

CD44 (SEQ ID NO: 15)

mRNA sequence of variant #1:
```
gagaagaaag ccagtgcgtc tctgggcgca ggggccagtg gggctcggag gcacaggcac cccgcgacac
tccaggttcc ccgacccacg tccctggcag ccccgattat ttacagcctc agcagagcac ggggcggggg
cagaggggcc cgcccgggag ggctgctact tcttaaaacc tctgcgggct gcttagtcac agcccccctt
gcttgggtgt gtccttcgct cgctccctcc ctccgtctta ggtcactgtt ttcaacctcg aataaaaact
gcagccaact tccgaggcag cctcattgcc cagcggaccc cagcctctgc caggttcggt ccgccatcct
cgtcccgtcc tccgccggcc cctgccccgc gcccagggat cctccagctc ctttcgcccg cgccctccgt
tcgctccgga caccatggac aagtttttggt ggcacgcagc ctggggactc tgcctcgtgc cgctgagcct
ggcgcagatc gatttgaata taacctgccg ctttgcaggt gtattccacg tggagaaaaa tggtcgctac
agcatctctc ggacggaggc cgctgacctc tgcaaggctt caatagcac cttgcccaca atggcccaga
tggagaaagc tctgagcatc ggatttgaga cctgcaggta tgggttcata gaagggcacg tggtgattcc
ccggatccac cccaactcca tctgtgcagc aaacaacaca ggggtgtaca tcctcacatc aacacctcc
cagtatgaca catattgctt caatgcttca gctccacctg aagaagatta tacatcagtc acagacctgc
ccaatgcctt tgatggacca attaccataa ctattgttaa ccgtgatggc acccgctatg tccagaaagg
agaatacaga acgaatcctg aagacatcta ccccagcaac cctactgatg atgacgtgag cagcggctcc
tccagtgaaa ggagcagcac tcaggaggt tacatctttt acaccttttc tactgtacac cccatcccag
acgaagacag tccctggatc accgacagca cagacagaat ccctgctacc actttgatga gcactagtgc
tacagcaact gagacagcaa ccaagaggca gaaacctgg gattggtttt catggttgtt tctaccatca
gagtcaaaga atcatcttca cacaacaaca caaatggctg gtacgtcttc aaataccatc tcagcaggct
gggagccaaa tgaagaaaat gaagatgaaa gagacagaca cctcagtttt tctggatcag gcattgatga
tgatgaagat tttatctcca gcaccatttc aaccacacca cgggcttttg accacacaaa acagaaccag
gactggaccc agtggaaccc aagccattca aatccggaag tgctacttca gacaaccaca aggatgactg
atgtagacag aaatggcacc actgcttatg aaggaaactg gaacccagaa gcacacctc ccctcattca
ccatgagcat catgaggaag aagagacccc acattctaca agcacaatcc aggcaactcc tagtagtaca
acggaagaaa cagctaccca gaaggaacag tggtttggca acagatggca tgagggatat cgccaaacac
ccaaagaaga ctcccattcg acaacaggga cagctgcagc ctcagctcat accagccatc aatgcaagg
aaggacaaca ccaagcccag aggacagttc ctggactgat tcttcaacc caatctcaca ccccatggga
cgaggtcatc aagcaggaag aaggatggat atggactcca gtcatagtat aacgcttcag cctactgcaa
atccaaacac aggtttggtg aagatttgg acaggacagg acctctttca atgacaacgc agcagagtaa
ttctcagagc ttctctacat cacatgaagg cttggaagaa gataaagacc atccaacaac ttctactctg
acatcaagca ataggaatga tgtcacaggt ggaagaagag acccaaatca ttctgaaggc tcaactactt
tactggaagg ttatacctct cattacccac acacgaagga agcaggacc ttcatcccag tgacctcagc
taagactggg tcctttggag ttactgcagt tactgttgga gattccaact ctaatgtcaa tcgttcctta
tcaggagacc aagacacatt ccaccccagt gggggtccc ataccactca tggatctgaa tcagatggac
actcacatgg gagtcaagaa ggtggagcaa acacaacctc tggtcctata aggacacccc aaattccaga
atggctgatc atcttggcat ccctcttggc cttggctttg attcttgcag tttgcattgc agtcaacagt
cgaagaagt gtgggcagaa gaaaaagcta gtgatcaaca gtggcaatgg agctgtggag acagaaagc
caagtggact caacggagag ccagcaagt ctcaggaaat ggtgcatttg gtgaacaagg agtcgtcaga
aactccagac cagtttatga cagctgatga dacaaggaac ctgcagaatg tggacatgaa gattggggtg
taacacctac accattatct tggaaagaaa caaccgttgg aaacataacc attcaggga gctgggacac
ttaacagatg caatgtgcta ctgattgttt cattgcgaat ctttttttagc ataaaattt ctactctttt
tgttttttgt gttttgttct ttaaagtcag gtccaatttg taaaaacagc attgctttct gaaattaggg
cccaattaat aatcagcaag aatttgatcg ttccagttcc cacttggagg cctttcatcc ctcgggtgtg
ctatggatgg cttctaacaa aaactacaca tatgtattcc tgatcgccaa cctttccccc accagctaag
gacatttccc agggttaata gggcctggtc cctgggagga aattttgaatg ggtccatttt gcccttccat
agcctaatcc ctgggcattg cttttccactg aggttggggg ttggggtgta ctagttacac atcttcaaca
gacccccctct agaaattttt cagatgcttc tgggagacac ccaaagggtg aagctattta tctgtagtaa
```

Figure 19

```
actatttatc tgtgtttttg aaatattaaa ccctggatca gtcctttgat cagtataatt ttttaaagtt
actttgtcag aggcacaaaa gggtttaaac tgattcataa taaatatctg tacttcttcg atcttcacct
tttgtgctgt gattcttcag tttctaaacc agcactgtct gggtccctac aatgtatcag gaagagctga
gaatggtaag gagactcttc taagtcttca tctcagagac cctgagttcc cactcagacc cactcagcca
aatctcatgg aagaccaagg agggcagcac tgttttttgtt ttttgttttt tgttttttttt ttttgacact
gtccaaaggt tttccatcct gtcctggaat cagagttgga agctgaggag cttcagcctc ttttatggtt
taatgccac ctgttctctc ctgtgaaagg ctttgcaaag tcacattaag tttgcatgac ctgttatccc
tggggcccta tttcatagag gctggcccta ttagtgattt ccaaaaacaa tatggaagtg ccttttgatg
tcttacaata agagaagaag ccaatggaaa tgaaagagat tggcaaaggg gaaggatgat gccatgtaga
tcctgtttga cattttttatg gctgtatttg taaacttaaa cacaccagtg tctgttcttg atgcagttgc
tatttaggat gagttaagtg cctggggagt ccctcaaaag gttaaaggga ttcccatcat tggaatctta
tcaccagata ggcaagttta tgaccaaaca agagagtact ggctttatcc tctaacctca tattttctcc
cacttggcaa gtcctttgtg gcatttattc atcagtcagg gtgtccgatt ggtcctagaa cttccaaagg
ctgcttgtca tagaagccat tgcatctata aagcaacggc tcctgttaaa tggtatctcc tttctgaggc
tcctactaaa agtcatttgt tacctaaact tatgtgctta acaggcaatg cttctcagac cacaaagcag
aaagaagaag aaaagctcct gactaaatca gggctgggct tagacagagt tgatctgtag aatatcttta
aaggagagat gtcaactttc tgcactattc ccagcctctg ctcctccctg tctaccctct cccctccctc
tctccctcca cttcacccca caatcttgaa aaacttcctt tctcttctgt gaacatcatt ggccagatcc
attttcagtg gtctggattt cttttattt tcttttcaac ttgaaagaaa ctggacatta ggccactatg
tgttgttact gccactagtg ttcaagtgcc tcttgttttc ccagagattt cctgggtctg ccagaggccc
agacaggctc actcaagctc tttaactgaa aagcaacaag ccactccagg acaaggttca aaatggttac
aacagcctct acctgtcgcc ccagggagaa agggggtagtg atacaagtct catagccaga gatggttttc
cactccttct agatattccc aaaaagaggc tgagacagga ggttattttc aatttatttt tggaattaaa
tactttttttc cctttattac tgttgtagtc cctcacttgg atatacctct gttttcacga tagaaataag
ggaggtctag agcttctatt ccttggccat tgtcaacgga gagctggcca agtcttcaca aacccttgca
acattgcctg aagtttatgg aataagatgt attctcactc ccttgatctc aagggcgtaa ctctggaagc
acagcttgac tacacgtcat ttttaccaat gattttcagg tgacctgggc taagtcattt aaactgggtc
tttataaaag taaaaggcca acatttaatt attttgcaaa gcaacctaag agctaaagat gtaatttttc
ttgcaattgt aaatcttttg tgtctcctga agacttccct taaaattagc tctgagtgaa aaatcaaaag
agacaaaaga catcttcgaa tccatatttc aagcctggta gaattggctt ttctagcaga acctttccaa
aagttttata ttgagattca taacaacacc aagaattgat tttgtagcca acattcattc aatactgtta
tatcagagga gtaggagaga ggaaacattt gacttatctg gaaaagcaaa atgtacttaa gaataagaat
aacatggtcc attcacctt atgttataga tatgtctttg tgtaaatcat ttgttttgag ttttcaaaga
atagcccatt gttcattctt gtgctgtaca atgaccactg ttattgttac tttgacttttt cagagcacac
ccttcctctg gttttttgtat atttattgat ggatcaataa taatgaggaa agcatgatat gtatattgct
gagttgaaag cacttattgg aaaatattaa aaggctaaca ttaaaagact aaggaaaca gaaaaaaaaa
aaaaaaaa
```

Figure 19 continued

CD44 (SEQ ID NO: 16)

Amino acid sequence of isoform 1:
```
MDKFWWHAAW GLCLVPLSLA QIDLNITCRF AGVFHVEKNG RYSISRTEAA DLCKAFNSTL PTMAQMEKAL
SIGFETCRYG FIEGHVVIPR IHPNSICAAN NTGVYILTSN TSQYDTYCFN ASAPPEEDCT SVTDLPNAFD
GPITITIVNR DGTRYVQKGE YRTNPEDIYP SNPTDDDVSS GSSSERSSTS GGYIFYTFST VHPIPDEDSP
WITDSTDRIP ATTLMSTSAT ATETATKRQE TWDWFSWLFL PSESKNHLHT TTQMAGTSSN TISAGWEPNE
ENEDERDRHL SFSGSGIDDD EDFISSTIST TPRAFDHTKQ NQDWTQWNPS HSNPEVLLQT TTRMTDVDRN
GTTAYEGNWN PEAHPPLIHH EHHEEEETPH STSTIQATPS STTEETATQK EQWFGNRWHE GYRQTPKEDS
HSTTGTAAAS AHTSHPMQGR TTPSPEDSSW TDFFNPISHP MGRGHQAGRR MDMDSSHSIT LQPTANPNTG
LVEDLDRTGP LSMTTQQSNS QSFSTSHEGL EEDKDHPTTS TLTSSNRNDV TGGRRDPNHS EGSTTLLEGY
TSHYPHTKES RTFIPVTSAK TGSFGVTAVT VGDSNSNVNR SLSGDQDTFH PSGGSHTTHG SESDGHSHGS
QEGGANTTSG PIRTPQIPEW LIILASLLAL ALILAVCIAV NSRRCGQKK KLVINSGNGA VEDRKPSGLN
GEASKSQEMV HLVNKESSET PDQFMTADET RNLQNVDMKI GV
```

Figure 20

CD44 (SEQ ID NO: 17)

mRNA sequence of variant #2:

```
gagaagaaag ccagtgcgtc tctgggcgca ggggccagtg gggctcggag cacaggcac cccgcgacac
tccaggttcc ccgacccacg tccctggcag ccccgattat ttacagcctc agcagagcac ggggcggggg
cagaggggcc cgcccgggag ggctgctact tcttaaaacc tctgcgggct gcttagtcac agccccctt
gcttgggtgt gtccttcgct cgctccctcc ctccgtctta ggtcactgtt ttcaacctcg aataaaaact
gcagccaact tccgaggcag cctcattgcc cagcggaccc cagcctctgc caggttcggt ccgccatcct
cgtcccgtcc tccgccggcc cctgccccgc gcccagggat cctccagctc ctttcgcccg cgcctccgt
tcgctccgga caccatggac aagttttggt ggcacgcagc ctggggactc tgcctcgtgc cgctgagcct
ggcgcagatc gatttgaata taacctgccg ctttgcaggt gtattccacg tggagaaaaa tggtcgctac
agcatctctc ggacggaggc cgctgacctc tgcaaggctt caatagcac cttgcccaca atggcccaga
tggagaaagc tctgagcatc ggatttgaga cctgcaggta tgggttcata aagggcacg tggtgattcc
ccggatccac cccaactcca tctgtgcagc aaacaacaca ggggtgtaca tcctcacatc aacacctcc
cagtatgaca catattgctt caatgcttca gctccacctg aagaagattg tacatcagtc acagacctgc
ccaatgcctt tgatggacca attaccataa ctattgttaa ccgtgatggc accgctatg tccagaaagg
agaatacaga acgaatcctg aagacatcta ccccagcaac cctactgatg atgacgtgag cagcggctcc
tccagtgaaa ggagcagcac ttcaggaggt tacatctttt acactttttc tactgtacac cccatcccag
acgaagacag tccctggatc accgacagca cagacagaat ccctgctacc agtacgtctt caaataccat
ctcagcaggc tgggagccaa atgaagaaaa tgaagatgaa agagacagac acctcagttt ttctggatca
ggcattgatg atgatgaaga ttttatctcc agcaccttt caaccacacc acgggtactt gaccacacaa
aacagaacca ggactggacc cagtgaacc caagccattc aaatccggaa gtgctacttc agacaaccac
aaggatgact gatgtagaca gaaatggcac cactgcttat gaaggaaact ggaacccaga agcacaccct
cccctcattc accatgagca tcatgaggaa gagagaccc cacattctac aagcacaatc caggcaactc
ctagtagtac aacggaagaa acagctaccc agaaggaaca gtggtttggc aacagatggc atgagggata
tcgccaaaca cccaagaag actcccattc gacaacaggg acagctgcag cctcagctca taccagccat
ccaatgcaag gaaggacaac accaagccca gaggacagtt cctggactga tttcttcaac caatctcac
accccatggg acgaggtcat caagcaggaa gaaggatgga tatggactcc agtcatagta taacgcttca
gcctactgca aatccaaaca caggttttggt ggaagatttg acaggacag gacctcttc aatgacaacg
cagcagagta attctcagag cttctctaca tcacatgaag gcttggaaga agataaagac catccaacaa
cttctactct gacatcaagc aataggaatg atgtcacagg tggaagaaga gacccaaatc attctgaagg
ctcaactact ttactggaag gttataccctc tcattaccca cacacgaagg aaagcaggac cttcatccca
gtgacctcag ctaagactgg gtcctttgga gttactgcag ttactgttgg agattccaac tctaatgtca
atcgttcctt atcaggagac caagacacat tccacccag tgggggtcc cataccactc atggatctga
atcagatgga cactcacatg ggagtcaaga aggtggagca aacacaacct ctggtcctat aaggacaccc
caaattccag aatggctgat catcttggca tccctcttgg ccttggcttt gattcttgca gtttgcattg
cagtcaacag tcgaagaagg tgtgggcaga gaaaaagct agtgatcaac agtggcaatg gagctgtgga
ggacagaaag ccaagtggac tcaacggaga ggccagcaag tctcaggaaa tggtgcattt ggtgaacaag
gagtcgtcag aaactccaga ccagtttatg acagctgatg agacaaggaa cctgcagaat gtggacatga
agattggggt gtaaaccta caccattatc ttggaaagaa acaaccgttg aaacataac cattacaggg
agctgggaca cttaacagat gcaatgtgct actgattgtt tcattgcgaa tctttttttag cataaaattt
tctactcttt ttgtttttg tgttttgttc tttaaagtca ggtccaattt gtaaaacag cattgctttc
tgaaattagg gcccaattaa taatcagcaa gaatttgatc gttccagttc ccacttggag gcctttcatc
cctcgggtgt gctatggatg gcttctaaca aaaactacac atatgtattc ctgatcgcca cctttcccc
caccagctaa ggacatttcc cagggttaat agggcctggt ccctgggagg aaatttgaat gggtccattt
tgcccttcca tagcctaatc cctgggcatt gctttccact gaggttgggg gttgggtgt actagttaca
catcttcaac agacccctc tagaaatttt tcagatgctt ctgggagaca cccaaaggt gaagctattt
atctgtagta aactatttat ctgtgttttt gaaatattaa accctggatc agtcctttga tcagtataat
tttttaaagt tactttgtca gaggcacaaa agggtttaaa ctgattcata ataaatatct gtacttcttc
```

Figure 21

```
gatcttcacc ttttgtgctg tgattcttca gtttctaaac cagcactgtc tgggtcccta caatgtatca
ggaagagctg agaatggtaa ggagactctt ctaagtcttc atctcagaga ccctgagttc ccactcagac
ccactcagcc aaatctcatg gaagaccaag gagggcagca ctgttttgt tttttgtttt ttgtttttt
ttttgacac tgtccaaagg ttttccatcc tgtcctggaa tcagagttgg aagctgagga gcttcagcct
cttttatggt ttaatggcca cctgttctct cctgtgaaag gctttgcaaa gtcacattaa gtttgcatga
cctgttatcc ctggggccct atttcataga ggctggccct attagtgatt tccaaaaaca atatggaagt
gccttttgat gtcttacaat aagagaagaa gccaatggaa atgaaagaga ttggcaaagg ggaaggatga
tgccatgtag atcctgtttg acattttat ggctgtattt gtaaacttaa acacaccagt gtctgttctt
gatgcagttg ctatttagga tgagttaagt gcctggggag tccctcaaaa ggttaaaggg attcccatca
ttggaatctt atcaccagat aggcaagttt atgaccaaac aagagagtac tggctttatc ctctaacctc
atattttctc ccacttggca agtcctttgt ggcatttatt catcagtcag ggtgtccgat tggtcctaga
acttccaaag gctgcttgtc atagaagcca ttcatctat aaagcaacgg ctcctgttaa atggtatctc
ctttctgagg ctcctactaa aagtcatttg ttacctaaac ttatgtgctt aacaggcaat gcttctcaga
ccacaaagca gaaagaagaa gaaagctcc tgactaaatc agggctgggc ttagacagag ttgatctgta
gaatatcttt aaaggagaga tgtcaacttt ctgcactatt cccagcctct gctcctccct gtctaccctc
tcccctccct ctctccctcc acttcacccc acaatcttga aaaacttcct ttctcttctg tgaacatcat
tggccagatc cattttcagt ggtctggatt ttttttatt ttctttttcaa cttgaaagaa actggacatt
aggccactat gtgttgttac tgccactagt gttcaagtgc ctcttgtttt cccagagatt tcctgggtct
gccagaggcc cagacaggct cactcaagct ctttaactga aaagcaacaa gccactccag gacaaggttc
aaaatggtta caacagcctc tacctgtcgc cccagggaga aagggggtagt gatacaagtc tcatagccag
agatggtttt ccactccttc tagatattcc caaaaagagg ctgagacagg aggttatttt caatttatt
ttggaattaa atactttttt ccctttatta ctgttgtagt ccctcacttg gatatacctc tgttttcacg
atagaaataa gggaggtcta gagcttctat tccttggcca ttgtcaacgg agagctggcc aagtcttcac
aaacccttgc aacattgcct gaagtttatg gaataagatg tattctcact cccttgatct caagggcgta
actctggaag cacagcttga ctacacgtca tttttaccaa tgattttcag gtgacctggg ctaagtcatt
taaactgggt ctttataaaa gtaaaaggcc aacatttaat tattttgcaa agcaacctaa gagctaaaga
tgtaatttt cttgcaattg taaatctttt gtgtctcctg aagcttccc ttaaaattag ctctgagtga
aaaatcaaaa gagacaaaag acatcttcga atccatattt caagcctggt agaattggct tttctagcag
aacctttcca aaagttttat attgagattc ataacaacac caagaattga ttttgtagcc aacattcatt
caatactgtt atatcagagg agtaggagag aggaaacatt tgacttatct ggaaaagcaa aatgtactta
agaataagaa taacatggtc cattcacctt tatgttatag atatgtcttt gtgtaaatca tttgttttga
gttttcaaag aatagcccat tgttcattct tgtgctgtac aatgaccact gttattgtta ctttgacttt
tcagagcaca cccttcctct ggttttgta tatttattga tggatcaata ataatgagga aagcatgata
tgtatattgc tgagttgaaa gcacttattg gaaaatatta aaggctaac attaaaagac taaaggaaac
agaaaaaaaa aaaaaaaaa
```

Figure 21 continued

CD44 (SEQ ID NO: 18)

Amino acid sequence of isoform 2:
```
MDKFWWHAAW GLCLVPLSLA QIDLNITCRF AGVFHVEKNG RYSISRTEAA DLCKAFNSTL PTMAQMEKAL
SIGFETCRYG FIEGHVVIPR IHPNSICAAN NTGVYILTSN TSQYDTYCFN ASAPPEEDCT SVTDLPNAFD
GPITITIVNR DGTRYVQKGE YRTNPEDIYP SNPTDDDVSS GSSSERSSTS GGYIFYTFST VHPIPDEDSP
WITDSTDRIP ATSTSSNTIS AGWEPNEENE DERDRHLSFS GSGIDDDEDF ISSTISTTPR AFDHTKQNQD
WTQWNPSHSN PEVLLQTTTR MTDVDRNGTT AYEGNWNPEA HPPLIHHEHH EEEETPHSTS TIQATPSSTT
EETATQKEQW FGNRWHEGYR QTPKEDSHST TGTAAASAHT SHPMQGRTTP SPEDSSWTDF FNPISHPMGR
GHQAGRRMDM DSSHSITLQP TANPNTGLVE DLDRTGPLSM TTQQSNSQSF STSHEGLEED KDHPTTSTLT
SSNRNDVTGG RRDPNHSEGS TTLLEGYTSH YPHTKESRTF IPVTSAKTGS FGVTAVTVGD SNSNVNRSLS
GDQDTFHPSG GSHTTHGSES DGHSHGSQEG GANTTSGPIR TPQIPEWLII LASLLALALI LAVCIAVNSR
RRCGQKKKLV INSGNGAVED RKPSGLNGEA SKSQEMVHLV NKESSETPDQ FMTADETRNL QNVDMKIGV
```

Figure 22

CD44 (SEQ ID NO: 19)

mRNA sequence of variant #3:

```
gagaagaaag ccagtgcgtc tctgggcgca ggggccagtg gggctcggag gcacaggcac cccgcgacac
tccaggttcc ccgacccacg tccctggcag cccgattat ttacagcctc agcagagcac ggggcggggg
cagagggcc cgcccgggag ggctgctact tcttaaaacc tctgcgggct gcttagtcac agcccccctt
gcttgggtgt gtccttcgct cgctccctcc ctccgtctta ggtcactgtt ttcaacctcg aataaaaact
gcagccaact tccgaggcag cctcattgcc cagcggaccc cagcctctgc caggttcggt ccgccatcct
cgtcccgtcc tccgccggcc cctgccccgc gcccagggat cctccagctc ctttcgcccg cgcctccgt
tcgctccgga caccatggac aagttttggt ggcacgcagc ctggggactc tgcctcgtgc cgctgagcct
ggcgcagatc gatttgaata taacctgccg ctttgcaggt gtattccacg tggagaaaaa tggtcgctac
agcatctctc ggacggaggc cgctgacctc tgcaaggctt caatagcac cttgcccaca atgcccaga
tggagaaagc tctgagcatc ggatttgaga cctgcaggta tgggttcata gaagggcacg tggtgattcc
ccggatccac cccaactcca tctgtgcagc aaacaacaca ggggtgtaca tcctcacatc caacacctcc
cagtatgaca catattgctt caatgcttca gctccacctg aagaagattg tacatcagtc acagacctgc
ccaatgcctt tgatggacca attaccataa ctattgttaa ccgtgatggc cccgctatg tccagaaagg
agaatacaga acgaatcctg aagacatcta ccccagcaac cctactgatg atgacgtgag cagcggctcc
tccagtgaaa ggagcagcac tcaggaggt tacatctttt acacctttc tactgtacac cccatcccag
acgaagacag tccctggatc accgacagca cagacagaat ccctgctacc aatatggact ccagtcatag
tataacgctt cagcctactg caaatccaaa cacaggtttg gtggaagatt tggacaggac aggacctctt
tcaatgacaa cgcagcagag taattctcag agcttctcta catcacatga aggcttggaa gaagataaag
accatccaac aacttctact ctgacatcaa gcaataggaa tgatgtcaca ggtggaagaa gagacccaaa
tcattctgaa ggctcaacta ctttactgga aggttatacc tctcattacc cacacacgaa ggaaagcagg
accttcatcc cagtgacctc agctaagact gggtcctttg gagttactgc agttactgtt ggagattcca
actctaatgt caatcgttcc ttatcaggag accaagacac attccacccc agtgggggt cccataccac
tcatggatct gaatcagatg gacactcaca tgggagtcaa gaaggtggag caaacacaac ctctggtcct
ataaggacac cccaaattcc agaatggctg atcatcttgg catccctctt ggccttggct ttgattcttg
cagtttgcat tgcagtcaac agtcgaagaa ggtgtgggca gaagaaaaag ctagtgatca acagtggcaa
tggagctgtg gaggacagaa agccaagtgg actcaacgga gaggccagca agtctcagga atggtgcat
ttggtgaaca aggagtcgtc agaaactcca gaccagttta tgacagctga tgagacaagg aacctgcaga
atgtggacat gaagattggg gtgtaacacc tacaccatta tcttggaaag aaacaaccgt tggaaacata
accattacag ggagctggga cacttaacag atgcaatgtg ctactgattg tttcattgcg aatctttttt
agcataaaat tttctactct ttttgttttt tgtgttttgt tcttaaagt caggtccaat ttgtaaaaac
agcattgctt tctgaaatta gggcccaatt aataatcagc aagaatttga tcgttccagt tcccacttgg
aggcctttca tccctcgggt gtgctatgga tggcttctaa caaaaactac acatatgtat tcctgatcgc
caacctttcc cccaccagct aaggacattt cccagggtta ataggcctg gtccctggga ggaaatttga
atgggtccat tttgcccttc catagcctaa tccctgggca ttgcttcca ctgaggttgg gggttggggt
gtactagtta cacatcttca acagacccc tctagaaatt tttcagatgc ttctgggaga cacccaaagg
gtgaagctat ttatctgtag taaactattt atctgtgttt tgaaatatt aaaccctgga tcagtccttt
gatcagtata attttttaaa gttacttgt cagaggcaca aaagggttta aactgattca taataaatat
ctgtacttct tcgatcttca ccttttgtgc tgtgattctt cagtttctaa accagcactg tctgggtccc
tacaatgtat caggaagagc tgagaatggt aaggagactc ttctaagtct tcatctcaga gaccctgagt
tcccactcag acccactcag ccaaatctca tggaagacca aggagggcag cactgttttt gttttttgtt
ttttgttttt ttttttgac actgtccaaa ggttttccat cctgtcctgg aatcagagtt ggaagctgag
gagcttcagc ctcttttatg gtttaatggc cacctgttct ctcctgtgaa aggctttgca aagtcacatt
aagtttgcat gacctgttat ccctggggcc ctatttcata gaggctggcc ctattagtga tttccaaaaa
caatatggaa gtgccttttg atgtcttaca ataagagaag aagccaatgg aaatgaaaga gattggcaaa
ggggaaggat gatgccatgt agatcctgtt tgacattttt atggctgtat ttgtaaactt aaacacacca
```

Figure 23

```
gtgtctgttc ttgatgcagt tgctatttag gatgagttaa gtgcctgggg agtccctcaa aaggttaaag
ggattcccat cattggaatc ttatcaccag ataggcaagt ttatgaccaa acaagagagt actggctttta
tcctctaacc tcatattttc tcccacttgg caagtccttt gtggcattta ttcatcagtc agggtgtccg
attggtccta gaacttccaa aggctgcttg tcatagaagc cattgcatct ataaagcaac ggctcctgtt
aaatggtatc tcctttctga ggctcctact aaaagtcatt tgttacctaa acttatgtgc ttaacaggca
atgcttctca gaccacaaag cagaaagaag aagaaaagct cctgactaaa tcagggctgg gcttagacag
agttgatctg tagaatatct ttaaaggaga gatgtcaact ttctgcacta ttcccagcct ctgctcctcc
ctgtctaccc tctcccctcc ctctctccct ccacttcacc ccacaatctt gaaaaacttc ctttctcttc
tgtgaacatc attggccaga tccattttca gtggtctgga tttctttta ttttcttttc aacttgaaag
aaactggaca ttaggccact atgtgttgtt actgccacta gtgttcaagt gcctcttgtt ttcccagaga
tttcctgggt ctgccagagg cccagacagg ctcactcaag ctctttaact gaaaagcaac aagccactcc
aggacaaggt tcaaaatggt tacaacagcc tctacctgtc gccccaggga gaaagggta gtgatacaag
tctcatagcc agagatggtt ttccactcct tctagatatt cccaaaaaga ggctgagaca ggaggttatt
ttcaatttta ttttggaatt aaatactttt ttccctttat tactgttgta gtccctcact tggatatacc
tctgttttca cgatagaaat aagggaggtc tagagcttct attccttggc cattgtcaac ggagagctgg
ccaagtcttc acaaacccctt gcaacattgc ctgaagttta tggaataaga tgtattctca ctcccttgat
ctcaagggcg taactctgga agcacagctt gactacacgt catttttacc aatgattttc aggtgacctg
ggctaagtca tttaaactgg gtctttataa aagtaaaagg ccaacattta attatttgc aaagcaacct
aagagctaaa gatgtaattt ttcttgcaat tgtaaatctt ttgtgtctcc tgaagacttc ccttaaaatt
agctctgagt gaaaaatcaa aagagacaaa agacatcttc gaatccatat ttcaagcctg gtagaattgg
cttttctagc agaacctttc caaaagtttt atattgagat tcataacaac accaagaatt gatttttgtag
ccaacattca ttcaatactg ttatatcaga ggagtaggag agaggaaaca tttgacttat ctggaaaagc
aaaatgtact taagaataag aataacatgg tccattcacc tttatgttat agatatgtct ttgtgtaaat
catttgtttt gagttttcaa agaatagccc attgttcatt cttgtgctgt acaatgacca ctgttattgt
tactttgact tttcagagca cacccttcct ctggttttttg tatatttatt gatggatcaa taataatgag
gaaagcatga tatgtatatt gctgagttga aagcacttat tggaaaatat taaaggcta acattaaaag
actaaaggaa acagaaaaaa aaaaaaaaaa a
```

Figure 23 continued

CD44 (SEQ ID NO: 20)

Amino acid sequence of isoform 3:

```
MDKFWWHAAW GLCLVPLSLA QIDLNITCRF AGVFHVEKNG RYSISRTEAA DLCKAFNSTL PTMAQMEKAL
SIGFETCRYG FIEGHVVIPR IHPNSICAAN NTGVYILTSN TSQYDTYCFN ASAPPEEDCT SVTDLPNAFD
GPITITIVNR DGTRYVQKGE YRTNPEDIYP SNPTDDDVSS GSSSERSSTS GGYIFYTFST VHPIPDEDSP
WITDSTDRIP ATNMDSSHSI TLQPTANPNT GLVEDLDRTG PLSMTTQQSN SQSFSTSHEG LEEDKDHPTT
STLTSSNRND VTGGRRDPNH SEGSTTLLEG YTSHYPHTKE SRTFIPVTSA KTGSFGVTAV TVGDSNSNVN
RSLSGDQDTF HPSGGSHTTH GSESDGHSHG SQEGGANTTS GPIRTPQIPE WLIILASLLA LALILAVCIA
VNSRRRCGQK KKLVINSGNG AVEDRKPSGL NGEASKSQEM VHLVNKESSE TPDQFMTADE TRNLQNVDMK
IGV
```

Figure 24

CD44 (SEQ ID NO: 21)

mRNA sequence of variant #4:

```
gagaagaaag ccagtgcgtc tctgggcgca ggggccagtg gggctcggag gcacaggcac cccgcgacac
tccaggttcc ccgacccacg tccctggcag ccccgattat ttacagcctc agcagagcac ggggcggggg
cagaggggcc cgcccgggag ggctgctact tcttaaaacc tctgcgggct gcttagtcac agcccccctt
gcttgggtgt gtccttcgct cgctccctcc ctccgtctta ggtcactgtt ttcaacctcg aataaaaact
gcagccaact tccgaggcag cctcattgcc cagcggaccc cagcctctgc caggttcggt ccgccatcct
cgtcccgtcc tccgccggcc cctgccccgc gcccagggat cctccagctc ctttcgcccg cgccctccgt
tcgctccgga caccatggac aagttttggt ggcacgcagc ctggggactc tgcctcgtgc cgctgagcct
ggcgcagatc gatttgaata taacctgccg ctttgcaggt gtattccacg tggagaaaaa tggtcgctac
agcatctctc ggacggaggc cgctgacctc tgcaaggctt caatagcac cttgcccaca atgcccaga
tggagaaagc tctgagcatc ggatttgaga cctgcaggta tgggttcata gaagggcacg tggtgattcc
ccggatccac cccaactcca tctgtgcagc aaacaacaca ggggtgtaca tcctcacatc caacacctcc
cagtatgaca catattgctt caatgcttca gctccacctg aagaagattg tacatcagtc acagacctgc
ccaatgcctt tgatggacca attaccataa ctattgttaa ccgtgatggc acccgctatg tccagaaagg
agaatacaga acgaatcctg aagacatcta ccccagcaac cctactgatg atgacgtgag cagcggctcc
tccagtgaaa ggagcagcac ttcaggaggt tacatctttt acacctttt tactgtacac cccatcccag
acgaagacag tcctggatc accgacagca cagacagaat ccctgctacc agagaccaag acacattcca
ccccagtggg gggtcccata ccactcatgg atctgaatca gatggacact cacatgggag tcaagaaggt
ggagcaaaca caacctctgg tcctataagg acaccccaaa ttccagaatg ctgatcatc ttggcatccc
tcttggcctt ggctttgatt cttgcagttt gcattgcagt caacagtcga agaaggtgtg ggcagaagaa
aaagctagtg atcaacagtg gcaatggagc tgtggaggac agaaagccaa gtggactcaa cggagaggcc
agcaagtctc aggaaatgct gcatttggtg aacaaggagt cgtcagaaac tccagaccag tttatgacag
ctgatgagac aaggaacctg cagaatgtga acatgaagat tgggtgtaa cacctacacc attatcttgg
aaagaaacaa ccgttggaaa cataaccatt acagggagct gggacactta acagatgcaa tgtgctactg
attgtttcat tgcgaatctt ttttagcata aaattttcta ctctttttgt tttttgtgtt ttgttctta
aagtcaggtc caatttgtaa aaacagcatt gctttctgaa attagggccc aattaataat cagcaagaat
ttgatcgttc cagttcccac ttggaggcct tcatccctc gggtgtgcta tggatggctt ctaacaaaaa
ctacacatat gtattcctga tcgccaacct tcccccacc agctaaggac atttcccagg gttaataggg
cctggtccct gggaggaaat ttgaatgggt ccattttgcc cttccatagc ctaatccctg ggcattgctt
tccactgagg ttgggggttg gggtgtacta gttacacatc ttcaacagac ccctctaga aattttcag
atgcttctgg gagacaccca aagggtgaag ctatttatct gtagtaaact atttatctgt gtttttgaaa
tattaaaccc tggatcagtc ctttgatcag tataattttt taaagttact ttgtcagagg cacaaagggg
tttaaactga ttcataataa atatctgtac ttcttcgatc ttcaccttt gtgctgtgat tcttcagttt
ctaaaccagc actgtctggg tcctacaat gtatcaggaa gagctgagaa tggtaaggag actcttctaa
gtcttcatct cagagaccct gagttcccac tcagacccac tcagccaaat ctcatggaag accaaggagg
gcagcactgt ttttgtttt tgttttttgt ttttttttt tgacactgtc caaaggtttt ccatcctgtc
ctggaatcag agttggaagc tgaggagctt cagcctcttt tatggtttaa tggccacctg ttctctcctg
tgaaaggctt tgcaaagtca cattaagttt gcatgacctg ttatccctgg ggccctattt catagaggct
ggccctatta gtgatttcca aaaacaatat ggaagtgcct tttgatgtct acaataaga gaagaagcca
atggaaatga aagagattgg caaaggggaa ggatgatgcc atgtagatcc tgtttgacat ttttatggct
gtatttgtaa acttaaacac accagtgtct gttcttgatg cagttgctat ttaggatgag ttaagtgcct
ggggagtccc tcaaaaggtt aaagggattc ccatcattgg aatcttatca ccagataggc aagtttatga
ccaaacaaga gagtactggc tttatcctct aacctcatat tttctcccac ttggcaagtc ctttgtggca
tttattcatc agtcaggtg tccgattggt cctagaactt ccaaaggctg cttgtcatag aagccattgc
atctataaag caacggctcc tgttaaatgg tatctccttt ctgaggctcc tactaaaagt catttgttac
ctaaacttat gtgcttaaca ggcaatgctt ctcagaccac aaagcagaaa gaagaagaaa agctcctgac
```

Figure 25

```
taaatcaggg ctgggcttag acagagttga tctgtagaat atctttaaag gagagatgtc aactttctgc
actattccca gcctctgctc ctccctgtct accctctccc ctccctctct ccctccactt caccccacaa
tcttgaaaaa cttcctttct cttctgtgaa catcattggc cagatccatt ttcagtggtc tggatttctt
tttattttct tttcaacttg aaagaaactg gacattaggc cactatgtgt tgttactgcc actagtgttc
aagtgcctct tgttttccca gagatttcct gggtctgcca gaggcccaga caggctcact caagctcttt
aactgaaaag caacaagcca ctccaggaca aggttcaaaa tggttacaac agcctctacc tgtcgcccca
gggagaaagg ggtagtgata caagtctcat agccagagat ggttttccac tccttctaga tattcccaaa
aagaggctga gacaggaggt tattttcaat tttattttgg aattaaatac ttttttccct ttattactgt
tgtagtccct cacttggata tacctctgtt ttcacgatag aaataaggga ggtctagagc ttctattcct
tggccattgt caacggagag ctggccaagt cttcacaaac ccttgcaaca ttgcctgaag tttatggaat
aagatgtatt ctcactccct tgatctcaag ggcgtaactc tggaagcaca gcttgactac acgtcatttt
taccaatgat tttcaggtga cctggctaa gtcatttaaa ctgggtcttt ataaaagtaa aaggccaaca
tttaattatt ttgcaaagca acctaagagc taaagatgta atttttcttg caattgtaaa tcttttgtgt
ctcctgaaga cttcccttaa aattagctct gagtgaaaaa tcaaaagaga caaagacat cttcgaatcc
atatttcaag cctggtagaa ttggcttttc tagcagaacc tttccaaaag ttttatattg agattcataa
caacaccaag aattgatttt gtagccaaca ttcattcaat actgttatat cagaggagta ggagagagga
aacatttgac ttatctggaa aagcaaaatg tacttaagaa taagaataac atggtccatt cacctttatg
ttatagatat gtctttgtgt aaatcatttg ttttgagttt tcaaagaata gcccattgtt cattcttgtg
ctgtacaatg accactgtta ttgttacttt gacttttcag agcacaccct tcctctggtt tttgtatatt
tattgatgga tcaataataa tgaggaaagc atgatatgta tattgctgag ttgaaagcac ttattggaaa
atattaaaag gctaacatta aaagactaaa ggaaacagaa aaaaaaaaa aaaaa
```

Figure 25 continued

CD44 (SEQ ID NO: 22)

Amino acid sequence of isoform 4:
```
MDKFWWHAAW GLCLVPLSLA QIDLNITCRF AGVFHVEKNG RYSISRTEAA DLCKAFNSTL PTMAQMEKAL
SIGFETCRYG FIEGHVVIPR IHPNSICAAN NTGVYILTSN TSQYDTYCFN ASAPPEEDCT SVTDLPNAFD
GPITITIVNR DGTRYVQKGE YRTNPEDIYP SNPTDDDVSS GSSSERSSTS GGYIFYTFST VHPIPDEDSP
WITDSTDRIP ATRDQDTFHP SGGSHTTHGS ESDGHSHGSQ EGGANTTSGP IRTPQIPEWL IILASLLALA
LILAVCIAVN SRRRCGQKKK LVINSGNGAV EDRKPSGLNG EASKSQEMVH LVNKESSETP DQFMTADETR
NLQNVDMKIG V
```

Figure 26

CD44 (SEQ ID NO: 23)

mRNA sequence of variant #5:

```
gagaagaaag ccagtgcgtc tctgggcgca ggggccagtg gggctcggag gcacaggcac cccgcgacac
tccaggttcc ccgacccacg tccctggcag ccccgattat ttacagcctc agcagagcac ggggcggggg
cagaggggcc cgcccgggag ggctgctact tcttaaaacc tctgcgggct gcttagtcac agccccctt
gcttgggtgt gtccttcgct cgctccctcc ctccgtctta ggtcactgtt ttcaacctcg aataaaaact
gcagccaact tccgaggcag cctcattgcc cagcggaccc cagcctctgc caggttcggt ccgccatcct
cgtcccgtcc tccgccggcc cctgccccgc gcccagggat cctccagctc ctttcgcccg cgcctccgt
tcgctccgga caccatggac aagttttggt ggcacgcagc ctggggactc tgcctcgtgc gctgagcct
ggcgcagatc gatttgaata taacctgccg ctttgcaggt gtattccacg tggagaaaaa tggtcgctac
agcatctctc ggacggaggc cgctgacctc tgcaaggctt caatagcac cttgcccaca atgcccaga
tggagaaagc tctgagcatc ggatttgaga cctgcagttt gcattgcagt caacagtcga agaaggtgtg
ggcagaagaa aaagctagtg atcaacagtg gcaatggagc tgtggaggac agaaagccaa gtggactcaa
cggagaggcc agcaagtctc aggaaatggt gcatttggtg aacaaggagt cgtcagaaac tccagaccag
tttatgacag ctgatgagac aaggaacctg cagaatgtgg acatgaagat tgggtgtaa cacctacacc
attatcttgg aaagaaacaa ccgttggaaa cataaccatt acagggagct gggacactta acagatgcaa
tgtgctactg attgtttcat tgcgaatctt ttttagcata aaattttcta ctcttttgt tttttgtgtt
ttgttcttta aagtcaggtc caatttgtaa aaacagcatt gctttctgaa attagggccc aattaataat
cagcaagaat ttgatcgttc cagttcccac ttggaggcct tcatccctc gggtgtgcta tggatggctt
ctaacaaaaa ctacacatat gtattcctga tcgccaacct ttcccccacc agctaaggac atttcccagg
gttaataggg cctggtccct gggaggaaat ttgaatgggt ccattttgcc cttccatagc ctaatccctg
ggcattgctt tccactgagg ttgggggttg gggtgtacta gttacacatc ttcaacagac cccctctaga
aattttttcag atgcttctgg gagacaccca aagggtgaag ctatttatct gtagtaaact atttatctgt
gttttgaaa tattaaaccc tggatcagtc ctttgatcag tataattttt taaagttact ttgtcagagg
cacaaaaggg tttaaactga ttcataataa atatctgtac ttcttcgatc ttcacctttt gtgctgtgat
tcttcagttt ctaaaccagc actgtctggg tccctacaat gtatcaggaa gagctgagaa tggtaaggag
actcttctaa gtcttcatct cagagaccct gagttcccac tcagacccac tcagccaaat ctcatggaag
accaaggagg gcagcactgt ttttgttttt tgttttttgt tttttttttt tgacactgtc caaaggtttt
ccatcctgtc ctggaatcag agttggaagc tgaggagctt cagcctcttt tatggtttaa tggccacctg
ttctctcctg tgaaaggctt tgcaaagtca cattaagttt gcatgacctg ttatccctgg ggccctattt
catagaggct ggccctatta gtgatttcca aaaacaatat ggaagtgcct tttgatgtct tacaataaga
gaagaagcca atggaaatga aagagattgg caaggggaa ggatgatgcc atgtagatcc tgtttgacat
ttttatggct gtatttgtaa acttaaacac accagtgtct gttcttgatg cagttgctat ttaggatgag
ttaagtgcct ggggagtccc tcaaaaggtt aaagggattc ccatcattgg aatcttatca ccagataggc
aagtttatga ccaaacaaga gagtactggc tttatcctct aacctcatat tttctcccac ttggcaagtc
ctttgtggca tttattcatc agtcagggtg tccgattggt cctagaactt ccaaaggctg cttgtcatag
aagccattgc atctataaag caacggctcc tgttaaatgg tatctccttt ctgaggctcc tactaaaagt
catttgttac ctaaacttat gtgcttaaca ggcaatgctt ctcagaccac aaagcagaaa gaagaagaaa
agctcctgac taaatcaggg ctgggcttag acagagttga tctgtagaat atctttaaag gagagatgtc
aactttctgc actattccca gcctctgctc ctccctgtct accctctccc ctccctctct ccctccactt
caccccacaa tcttgaaaaa cttccttct cttctgtgaa catcattggc cagatccatt ttcagtggtc
tggatttctt tttattttct tttcaacttg aaagaaactg acattaggc cactatgtgt tgttactgcc
actagtgttc aagtgcctct tgttttccca gagatttcct gggtctgcca gaggcccaga caggctcact
caagctcttt aactgaaaag caacaagcca ctccaggaca aggttcaaaa tggttacaac agcctctacc
tgtcgcccca gggagaaagg ggtagtgata caagtctcat agccagagat ggttttccac tccttctaga
tattcccaaa aagaggctga gacaggaggt tattttcaat tttattttgg aattaaatac ttttttccct
ttattactgt tgtagtccct cacttggata tacctctgtt tcacgatag aaataaggga ggtctagagc
ttctattcct tggccattgt caacggagag ctggccaagt cttcacaaac ccttgcaaca ttgcctgaag
```

Figure 27

```
tttatggaat aagatgtatt ctcactccct tgatctcaag ggcgtaactc tggaagcaca gcttgactac
acgtcatttt taccaatgat tttcaggtga cctgggctaa gtcatttaaa ctgggtcttt ataaaagtaa
aaggccaaca tttaattatt ttgcaaagca acctaagagc taaagatgta atttttcttg caattgtaaa
tcttttgtgt ctcctgaaga cttcccttaa aattagctct gagtgaaaaa tcaaaagaga caaaagacat
cttcgaatcc atatttcaag cctggtagaa ttggcttttc tagcagaacc tttccaaaag ttttatattg
agattcataa caacaccaag aattgatttt gtagccaaca ttcattcaat actgttatat cagaggagta
ggagagagga aacatttgac ttatctggaa aagcaaaatg tacttaagaa taagaataac atggtccatt
caccttatg ttatagatat gtctttgtgt aaatcatttg ttttgagttt tcaaagaata gcccattgtt
cattcttgtg ctgtacaatg accactgtta ttgttacttt gacttttcag agcacaccct tcctctggtt
tttgtatatt tattgatgga tcaataataa tgaggaaagc atgatatgta tattgctgag ttgaaagcac
ttattggaaa atattaaaag gctaacatta aagactaaa ggaaacagaa aaaaaaaaaa aaaaa
```

Figure 27 continued

CD44 (SEQ ID NO: 24)

Amino acid sequence of isoform 5:
```
MDKFWWHAAW GLCLVPLSLA QIDLNITCRF AGVFHVEKNG RYSISRTEAA DLCKAFNSTL PTMAQMEKAL
SIGFETCSLH CSQQSKKVWA EEKASDQQWQ WSCGGQKAKW TQRRGQQVSG NGAFGEQGVV RNSRPVYDS
```

Figure 28

Frizzled-1 (SEQ ID NO: 25)

mRNA sequence:
```
agttgaggga ttgacacaaa tggtcaggcg gcggcggcgg agaaggaggc ggaggcgcag gggggagccg
agcccgctgg gctgcggaga gttgcgctct ctacggggcc gcggccacta gcgcggcgcc gccagccggg
agccagcgag ccgagggcca ggaaggcggg acacgacccc ggcgcgccct agccacccgg gttctccccg
ccgcccgcgc ttcatgaatc gcaagtttcc gcggcggcgg cggctgcggt acgcagaaca ggagccgggg
gagcgggccg aaagcggctt gggctcgacg gagggcaccc gcgcagaggt ctccctggcc gcaggggag
ccgccgccgg ccgtgcccct gcagccccca gcggagcggc gccaagagag gagccgagaa agtatggctg
aggaggaggc gcctaagaag tcccgggccg ccggcggtgg cgcgagctgg aactttgtg ccggggcgct
ctcggcccgg ctggcggagg agggcagcgg ggacgccggt ggccgccgcc gcccgccagt tgaccccgg
cgattggcgc gccagctgct gctgctgctt tggctgctgg aggctccgct gctgctgggg gtccgggccc
aggcggcggg ccaggggcca ggccaggggc ccgggccggg gcagcaaccg ccgccgccgc ctcagcagca
acagacgcgg cagcagtaca acggcgagcg gggcatctcc gtcccggacc acggctattg ccagcccatc
tccatcccgc tgtgcacgga catcgctac aaccagacca tcatgcccaa cctgctgggc cacacgaacc
aggaggacgc gggcctggag gtgcaccagt tctaccctct agtgaaagtg cagtgttccg ctgagctcaa
gttcttcctg tgctccatgt acgcgcccgt gtgcaccgtg ctagagcagg cgctgccgcc ctgccgctcc
ctgtgcgagc gcgcgcgcca gggctgcgag gcgctcatga caagttcgg cttccagtgg ccagacacgc
tcaagtgtga gaagttcccg gtgcacggcg ccggcgagct gtgcgtgggc cagaacacgt ccgacaaggg
caccccgacg ccctcgctgc ttccagagtt ctggaccagc aaccctcagc acggcggcgg agggcaccgt
ggcggcttcc cgggggcgc cggcgcgtcg gagcgaggca gttctcctg cccgcgcgcc ctcaaggtgc
cctcctacct caactaccac ttcctggggg agaaggactg cggcgcacct tgtgagccga ccaaggtgta
tgggctcatg tacttcgggc ccgaggagct gcgcttctcg cgcacctgga ttggcatttg tcagtgctg
tgctgcgcct ccacgctctt cacggtgctt acgtacctgg tggacatgcg gcgcttcagc tacccggagc
ggcccatcat cttcttgtcc ggctgttaca cggccgtggc cgtggcctac atcgccggct cctcctgga
agaccgagtg gtgtgtaatg acaagttcgc cgaggacggg gcacgcactg tggcgcaggg caccaagaag
gagggctgca ccatcctctt catgatgctc tacttcttca gcatgccag ctccatctgg tgggtgatcc
tgtcgctcac ctggttcctg gcggctggca tgaagtgggg ccacgaggcc atcgaagcca actcacagta
ttttcacctg gccgcctggg ctgtgccggc catcaagacc atcaccatcc tggcgctggg ccaggtggac
ggcgatgtgc tgagcggagt gtgcttcgtg gggcttaaca acgtggacgc gctgcgtggc ttcgtgctgg
cgcccctctt cgtgtacctg tttatcggca cgtcctttct gctggccggc tttgtgtcgc tcttccgcat
ccgcaccatc atgaagcacg atggcaccaa gaccgagaag ctggagaagc tcatggtgcg cattggcgtc
ttcagcgtgc tgtacactgt gccagccacc atcgtcatcg cctgctactt ctacgagcag gccttccggg
accagtggga acgcagctgg gtgcccagga gctgcaagag ctacgctatc ccctgccctc acctccaggc
gggcggaggc gccccgccgc acccgcccat gagcccggac ttcacggtct tcatgattaa gtaccttatg
acgctgatcg tgggcatcac gtcgggcttc tggatctggt ccggcaagac cctcaactcc tggaggaagt
tctacacgag gctcaccaac agcaaacaag gggagactac agtctgagac ccggggctca gcccatgccc
aggcctcggc cggggcgcag cgatccccca aagccagcgc cgtggagttc gtgccaatcc tgacatctcg
aggtttcctc actagacaac tctctttcgc aggctccttt gaacaactca gctcctgcaa aagcttccgt
ccctgaggca aaaggacacg agggcccgac tgccagaggg aggatggaca gacctcttgc cctcacactc
tggtaccagg actgttcgct tttatgattg taaatagcct gtgtaagatt tttgtaagta tatttgtatt
taaatgacga ccgatcacgc gttttctttt tcaaaagtt tttaattatt tagggcggtt taaccatttg
aggcttttcc ttcttgccct tttcggagta ttgcaaagga gctaaaactg gtgtgcaacc gcacagcgct
cctggtcgtc ctcgcgcgcc tctccctacc acgggtgctc gggacggctg ggcgccagct ccggggcgag
ttcagcactg cggggtgcga ctagggctgc gctgccaggg tcacttcccg cctcctcctt ttgccccctc
cccctccttc tgtcccctcc ctttctttcc tggcttgagg tagggctct taaggtacag aactccacaa
accttccaaa tctgaggag ggcccccata cattacaatt cctcccttgc tcggcggtgg attgcgaagg
cccgtccctt cgacttcctg aagctggatt tttaactgtc cagaactttc ctccaacttc atggggccc
acgggtgtgg gcgctggcag tctcagcctc cctccacggt caccttcaac gcccagacac tccttctcc
caccttagtt ggttacaggg tgagtgagat aaccaatgcc aaacttttgt aagtctaatt tttgagggt
```

Figure 29

```
gagctcattt cattctctag tgtctaaaac ctggtatggg tttggccagc gtcatggaaa gatgtggtta
ctgagatttg ggaagaagca tgaagctttg tgtgggttgg aagagactga agatatgggt tataaaatgt
taattctaat tgcatacgga tgcctggcaa ccttgccttt gagaatgaga cagcctgcgc ttagatttta
ccggtctgta aaatggaaat gttgaggtca cctggaaagc tttgttaagg agttgatgtt tgctttcctt
aacaagacag caaaacgtaa acagaaattg aaaacttgaa ggatatttca gtgtcatgga cttcctcaaa
atgaagtgct attttcttat ttttaatcaa ataactagac atatatcaga aactttaaaa tgtaaaagtt
gtacactttc aacattttat tacgattatt attcagcagc acattctgag ggggaacaa ttcacaccac
caataataac ctggtaagat ttcaggaggt aaagaaggtg gaataattga cggggagata gcgcctgaaa
taaacaaaat atgggcatgc atgctaaagg gaaatgtgt gcaggtctac tgcattaaat cctgtgtgct
cctctttgg atttacagaa atgtgtcaaa tgtaaatctt tcaaagccat ttaaaaatat tcactttagt
tctctgtgaa gaagaggaga aaagcaatcc tcctgattgt attgttttaa actttaagaa tttatcaaaa
tgccggtact taggacctaa atttatctat gtctgtcata cgctaaaatg atattggtct ttgaatttgg
tatacattta ttctgttcac tatcacaaaa tcatctatat ttatagagga atagaagttt atatatatat
aataccatat ttttaatttc acaaataaaa aattcaaagt tttgtacaaa attatatgga ttttgtgcct
gaaaataata gagcttgagc tgtctgaact attttacatt ttatggtgtc tcatagccaa tcccacagtg
taaaaattca
```

Figure 29 continued

Frizzled-1 (SEQ ID NO: 26)

Amino acid sequence:
```
MAEEEAPKKS RAAGGGASWE LCAGALSARL AEEGSGDAGG RRRPPVDPRR LARQLLLLLW LLEAPLLLGV
RAQAAGQGPG QGPGPGQQPP PPPQQQQSGQ QYNGERGISV PDHGYCQPIS IPLCTDIAYN QTIMPNLLGH
TNQEDAGLEV HQFYPLVKVQ CSAELKFFLC SMYAPVCTVL EQALPPCRSL CERARQGCEA LMNKFGFQWP
DTLKCEKFPV HGAGELCVGQ NTSDKGTPTP SLLPEFWTSN PQHGGGHRG GFPGGAGASE RGKFSCPRAL
KVPSYLNYHF LGEKDCGAPC EPTKVYGLMY FGPEELRFSR TWIGIWSVLC CASTLFTVLT YLVDMRRFSY
PERPIIFLSG CYTAVAVAYI AGFLLEDRVV CNDKFAEDGA RTVAQGTKKE GCTILFMMLY FFSMASSIWW
VILSLTWFLA AGMKWGHEAI EANSQYFHLA AWAVPAIKTI TILALGQVDG DVLSGVCFVG LNNVDALRGF
VLAPLFVYLF IGTSFLLAGF VSLFRIRTIM KHDGTKTEKL EKLMVRIGVF SVLYTVPATI VIACYFYEQA
FRDQWERSWV AQSCKSYAIP CPHLQAGGGA PPHPPMSPDF TVFMIKYLMT LIVGITSGFW IWSGKTLNSW
RKFYTRLTNS KQGETTV
```

Figure 30

CITED1 (SEQ ID NO: 27)

mRNA sequence:
```
gtggaaattg aggggagaaa aaaaaaggga aaaaaagggt ctgtccttcc tgggattcct agccgaggcc
agtctgctgc cgtgtgcgtg tgcgtcaggg ctctccgggc ggcaatgggg gcttgagagc cgggtcccca
gcgccgggaa gggagcgcgg tggccgccac cgccaccgcc ccggagtccg gcgccgaagc tgcgggcggg
cgggcgggca ccagctcggt caggggctgc ttggcgcggc actgtgcggt gcagcggcgg cgcggcgcgg
tgcgggcttt tcccaggcgc cccggggtcg ggtggccaac ggcgcggccg cgggcgctga gcgcgaccgg
ttcgcggtag cggtggcggc ggcgtgcgtg ccaggggctg ggggctccgc cgcctctctt gcggctcacc
gagctccgcg cttccctctc tccagggcag gcggcttctc agagcacaac agctccagct ggcagcatca
cttcccgcca atttatccaa cttctgccaa ggctctgaaa tgccaacaac gtcgaggcct gcacttgatg
tcaagggtgg cacctcacct gcgaaggagg atgccaacca agagatgagc tccgtggcct actccaacct
tgcggtgaaa gatcgcaaag cagtggccat tctgcactac cctggggtag cctcaaatgg aaccaaggcc
agtgggctc ccactagttc ctcgggatct ccaataggct ctcctacaac caccctccc actaaacccc
catccttcaa cctgcacccc gcccctcact tgctggctag tatgcagctg cagaaactta atagccagta
tcagggatg gctgctgcca ctccaggcca acccggggag gcaggacccc tgcaaaactg ggactttggg
gcccaggcgg gaggggcaga atcactctct ccttctgctg gtgcccagag ccctgctatc atcgattcgg
acccagtgga tgaggaagtg ctgatgtcgc tggtggtgga actggggttg gaccgagcca atgagcttcc
ggagctgtgg ctggggcaga atgagtttga cttcactgcg gactttccat ctagctgcta atgccaagtg
tccctaaaga tggaggaata aagccaccaa ttctgttgta aataaaaata agttactta caaaaaaaaa
aaaaaaaaa aaa
```

Figure 31

CITED1 (SEQ ID NO: 28)

Amino acid sequence:
```
MPTTSRPALD VKGGTSPAKE DANQEMSSVA YSNLAVKDRK AVAILHYPGV ASNGTKASGA PTSSSGSPIG
SPTTTPPTKP PSFNLHPAPH LLASMQLQKL NSQYQGMAAA TPGQPGEAGP LQNWDFGAQA GGAESLSPSA
GAQSPAIIDS DPVDEEVLMS LVVELGLDRA NELPELWLGQ NEFDFTADFP SSC
```

Figure 32

ARHI (SEQ ID NO: 29)

mRNA sequence:

```
gctctgcgtt gggccagccc ctcacagctg gtttcttacc acgtattgcg caagcggaat ctatgcctgt
tacccacact ccctgcgccc ccgcaccccg ctcctgtgcg caagtcggaa tataaaaccg cggaggagtg
agctcttggg gtgtccagtt ggttgccgcg gcagtctctc cgagcagcgc atttgtcttc taggctgctt
ggttcgtgcc tccgagaaag gggtctcctg ctgccagcta agtgtgggag aacttgtgca cgtatctccc
ctccgaatcc aacgatggg taacgccagc tttggctcca aggaacagaa gctgctgaag cggttgcggc
ttctgcccgc cctgcttatc ctccgcgcct tcaagcccca caggaagatc agagattacc gcgtcgtggt
agtcggcacc gctggtgtgg ggaaaagtac gctgctgcac aagtgggcga gcggcaactt ccgtcatgag
tacctgccga ccattgaaaa tacctactgc cagttgctgg gctgcagcca cggtgtgctt tccctgcaca
tcaccgacag caagagtggc gacggcaacc cgctctgca cgccacgtt atagcccggg gccacgcctt
cgtcctggtc tactcagtca ccaagaagga aaccctggaa gagctgaagg ccttctatga gctgatctgc
aagatcaaag gtaacaacct gcataagttc cccatcgtgc tggtgggcaa taaaagtgat gacacccacc
gggaggtggc cctgaatgat ggtgccacct gtgcgatgga gtggaattgc gccttcatgg agatttcagc
caagaccgat gtgaatgtgc aggagctgtt ccacatgctg ctgaattaca gaaaaagcc caccaccggc
ctccaggagc ccgagaagaa atcccagatg cccaacacca ctgagaagct gcttgacaag tgcataatca
tgtgagccct gggccttaag agccagctct tcctatcctg tagcgtgtag aaaacgtgga ctcatttcac
tatgttacat gtacatggtt gatttgtgc tgttgtttgg actgtaacat ccatgttgtc aatacgtata
ccttgtaagt ggataacttt tctttttccc aggccagaga attcaaattg ttaaaacatt ggcatttgaa
gaggagaaca aaatgtagca tgatgtattt aaagtaaggc ctttagtaat gaatgtaatg agagaaaatg
ttttgaaaag aacaaaacat caaaatgaat agaaagaaaa attggaaggc gtccttttgg taacccgatt
attgtgtatt accttttaaat atttcacatc ctgtaagtgc ttaatcatat cttttaattg tgtatttaag
aaaagtgttt tcacaacaaa gcttttgat aaattgctgc gtgacatata ctaaataaaa aaatgaatat
gttgatcatt aggggtgtgg gagcagagaa aattgtgaaa gtgactctca ctaaagatgt tagtagtttc
tcatgtcatt taaaaatgtt tgagtattct gcatagcagt ttgtaaaagt gtaacagctt attgacttaa
taaagctttt cctgcatgca aaaaaaaaa aa
```

Figure 33

ARHI (SEQ ID NO: 30)

Amino acid sequence:
```
MGNASFGSKE QKLLKRLRLL PALLILRAFK PHRKIRDYRV VVVGTAGVGK STLLHKWASG NFRHEYLPTI
ENTYCQLLGC SHGVLSLHIT DSKSGDGNRA LQRHVIARGH AFVLVYSVTK KETLEELKAF YELICKIKGN
NLHKFPIVLV GNKSDDTHRE VALNDGATCA MEWNCAFMEI SAKTDVNVQE LFHMLLNYKK KPTTGLQEPE
KKSQMPNTTE KLLDKCIIM
```

Figure 34

Primer sets:

Glyceraldehyde-3-phosphate dehydrogenase
5'-GGGCTGCTTTTAACTCTGGTAA-3' (SEQ ID NO: 31)
5'-ATGGGTGGAATCATATTGGAAC-3' (SEQ ID NO: 32)

β-actin
5'-CGTCATACTCCTGCTTGCTG-3' (SEQ ID NO: 33)
5'-CCAGATCATTGCTCCTCCTGA-3' (SEQ ID NO: 34)

CCND2
5'-CACTTGTGATGCCCTGACTG-3' (SEQ ID NO: 35)
5'-ACGGTACTGCTGCAGGCTAT-3' (SEQ ID NO: 36)

PLAB
5'-CAACCAGAGCTGGGAAGATT-3' (SEQ ID NO: 37)
5'-AGAGATACGCAGGTGCAGGT-3' (SEQ ID NO: 38)

PCSK2
5'-GCCATGGTGAAAATGGCTAA-3' (SEQ ID NO: 39)
5'-GAGTGTCAGCACCAACTTGC-3' (SEQ ID NO: 40)

Figure 35

SEQUENCE LISTING

```
<160> NUMBER OF SEQ ID NOS: 40

<210> SEQ ID NO 1
<211> LENGTH: 6480
<212> TYPE: DNA
<213> ORGANISM: Homo sapiens

<400> SEQUENCE: 1
agagcgagca ggggagagcg agaccagttt taaggggagg accggtgcga gtgaggcagc        60
cccgaggctc tgctcgccca ccacccaatc ctcgcctccc ttctgctcca ccttctctct       120
ctgccctcac ctctccccg aaaaccccct atttagccaa aggaaggagg tcagggaac         180 gctctcccct ccccttccaa aaaacaaaaa cagaaaaacc cttttccagg ccggggaaag       240
caggagggag aggggccgcc gggctggcca tggagctgct gtgccacgag gtggacccgg       300
tccgcagggc cgtgcgggac cgcaacctgc tccgagacga ccgcgtcctg cagaacctgc       360
tcaccatcga ggagcgctac cttccgcagt gctcctactt caagtgcgtg cagaaggaca       420
tccaacccta catgcgcaga atggtggcca cctggatgct ggaggtctgt gaggaacaga       480
```

```
agtgcgaaga agaggtcttc cctctggcca tgaattacct ggaccgtttc ttggctgggg      540
tcccgactcc gaagtcccat ctgcaactcc tgggtgctgt ctgcatgttc ctggcctcca      600
aactcaaaga gaccagcccg ctgaccgcgg agaagctgtg catttacacc gacaactcca      660
tcaagcctca ggagctgctg gagtgggaac tggtggtgct ggggaagttg aagtggaacc      720
tggcagctgt cactcctcat gacttcattg agcacatctt gcgcaagctg ccccagcagc      780
gggagaagct gtctctgatc cgcaagcatg ctcagacctt cattgctctg tgtgccaccg      840
actttaagtt tgccatgtac ccaccgtcga tgatcgcaac tggaagtgtg ggagcagcca      900
tctgtgggct ccagcaggat gaggaagtga gctcgctcac ttgtgatgcc ctgactgagc      960
tgctggctaa gatcaccaac acagacgtgg attgtctcaa agcttgccag gagcagattg     1020
aggcggtgct cctcaatagc ctgcagcagt accgtcagga ccaacgtgac ggatccaagt     1080
cggaggatga actggaccaa gccagcaccc ctacagacgt gcgggatatc gacctgtgag     1140
gatgccagtt gggccgaaag agagagacgc gtccataatc tggtctcttc ttctttctgg     1200 ttgttttttgt tctttgtgtt ttagggtgaa acttaaaaaa aaaattctgc ccccacctag     1260
atcatattta aagatctttt agaagtgaga gaaaaaggtc ctacgaaaac ggaataataa     1320
aaagcatttg gtgcctattt gaagtacagc ataagggaat cccttgtata tgcgaacagt     1380
tattgtttga ttatgtaaaa gtaatagtaa aatgcttaca ggaaaacctg cagagtagtt     1440
agagaatatg tatgcctgca atatgggaac aaattagagg agactttttt ttttcatgtt     1500
atgagctagc acatacaccc ccttgtagta taatttcaag gaactgtgta cgccatttat     1560
ggcatgatta gattgcaaag caatgaactc aagaaggaat tgaaataagg agggacatga     1620
tggggaagga gtacaaaaca atctctcaac atgattgaac catttgggat ggagaagcac     1680
ctttgctctc agccacctgt tactaagtca ggagtgtagt tggatctcta cattaatgtc     1740
ctcttgctgt ctacagtagc tgctacctaa aaaaagatgt tttattttgc cagttggaca     1800
caggtgattg gctcctgggt ttcatgttct gtgacatcct gcttcttctt ccaaatgcag     1860
ttcattgcag acaccaccat attgctatct aatggggaaa tgtagctatg gccataacc      1920 aaaactcaca tgaaacggag gcagatggag accaagggtg ggatccagaa tggagtctttt    1980 tctgttattg tatttaaaag ggtaatgtgg ccttggcatt tcttcttaga aaaaaactaa     2040
tttttggtgc tgattggcat gtctggttca cagtttagca ttgttataaa ccattccatt     2100
cgaaaagcac tttgaaaaat tgttcccgag cgatagatgg gatggtttat gcaagtcatg     2160
ctgaatactc ctcccctctt ctcttttgcc ccctcccttc ctgcccccag tctgggttac     2220
tcttcgcttc tggtatctgg cgttctttgg tacacagttc tggtgttcct accaggactc     2280
aagagacacc ccttcctgct gacattccca tcacaacatt cctcagacaa gcctgtaaac     2340
taaaatctgt taccattctg atggcacaga aggatcttaa ttcccatctc tatacttctc     2400
ctttggacat ggaaagaaaa gttattgctg gtgcaaagat agatggctga acatcagggt     2460
gtggcatttt gttcccttttc cgtttttttt ttttttatt gttgttgtta attttattgc     2520
aaagttgtat tcagcgtact tgaattttttc ttcctctcca cttcttagag gcattcagtt     2580
agcaaagagg ttggagcaac aacttttttt tttttttttg cacaattgta attgacaggt     2640
aatgaagcta tttgttaaaa tatttgcctt tttaagtaaa aaagaaaaat cagaacaggg     2700
ctatttgaag aattatttta tacacagatt ctgccttgtt tcatagtatg agggttgaag     2760
acggaaaaca atctaagggt ctctcatttt tttaattttg ttttgttcag tttgttttt      2820 tttttttttt gcgctgctaa gaagctaaag tcatccatcc ttattcacgt tgacagtacc     2880
```

```
tagctgtaat gtttcacaga gtgtgctgct attttataaa catttttata atatattatt    2940
ttactgctta aattccaagt cctgaagtag atggttgaga tatgagttct tcgtactgga    3000
aaagcccttc cgtagtttgt tttcttctgg tagcatattc atggttgttt ttttttttct    3060
tttttggttt tttggttttt ttttttttcct ctgatcacat tcttcaaaga cggagtattc    3120
tttacctcag gtttactgga caaaatcaat aactacaaaa ggcaatgatt cacgcttttg    3180
ttttcataat acctcacaac cgtacagttt ctgcttggga gcccattcgc atgaggaata    3240
cagaagcagt gtgagcaggg ctgactccct ctcaggtgga aggcagggcg gtctcactcc    3300
cagggacctt tttggtcatg gaggccatcg ggctcccagt tagaccctgg tatcctcatc    3360
atgatggaaa aaatacattg aaccaaggga tcctccctcc ccttcaaggc agacgttcag    3420
tacaaacatt tatgcggtag gctcagatgt cgtaatttgc acttaggtac caggtgtcag    3480
gaaacagact aaaagaatt ccaccaggct gtttggagat cctcatcttg gagcttttc     3540 aaaagcgggg cttcatctgc aaagggccct ttcatcttga agttttccc ctccgtcttt    3600 cccctcccct ggcatggaca ccttgtgttt aggatcatct ctgcaggttt cctaggtctg    3660
aatctgcgag tagatgaacc tgcagcaagc agcgtttatg gtgcttcctt ctccctcctc    3720
tgtctcaaac tgcgcaggca agcactatgc aagcccaggc cctctgctga gcggtactaa    3780
acggtcgggt tttcaatcac actgaattgg caggataaga aaaataggtc agataagtat    3840
gggatgatag ttgaagggag gtgaagaggc tgcttctcta cagaggtgaa attccagatg    3900
agtcagtctc ttgggaagtg tgtttagaag ggttcaggac tttgtgagtt agcatgaccc    3960
taaaattcta ggggatttct ggtgggacaa tgggtggtga attttgaagt tttggagagg    4020
gaagtggagc agccagcaag taagctagcc agagttttct caagagccag ctttgctcag    4080
cacactctcc tgggccccaa ggagtcccac ggaatgggga agtgggaac cctggagttc     4140 ttgggaatct tggagcctaa agagaaaccg aggtgcaaat tcatttcatg gtgactgacc    4200
cttgagctta aacagaagca gcaaatgaaa gaaccggaca ataaggaag gcacaagcc     4260 tacccgactc tatttacagt ctgtaacttt ccactcttcc tgtagtcccg aggcccctgg    4320
gtccttctag cttttctctt tcccatcctt ggggccttgt gtgatgatgg gtgtggggct    4380
gccgatggga aagtcggggg ttgttaggct tttctgcctg ctcctgctta aacacaagaa    4440
ggaatcctgg atttttgccct ctccttagct cttagtctct ttggtaggag ttttgttcca    4500
gaggagctct ccccccttgga tttgaacttg ctcttttttgt tgttgttgtt ctttctcttc    4560
tttttcttac ctcccactaa aggggttcca aattatcctg gtcttttttct accttgttgt    4620 gtttctatct cgtctttact tccatctgtt tgttttttttc tccatcagtg ggggccgagt    4680
tgttccccca gcctgccaaa ttttgatcct tcccctcttt tggccaaatc ctaggggaa     4740 gaaatcctag tatgccaaaa atatatgcta agcataatta aactccatgc gggtccataa    4800
cagccaagaa gcctgcagga gaaagccaag ggcagttccc tccgcagaac accccatgcg    4860
tgctgagagg cgagctcctt gaagaagggg ctgttcttcc aggaggcctt attttgaact    4920
gcctcaggac cccactggag agcacagcat gccttactac tgggtcatcc ttggtctatg    4980
tgctctgtac tggaggctct gttctgcctc ttatcagcca ggtcagggc acacatggct    5040 taagtgacaa agccagagga gaagacaacc ctgacagcat cacgctgcat cccattgcta    5100
gcaggattgg caactcttca gacggagctg cgcttccctg cagtctagca cctctagggc    5160
ctctccagac tgtgccctgg gagctctggg actgaaaggt taagaacata aggcaggatc    5220
```

```
agatgactct ctccaagagg gcagggaat tttctctcca tgggccacag gggacagggc    5280
tgggagaaga aatagacttg caccttatgt catgtaaata attgattttc tagttcaaga    5340
agataatatt ggtagtgtgg gaattggagg taggaagggg aggaagtctg agtaagccag    5400
ttggcttcta agccaaaagg attcctcttt gtttatctct gagacagtcc aaccttgaga    5460
atagctttaa aagggaaatt aatgctgaga tgataaagtc cccttaagcc aacaaaccct    5520
ctgtagctat agaatgagtg caggtttcta ttggtgtgga ctcagagcaa tttacaagag    5580
ctgttcatgc agccatccat ttgtgcaaaa tagggtaaga agattcaaga ggatatttat    5640
tacttcctca taccacatgg cttttgatga ttctggattc taaacaaccc agaatggtca    5700
tttcaggcac aacgatacta cattcgtgtg tgtctgcttt taaacttggc tgggctatca    5760
gaccctattc tcggctcagg ttttgagaag ccatcagcaa atgtgtacgt gcatgctgta    5820
gctgcagcct gcatcccttc gcctgcagcc tactttgggg aaataaagtg ccttactgac    5880
tgtagccatt acagtatcca atgtcttttg acaggtgcct gtccttgaaa aacaaagttt    5940
ctatttttat ttttaattgg tttagttctt aactgctggc caactcttac atccccagca    6000
aatcatcggg ccattggatt ttttccatta tgttcatcac ccttatatca tgtacctcag    6060
atctctctct ctctcctctc tctcagttat atagtttctt gtcttggact ttttttttct    6120 tttcttttc tttttttttt tgctttaaaa caagtgtgat gccatatcaa gtccatgtta    6180
ttctctcaca gtgtactcta taagaggtgt gggtgtctgt ttggtcagga tgttagaaag    6240
tgctgataag tagcatgatc agtgtatgcg aaaaggtttt taggaagtat ggcaaaaatg    6300
ttgtattggc tatgatggtg acatgatata gtcagctgcc ttttaagagg tcttatctgt    6360
tcagtgttaa gtgatttaaa aaataataa cctgttttct gactagttta aagatggatt    6420
tgaaaatggt tttgaatgca attaggttat gctatttgga caataaactc accttgacct    6480
```

<210> SEQ ID NO 2
<211> LENGTH: 289
<212> TYPE: PRT
<213> ORGANISM: Homo sapiens

<400> SEQUENCE: 2

```
Met Glu Leu Leu Cys His Glu Val Asp Pro Val Arg Arg Ala Val Arg
1               5                   10                  15

Asp Arg Asn Leu Leu Arg Asp Arg Val Leu Gln Asn Leu Leu Thr
            20                  25                  30

Ile Glu Glu Arg Tyr Leu Pro Gln Cys Ser Tyr Phe Lys Cys Val Gln
        35                  40                  45

Lys Asp Ile Gln Pro Tyr Met Arg Arg Met Val Ala Thr Trp Met Leu
    50                  55                  60

Glu Val Cys Glu Glu Gln Lys Cys Glu Glu Val Phe Pro Leu Ala
65                  70                  75                  80

Met Asn Tyr Leu Asp Arg Phe Leu Ala Gly Val Pro Thr Pro Lys Ser
                85                  90                  95

His Leu Gln Leu Leu Gly Ala Val Cys Met Phe Leu Ala Ser Lys Leu
            100                 105                 110

Lys Glu Thr Ser Pro Leu Thr Ala Glu Lys Leu Cys Ile Tyr Thr Asp
        115                 120                 125

Asn Ser Ile Lys Pro Gln Glu Leu Leu Glu Trp Glu Leu Val Val Leu
    130                 135                 140

Gly Lys Leu Lys Trp Asn Leu Ala Ala Val Thr Pro His Asp Phe Ile
145                 150                 155                 160
```

```
Glu His Ile Leu Arg Lys Leu Pro Gln Gln Arg Glu Lys Leu Ser Leu
                165                 170                 175
Ile Arg Lys His Ala Gln Thr Phe Ile Ala Leu Cys Ala Thr Asp Phe
            180                 185                 190
Lys Phe Ala Met Tyr Pro Pro Ser Met Ile Ala Thr Gly Ser Val Gly
        195                 200                 205
Ala Ala Ile Cys Gly Leu Gln Gln Asp Glu Glu Val Ser Ser Leu Thr
    210                 215                 220
Cys Asp Ala Leu Thr Glu Leu Leu Ala Lys Ile Thr Asn Thr Asp Val
225                 230                 235                 240
Asp Cys Leu Lys Ala Cys Gln Glu Gln Ile Glu Ala Val Leu Leu Asn
                245                 250                 255
Ser Leu Gln Gln Tyr Arg Gln Asp Gln Arg Asp Gly Ser Lys Ser Glu
            260                 265                 270
Asp Glu Leu Asp Gln Ala Ser Thr Pro Thr Asp Val Arg Asp Ile Asp
        275                 280                 285
Leu

<210> SEQ ID NO 3
<211> LENGTH: 4745
<212> TYPE: DNA
<213> ORGANISM: Homo sapiens

<400> SEQUENCE: 3
gagctgagga ggagctgaaa atgcagattt agcatcaagc acagacctac actcgctctt      60
tctctccggt acacacagct ccccacattc gcacccctgc ccgcgcgccg ggccgcctga     120
ctgcacggct tccccctccag ccagatgctg agaacacac actgattcgc tgctttccaa     180
gaccctgttc agtctctttc tctatacaaa gatttttta aaaactatat ataagaattc     240
tttatttgca ccctccctcc gagtcccctg ctccgccagc ctgcgcgcct cctagcacca     300
cttttcactc ccaaagaagg atgaagggtg gttgtgtctc ccagtggaag gcggccgccg     360
ggttcctctt ctgtgtcatg gtttttgcat ctgctgagcg accggtcttc acgaatcatt     420
ttcttgtgga gttgcataaa gggggagagg acaaagctcg ccaagttgca gcagaacacg     480
gctttggagt ccgaaagctt cccttttgctg aaggtctgta ccactttttat cacaatggcc     540
ttgcaaaggc caagagaaga cgcagcctac accacaagca gcagctggag agagacccca     600
gggtaaagat ggctttgcag caggaaggat ttgaccgaaa aaagcgaggt tacagagaca     660
tcaatgagat cgacatcaac atgaacgatc ctcttttttac aaagcagtgg tatctgatca     720
atactgggca agctgatggc actcctggcc ttgatttgaa tgtggctgaa gcctgggagc     780
tgggatacac agggaaaggt gttaccattg aattatgga tgatgggatt gactatctcc     840
acccggacct ggcctccaac tataatgccg aagcaagtta cgacttcagc agcaacgacc     900
cctatcctta ccctcggtac acagatgact ggtttaacag ccacgggacc cgatgtgcag     960
gagaagtttc tgctgccgcc aacaacaata tctgtggagt tggagtagca tacaactcca    1020
aggttgcagg catccggatg ctggaccagc cattcatgac agacatcatc gaggcctcct    1080
ccatcagtca tatgccacag ctgattgaca tctacagcgc cagctgggc cccacagaca    1140
acggcaagac agtggatggg cccccgggagc tcacgctgca ggccatggcc gatggcgtga    1200
acaagggccg cggcggcaaa ggcagcatct acgtgtgggc ctccggggac ggcggcagct    1260
atgacgactg caactgcgac ggctacgcct ccagcatgtg gaccatctcc atcaactcag    1320
```

```
ccatcaacga cggcaggact gccctgtacg acgagagctg ctcttccacc ttggcttcca   1380
ccttcagcaa cgggaggaaa aggaaccccg aggccggtgt ggcaaccaca gatttgtacg   1440
gcaactgcac tctgaggcat tctgggacat ctgcagctgc ccccgaggca gctggtgtgt   1500
ttgcactggc tctggaggct aacctgggtc tgacctggcg ggacatgcag catctgactg   1560
tgctcacctc caaacggaac cagcttcacg acgaggtcca tcagtggcgg cgcaatgggg   1620
tcggcctgga atttaatcac ctctttggct acggggtcct tgatgcaggt gccatggtga   1680
aaatggctaa agactggaaa accgtgcctg agagattcca ctgtgtggga ggctccgtgc   1740
aggaccctga gaaatacca tccactggca agttggtgct gacactcaca accgacgcct    1800 gtgagggaa ggaaaatttt gtccgctacc tggagcatgt ccaggctgtc atcacggtca    1860
acgcaaccag aagaggagac ctgaacatca acatgacttc ccctatgggc accaagtcca   1920
ttttgctgag ccggcgtcca agggatgacg actccaaggt gggctttgac aagtggcctt   1980
tcatgaccac tcacacgtgg ggggaagacg cccgaggcac ctggaccctg gagctgggat   2040
ttgtcggcag cgccccgcag aagggggtgc tgaaggagtg gaccctgatg ctgcatggca   2100
ctcagagtgc cccgtacatc gaccaggtgg tgcgggatta ccagtccaag ttggccatgt   2160
ccaagaaaga ggagctggag gaagagctgg acgaagccgt ggagagaagc ctgaaaagca   2220
tccttaacaa gaactagcgc tgcacatccg ccttttccac cgccctccct ccccagctcc   2280
gcctctgtcc tcgctccacg tttcaggcag gcacctagca attccatcac ccgtacaggc   2340
aattccgtct tcttaatctg aagcttcact cactgtcaat gattattttc attacaatgg   2400
aaacaatctt ttttactcta tgccccaaat atagcgttcc caacaacatc catgtcctat   2460
gtgtgactct aaattcttta tttctgtcat tcaaatgggt gatatcctga aaaaaaaaa    2520 aaaaaaaaaa ctgggacagc tttcccctca ttttttttt tgtttctgag aaaagaacgt    2580
attttaaaag ccacatagag tgactccaag aacaattgtc catggtctca acaaggggc    2640 tgttacataa caagaaaatc aaagctgagg acagggtgtg agcgccacat ctctgaaagc   2700
acaggagaca ctgtgctata atcctttgg ggagcgatgt tttgaattta gtgagattta    2760
ccagggatgt agattaaggt gatgtgattc aaaagatgcc attcatagag agccctagtt   2820
actgcatggg gaaagagatc caggaagcat gagtgctgga tatttacta ccaatgccaa    2880 gataattcac tctactcagc cggcgtggca aatataaaac ttacagagcg tggctgtgct   2940
ctcaccagct gctgctctga gttatgttaa aatccgctag agcagcccaa attttttctca  3000 gtttgtatag agttcatccc agccccaatt ttctggggct cctcacatag ctacccaaaa   3060
gagaaaaaaa attaagacaa gcctggcaac acacctggtg aagagtagtt tactagcttt   3120
tcaaacaaga atgtcccttt tcctaagtca ctttgaggtg tctcaatctg atctgagtga   3180
gaggcgacag gagtattttt ttttttttac agctttacac acacagatgt gggctttgat   3240
ttccaagtaa tataatggaa gagaaatctc atactccccc acagtttgat gtcattaatg   3300
tgttgggaaa aaggcctctg tcccggaaga gtcatgggag gtgaaagggg cacgtttgaa   3360
gatgcgagcg ctatcttcac atagttctcc agttgtatgg agcctcttct gccaagagag   3420
ggccatgcaa ttcatcccag aggaacctga ggcctgaagg aggtgagaga agacctctgt   3480
gaggaaagca cacagtcacc ttctcggcaa ctaagcagtc cctgagacca tttaacatgc   3540
aacccgaagg ttatggtcaa tcccaaaagt caccactcca ttcccaacta gacattacca   3600
aagtgaccta cccagagatt gcttctcatc cccagtccca atgcacatcc attcccaaga   3660
aatgctttgt cttcagcctc tccaggcacc atctcccttc ctgtgggagc agagagctta   3720
```

-continued

```
gcctggagca cctttccttc aagccagcaa cacagagcac taggttcaat tccctgaagg    3780
tggccacttt aagagagaaa tctgaaaacc ccatttgctt tcttttctcc catattggca    3840
tggatttctg tcttctctaa caccttgtga ccttctctat atcatgcttt aaagtgtaat    3900
aatatgattt tttaaaagaa atttattact tgttgcaaag gtcttttaa accagtttag     3960 atttcaagaa aaataaatg gaaatcatcg aaaattcatt tcacattaat ggtctaaaaa     4020
taaaccaaag gacattatgt gtgcatgtgt gtataagtgc acacagaaat atatatacat    4080
atgtagacta tatacatgtg tgtatatatg tgtatatata catacacttg tataaatgta    4140
tatacacata tacctataat gtgtgtatgt gtatttattg aagaaacaga taccatactc    4200
atttctaaaa gaatattcag agaatatcaa gatgattctg gctgaaaaag gccagtggaa    4260
attcaggtga aaatgttcat caattcccat tgcatcacct ctgtaatttt tcagctctct    4320
gtataaacat taaatgtctt atatagcagc aaaaatataa aatagttgtc catattttca    4380
caggtgtggt gtaatttata aaattagaaa gcaacttatc agctacttaa gagaaatggc    4440
aagttttgat atgagtatac aatatataaa aatatatata gtgctatata tataaatatt    4500
tggtctctat ttcattttt gcatcagtat taatactaaa atatgtctcg ctagtgatgt     4560
ttttatgata tccctgatcc taactgaaga gacagttatt tatagtcatt tattttaaaa    4620
aatgaaaata agtgaataat aattaggtta acattgttgc tccctgtgac aaaattttat    4680
aagcaaattt caaaagacat gttgtaaatt aggaggctca acaataaaac attatgctcc    4740
agaaa                                                                4745
```

<210> SEQ ID NO 4
<211> LENGTH: 638
<212> TYPE: PRT
<213> ORGANISM: Homo sapiens

<400> SEQUENCE: 4

```
Met Lys Gly Gly Cys Val Ser Gln Trp Lys Ala Ala Gly Phe Leu
1               5                   10                  15

Phe Cys Val Met Val Phe Ala Ser Ala Glu Arg Pro Val Phe Thr Asn
                20                  25                  30

His Phe Leu Val Glu Leu His Lys Gly Gly Glu Asp Lys Ala Arg Gln
        35                  40                  45

Val Ala Ala Glu His Gly Phe Gly Val Arg Lys Leu Pro Phe Ala Glu
    50                  55                  60

Gly Leu Tyr His Phe Tyr His Asn Gly Leu Ala Lys Ala Lys Arg Arg
65                  70                  75                  80

Arg Ser Leu His His Lys Gln Gln Leu Glu Arg Asp Pro Arg Val Lys
                85                  90                  95

Met Ala Leu Gln Gln Glu Gly Phe Asp Arg Lys Lys Arg Gly Tyr Arg
                100                 105                 110

Asp Ile Asn Glu Ile Asp Ile Asn Met Asn Asp Pro Leu Phe Thr Lys
        115                 120                 125

Gln Trp Tyr Leu Ile Asn Thr Gly Gln Ala Asp Gly Thr Pro Gly Leu
    130                 135                 140

Asp Leu Asn Val Ala Glu Ala Trp Glu Leu Gly Tyr Thr Gly Lys Gly
145                 150                 155                 160

Val Thr Ile Gly Ile Met Asp Asp Gly Ile Asp Tyr Leu His Pro Asp
                165                 170                 175

Leu Ala Ser Asn Tyr Asn Ala Glu Ala Ser Tyr Asp Phe Ser Ser Asn
```

-continued

```
            180                 185                 190
Asp Pro Tyr Pro Tyr Pro Arg Tyr Thr Asp Asp Trp Phe Asn Ser His
        195                 200                 205
Gly Thr Arg Cys Ala Gly Glu Val Ser Ala Ala Asn Asn Asn Ile
    210                 215                 220
Cys Gly Val Gly Val Ala Tyr Asn Ser Lys Val Ala Gly Ile Arg Met
225                 230                 235                 240
Leu Asp Gln Pro Phe Met Thr Asp Ile Ile Glu Ala Ser Ser Ile Ser
                245                 250                 255
His Met Pro Gln Leu Ile Asp Ile Tyr Ser Ala Ser Trp Gly Pro Thr
            260                 265                 270
Asp Asn Gly Lys Thr Val Asp Gly Pro Arg Glu Leu Thr Leu Gln Ala
        275                 280                 285
Met Ala Asp Gly Val Asn Lys Gly Arg Gly Lys Gly Ser Ile Tyr
    290                 295                 300
Val Trp Ala Ser Gly Asp Gly Gly Ser Tyr Asp Asp Cys Asn Cys Asp
305                 310                 315                 320
Gly Tyr Ala Ser Ser Met Trp Thr Ile Ser Ile Asn Ser Ala Ile Asn
                325                 330                 335
Asp Gly Arg Thr Ala Leu Tyr Asp Glu Ser Cys Ser Ser Thr Leu Ala
            340                 345                 350
Ser Thr Phe Ser Asn Gly Arg Lys Arg Asn Pro Glu Ala Gly Val Ala
        355                 360                 365
Thr Thr Asp Leu Tyr Gly Asn Cys Thr Leu Arg His Ser Gly Thr Ser
    370                 375                 380
Ala Ala Ala Pro Glu Ala Ala Gly Val Phe Ala Leu Ala Leu Glu Ala
385                 390                 395                 400
Asn Leu Gly Leu Thr Trp Arg Asp Met Gln His Leu Thr Val Leu Thr
                405                 410                 415
Ser Lys Arg Asn Gln Leu His Asp Glu Val His Gln Trp Arg Arg Asn
            420                 425                 430
Gly Val Gly Leu Glu Phe Asn His Leu Phe Gly Tyr Gly Val Leu Asp
        435                 440                 445
Ala Gly Ala Met Val Lys Met Ala Lys Asp Trp Lys Thr Val Pro Glu
    450                 455                 460
Arg Phe His Cys Val Gly Gly Ser Val Gln Asp Pro Glu Lys Ile Pro
465                 470                 475                 480
Ser Thr Gly Lys Leu Val Leu Thr Leu Thr Thr Asp Ala Cys Glu Gly
                485                 490                 495
Lys Glu Asn Phe Val Arg Tyr Leu Glu His Val Gln Ala Val Ile Thr
            500                 505                 510
Val Asn Ala Thr Arg Arg Gly Asp Leu Asn Ile Asn Met Thr Ser Pro
        515                 520                 525
Met Gly Thr Lys Ser Ile Leu Leu Ser Arg Arg Pro Arg Asp Asp Asp
    530                 535                 540
Ser Lys Val Gly Phe Asp Lys Trp Pro Phe Met Thr Thr His Thr Trp
545                 550                 555                 560
Gly Glu Asp Ala Arg Gly Thr Trp Thr Leu Glu Leu Gly Phe Val Gly
                565                 570                 575
Ser Ala Pro Gln Lys Gly Val Leu Lys Glu Trp Thr Leu Met Leu His
            580                 585                 590
Gly Thr Gln Ser Ala Pro Tyr Ile Asp Gln Val Val Arg Asp Tyr Gln
        595                 600                 605
```

-continued

Ser Lys Leu Ala Met Ser Lys Lys Glu Glu Leu Glu Glu Glu Leu Asp
        610                 615                 620

Glu Ala Val Glu Arg Ser Leu Lys Ser Ile Leu Asn Lys Asn
625                 630                 635

<210> SEQ ID NO 5
<211> LENGTH: 1204
<212> TYPE: DNA
<213> ORGANISM: Homo sapiens

<400> SEQUENCE: 5

```
cggaacgagg gcaacctgca cagccatgcc cgggcaagaa ctcaggacgg tgaatggctc      60
tcagatgctc ctggtgttgc tggtgctctc gtggctgccg catggggcg ccctgtctct      120
ggccgaggcg agccgcgcaa gtttcccggg accctcagag ttgcactccg aagactccag     180
attccgagag ttgcggaaac gctacgagga cctgctaacc aggctgcggg ccaaccagag     240
ctgggaagat tcgaacaccg acctcgtccc ggcccctgca gtccggatac tcacgccaga    300
agtgcggctg ggatccggcg gccacctgca cctgcgtatc tctcgggccg ccttcccga     360
ggggctcccc gaggcctccc gccttcaccg ggctctgttc cggctgtccc cgacggcgtc      420
aaggtcgtgg gacgtgacac gaccgctgcg gcgtcagctc agccttgcaa gaccccaagc     480
gcccgcgctg cacctgcgac tgtcgccgcc gccgtcgcag tcggaccaac tgctggcaga    540
atcttcgtcc gcacggcccc agctggagtt gcacttgcgg ccgcaagccc caggggggcg    600
ccgcagagcg cgtgcgcgca acgggacga ctgtccgctc gggcccgggc gttgctgccg     660
tctgcacacg gtccgcgcgt cgctggaaga cctgggctgg gccgattggg tgctgtcgcc    720
acgggaggtg caagtgacca tgtgcatcgg cgcgtgcccg agccagttcc gggcggcaaa    780
catgcacgcg cagatcaaga cgagcctgca ccgcctgaag cccgacacgg agccagcgcc    840
ctgctgcgtg cccgccagct acaatcccat ggtgctcatt caaaagaccg acaccggggt    900
gtcgctccag acctatgatg acttgttagc caaagactgc cactgcatat gagcagtcct    960
ggtccttcca ctgtgcacct gcgcggggga ggcgacctca gttgtcctgc cctgtggaat    1020
gggctcaagg ttcctgagac acccgattcc tgcccaaaca gctgtattta tataagtctg    1080
ttatttatta ttaatttatt ggggtgacct tcttggggac tcgggggctg gtctgatgga    1140
actgtgtatt tatttaaaac tctggtgata aaaataaagc tgtctgaact gttaaaaaaaa   1200
aaaa                                                                    1204
```

<210> SEQ ID NO 6
<211> LENGTH: 308
<212> TYPE: PRT
<213> ORGANISM: Homo sapiens

<400> SEQUENCE: 6

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

```
Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp Asp Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Glu Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 7
<211> LENGTH: 4015
<212> TYPE: DNA
<213> ORGANISM: Homo sapiens

<400> SEQUENCE: 7
gcagcgctgc gtcctgctgc gcacgtggga agccctggcc ccggccaccc ccgcgatgcc      60
gcgcgctccc cgctgccgag ccgtgcgctc cctgctgcgc agccactacc gcgaggtgct     120
gccgctggcc acgttcgtgc ggcgcctggg ccccagggc tggcggctgg tgcagcgcgg      180
ggacccggcg gctttccgcg cgctggtggc ccagtgcctg tgtgcgtgc cctgggacgc      240 acggccgccc ccgccgccc ctccttccg ccaggtgtcc tgcctgaagg agctggtggc      300
ccgagtgctg cagaggctgt gcgagcgcgg cgcgaagaac gtgctggcct tcggcttcgc     360
gctgctggac ggggcccgcg ggggcccccc cgaggccttc accaccagcg tgcgcagcta     420
cctgcccaac acggtgaccg acgcactgcg ggggagcggg gcgtggggc tgctgctgcg      480 ccgcgtgggc gacgacgtgc tggttcacct gctggcacgc tgcgcgctct ttgtgctggt     540
ggctcccagc tgcgcctacc agtgtgtgcg gccgccgctg taccagctcg cgctgccac      600 tcaggcccgg ccccgccac acgctagtgg accccgaagg cgtctgggat gcgaacgggc      660
ctggaaccat agcgtcaggg aggccggggt cccctgggc ctgccagccc cgggtgcgag      720
gaggcgcggg ggcagtgcca gccgaagtct gccgttgccc aagaggccca ggcgtggcgc      780
```

-continued

```
tgcccctgag ccggagcgga cgcccgttgg gcaggggtcc tgggcccacc cgggcaggac    840
gcgtggaccg agtgaccgtg gtttctgtgt ggtgtcacct gccagacccg ccgaagaagc    900
cacctctttg gagggtgcgc tctctggcac gcgccactcc cacccatccg tgggccgcca    960
gcaccacgcg ggcccccat ccacatcgcg gccaccacgt ccctgggaca cgccttgtcc    1020
cccggtgtac gccgagacca agcacttcct ctactcctca ggcgacaagg agcagctgcg    1080
gccctccttc ctactcagct ctctgaggcc cagcctgact ggcgctcgga ggctcgtgga    1140
gaccatcttt ctgggttcca ggccctggat gccaggact ccccgcaggt tgccccgcct    1200
gccccagcgc tactggcaaa tgcggcccct gtttctggag ctgcttggga accacgcgca    1260
gtgcccctac ggggtgctcc tcaagacgca ctgcccgctg cgagctgcgg tcaccccagc    1320
agccggtgtc tgtgcccggg agaagcccca gggctctgtg gcggccccg aggaggagga    1380
cacagacccc cgtcgcctgg tgcagctgct ccgccagcac agcagcccct ggcaggtgta    1440
cggcttcgtg cgggcctgcc tgcgccggct ggtgccccca ggcctctggg gctccaggca    1500
caacgaacgc cgcttcctca ggaacaccaa gaagttcatc tccctgggga agcatgccaa    1560
gctctcgctg caggagctga cgtggaagat gagcgtgcgg gactgcgctt ggctgcgcag    1620
gagcccaggg gttggctgtg ttccggccgc agagcaccgt ctgcgtgagg agatcctggc    1680
caagttcctg cactggctga tgagtgtgta cgtcgtcgag ctgctcaggt ctttcttta    1740
tgtcacggag accacgtttc aaaagaacag gctcttttc taccggaaga gtgtctggag    1800
caagttgcaa agcattggaa tcagacagca cttgaagagg gtgcagctgc gggagctgtc    1860
ggaagcagag gtcaggcagc atcgggaagc caggcccgcc ctgctgacgt ccagactccg    1920
cttcatcccc aagcctgacg ggctgcggcc gattgtgaac atggactacg tcgtgggagc    1980
cagaacgttc cgcagagaaa agagggccga gcgtctcacc tcgagggtga aggcactgtt    2040
cagcgtgctc aactacgagc gggcgcggcg ccccggcctc ctgggcgcct ctgtgctggg    2100
cctggacgat atccacaggg cctggcgcac cttcgtgctg cgtgtgcggg cccaggaccc    2160
gccgcctgag ctgtactttg tcaaggtgga tgtgacgggc gcgtacgaca ccatccccca    2220
ggacaggctc acggaggtca tcgccagcat catcaaaccc cagaacacgt actgcgtgcg    2280
tcggtatgcc gtggtccaga aggccgccca tgggcacgtc cgcaaggcct tcaagagcca    2340
cgtctctacc ttgacagacc tccagccgta catgcgacag ttcgtggctc acctgcagga    2400
gaccagcccg ctgagggatg ccgtcgtcat cgagcagagc tcctccctga atgaggccag    2460
cagtggcctc ttcgacgtct tcctacgctt catgtgccac acgccgtgc gcatcagggg    2520
caagtcctac gtccagtgcc aggggatccc gcagggctcc atcctctcca cgctgctctg    2580
cagcctgtgc tacggcgaca tggagaacaa gctgtttgcg gggattcggc gggacgggct    2640
gctcctgcgt ttggtggatg atttcttgtt ggtgacacct cacctcaccc acgcgaaaac    2700
cttcctcagg accctggtcc gaggtgtccc tgagtatggc tgcgtggtga acttgcggaa    2760
gacagtggtg aacttccctg tagaagacga ggccctgggt ggcacggctt ttgttcagat    2820
gccggcccac ggcctattcc cctggtgcgg cctgctgctg gatacccgga ccctggaggt    2880
gcagagcgac tactccagct atgcccggac ctccatcaga gccagtctca ccttcaaccg    2940
cggcttcaag gctgggagga acatgcgtcg caaactcttt ggggtcttgc ggctgaagtg    3000
tcacagcctg tttctggatt tgcaggtgaa cagcctccag acggtgtgca ccaacatcta    3060
caagatcctc ctgctgcagg cgtacaggtt tcacgcatgt gtgctgcagc tcccatttca    3120
```

-continued

```
tcagcaagtt tggaagaacc ccacattttt cctgcgcgtc atctctgaca cggcctccct    3180
ctgctactcc atcctgaaag ccaagaacgc agggatgtcg ctgggggcca agggcgccgc    3240
cggccctctg ccctccgagg ccgtgcagtg gctgtgccac caagcattcc tgctcaagct    3300
gactcgacac cgtgtcacct acgtgccact cctggggtca tcaggacag  cccagacgca    3360
gctgagtcgg aagctcccgg ggacgacgct gactgccctg gaggccgcag ccaacccggc    3420
actgccctca gacttcaaga ccatcctgga ctgatggcca cccgcccaca gccaggccga    3480
gagcagacac cagcagccct gtcacgccgg gctctacgtc caggagggg aggggcggcc     3540
cacacccagg cccgcaccgc tgggagtctg aggcctgagt gagtgtttgg ccgaggcctg    3600
catgtccggc tgaaggctga gtgtccggct gaggcctgag cgagtgtcca gccaagggct    3660
gagtgtccag cacacctgcc gtcttcactt ccccacaggc tggcgctcgg ctccacccca    3720
gggccagctt ttcctcacca ggagcccggc ttccactccc cacataggaa tagtccatcc    3780
ccagattcgc cattgttcac ccctcgccct gccctccttt gccttccacc ccaccatcc    3840
aggtggagac cctgagaagg accctgggag ctctgggaat ttggagtgac caaaggtgtg    3900
ccctgtacac aggcgaggac cctgcacctg atgggggtc cctgtgggtc aaattggggg    3960
gaggtgctgt gggagtaaaa tactgaatat atgagttttt cagttttgaa aaaaa        4015
```

<210> SEQ ID NO 8
<211> LENGTH: 1132
<212> TYPE: PRT
<213> ORGANISM: Homo sapiens

<400> SEQUENCE: 8

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220
```

```
Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
            245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Ser Ser Leu Arg Pro
                340                 345                 350

Ser Leu Thr Gly Ala Arg Arg Leu Val Glu Thr Ile Phe Leu Gly Ser
    355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640
```

-continued

```
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
                965                 970                 975
Val Leu Arg Leu Lys Cys His Ser Leu Phe Leu Asp Leu Gln Val Asn
            980                 985                 990
Ser Leu Gln Thr Val Cys Thr Asn Ile Tyr Lys Ile Leu Leu Leu Gln
        995                1000                1005
Ala Tyr Arg Phe His Ala Cys Val Leu Gln Leu Pro Phe His Gln Gln
    1010                1015                1020
Val Trp Lys Asn Pro Thr Phe Phe Leu Arg Val Ile Ser Asp Thr Ala
1025                1030                1035                1040
Ser Leu Cys Tyr Ser Ile Leu Lys Ala Lys Asn Ala Gly Met Ser Leu
                1045                1050                1055
Gly Ala Lys Gly Ala Ala Gly Pro Leu Pro Ser Glu Ala Val Gln Trp
```

```
                    1060           1065           1070
Leu Cys His Gln Ala Phe Leu Leu Lys Leu Thr Arg His Arg Val Thr
        1075            1080           1085
Tyr Val Pro Leu Leu Gly Ser Leu Arg Thr Ala Gln Thr Gln Leu Ser
        1090           1095            1100
Arg Lys Leu Pro Gly Thr Thr Leu Thr Ala Leu Glu Ala Ala Ala Asn
1105           1110            1115            1120
Pro Ala Leu Pro Ser Asp Phe Lys Thr Ile Leu Asp
            1125            1130

<210> SEQ ID NO 9
<211> LENGTH: 3979
<212> TYPE: DNA
<213> ORGANISM: Homo sapiens

<400> SEQUENCE: 9
```

| | | | | | |
|---|---|---|---|---|---|
| gcagcgctgc | gtcctgctgc | gcacgtggga | agccctggcc | ccggccaccc | ccgcgatgcc | 60 |
| gcgcgctccc | cgctgccgag | ccgtgcgctc | cctgctgcgc | agccactacc | gcgaggtgct | 120 |
| gccgctggcc | acgttcgtgc | ggcgcctggg | gccccagggc | tggcggctgg | tgcagcgcgg | 180 |
| ggacccggcg | gctttccgcg | cgctggtggc | ccagtgcctg | gtgtgcgtgc | cctgggacgc | 240 |
| acggccgccc | cccgccgccc | cctccttccg | ccaggtgtcc | tgcctgaagg | agctggtggc | 300 |
| ccgagtgctg | cagaggctgt | gcgagcgcgg | cgcgaagaac | gtgctggcct | tcggcttcgc | 360 |
| gctgctggac | ggggcccgcg | ggggcccccc | cgaggccttc | accaccagcg | tgcgcagcta | 420 |
| cctgcccaac | acggtgaccg | acgcactgcg | ggggagcggg | gcgtgggggc | tgctgctgcg | 480 |
| ccgcgtgggc | gacgacgtgc | tggttcacct | gctggcacgc | tgcgcgctct | ttgtgctggt | 540 |
| ggctcccagc | tgcgcctacc | aggtgtgcgg | gccgccgctg | taccagctcg | gcgctgccac | 600 |
| tcaggcccgg | ccccgccac | acgctagtgg | accccgaagg | cgtctgggat | gcgaacgggc | 660 |
| ctggaaccat | agcgtcaggg | aggccggggt | ccccctgggc | ctgccagccc | cgggtgcgag | 720 |
| gaggcgcggg | ggcagtgcca | gccgaagtct | gccgttgccc | aagaggccca | ggcgtggcgc | 780 |
| tgcccctgag | ccggagcgga | cgcccgttgg | gcaggggtcc | tgggcccacc | cgggcaggac | 840 |
| gcgtggaccg | agtgaccgtg | gtttctgtgt | ggtgtcacct | gccagacccg | ccgaagaagc | 900 |
| cacctctttg | gagggtgcgc | tctctggcac | gcgccactcc | cacccatccg | tgggccgcca | 960 |
| gcaccacgcg | ggcccccat | ccacatcgcg | gccaccacgt | ccctgggaca | cgccttgtcc | 1020 |
| cccggtgtac | gccgagacca | agcacttcct | ctactcctca | ggcgacaagg | agcagctgcg | 1080 |
| gccctccttc | ctactcagct | ctctgaggcc | cagcctgact | ggcgctcgga | ggctcgtgga | 1140 |
| gaccatctttt | ctgggttcca | ggccctggat | gccaggggact | ccccgcaggt | tgccccgcct | 1200 |
| gcccagcgc | tactggcaaa | tgcggccccct | gtttctggag | ctgcttggga | accacgcgca | 1260 |
| gtgccctac | ggggtgctcc | tcaagacgca | ctgcccgctg | cgagctgcgg | tcaccccagc | 1320 |
| agccggtgtc | tgtgcccggg | agaagcccca | gggctctgtg | gcggccccg | aggaggagga | 1380 |
| cacagacccc | cgtcgcctgg | tgcagctgct | ccgccagcac | agcagccct | ggcaggtgta | 1440 |
| cggcttcgtg | cgggcctgcc | tgcgccggct | ggtgccccca | ggcctctggg | gctccaggca | 1500 |
| caacgaacgc | cgcttcctca | ggaacaccaa | gaagttcatc | tccctgggga | agcatgccaa | 1560 |
| gctctcgctg | caggagctga | cgtggaagat | gagcgtgcgg | gactgcgctt | ggctgcgcag | 1620 |
| gagcccaggg | gttggctgtg | ttccggccgc | agagcaccgt | ctgcgtgagg | agatcctggc | 1680 |
| caagttcctg | cactggctga | tgagtgtgta | cgtcgtcgag | ctgctcaggt | ctttcttta | 1740 |

-continued

```
tgtcacggag accacgtttc aaaagaacag gctctttttc taccggaaga gtgtctggag    1800
caagttgcaa agcattggaa tcagacagca cttgaagagg gtgcagctgc gggagctgtc    1860
ggaagcagag gtcaggcagc atcgggaagc caggcccgcc ctgctgacgt ccagactccg    1920
cttcatcccc aagcctgacg ggctgcggcc gattgtgaac atggactacg tcgtgggagc    1980
cagaacgttc cgcagagaaa agagggccga gcgtctcacc tcgagggtga aggcactgtt    2040
cagcgtgctc aactacgagc gggcgcggcg ccccggcctc ctgggcgcct ctgtgctggg    2100
cctggacgat atccacaggg cctggcgcac cttcgtgctg cgtgtgcggg cccaggaccc    2160
gccgcctgag ctgtactttg tcaaggacag gctcacggag gtcatcgcca gcatcatcaa    2220
accccagaac acgtactgcg tgcgtcggta tgccgtggtc cagaaggccg cccatgggca    2280
cgtccgcaag gccttcaaga gccacgtctc taccttgaca gacctccagc cgtacatgcg    2340
acagttcgtg gctcacctgc aggagaccag cccgctgagg gatgccgtcg tcatcgagca    2400
gagctcctcc ctgaatgagg ccagcagtgg cctcttcgac gtcttcctac gcttcatgtg    2460
ccaccacgcc gtgcgcatca ggggcaagtc ctacgtccag tgccagggga tcccgcaggg    2520
ctccatcctc tccacgctgc tctgcagcct gtgctacggc gacatggaga caagctgtt    2580 tgcggggatt cggcgggacg ggctgctcct gcgtttggtg gatgatttct tgttggtgac    2640
acctcacctc acccacgcga aaaccttcct caggaccctg gtccgaggtg tccctgagta    2700
tggctgcgtg gtgaacttgc ggaagacagt ggtgaacttc cctgtagaag acgaggccct    2760
gggtggcacg gcttttgttc agatgccggc ccacggccta ttcccctggt gcggcctgct    2820
gctggatacc cggaccctgg aggtgcagag cgactactcc agctatgccc ggacctccat    2880
cagagccagt ctcaccttca accgcggctt caaggctggg aggaacatgc gtcgcaaact    2940 ctttgggggtc ttgcggctga agtgtcacag cctgtttctg gatttgcagg tgaacagcct    3000
ccagacggtg tgcaccaaca tctacaagat cctcctgctg caggcgtaca ggtttcacgc    3060
atgtgtgctg cagctcccat ttcatcagca agtttggaag aaccccacat ttttcctgcg    3120
cgtcatctct gacacggcct ccctctgcta ctccatcctg aaagccaaga acgcagggat    3180
gtcgctgggg gccaagggcg ccgccggccc tctgccctcc gaggccgtgc agtggctgtg    3240
ccaccaagca ttcctgctca agctgactcg acaccgtgtc acctacgtgc cactcctggg    3300
gtcactcagg acagcccaga cgcagctgag tcggaagctc ccggggacga cgctgactgc    3360
cctggaggcc gcagccaacc cggcactgcc ctcagacttc aagaccatcc tggactgatg    3420
gccacccgcc cacagccagg ccgagagcag acaccagcag ccctgtcacg ccgggctcta    3480
cgtcccaggg agggaggggc ggcccacacc caggcccgca ccgctgggag tctgaggcct    3540
gagtgagtgt ttggccgagg cctgcatgtc cggctgaagg ctgagtgtcc ggctgaggcc    3600
tgagcgagtg tccagccaag ggctgagtgt ccagcacacc tgccgtcttc acttccccac    3660
aggctggcgc tcggctccac cccagggcca gcttttcctc accaggagcc cggcttccac    3720
tccccacata ggaatagtcc atccccagat tcgccattgt tcaccctcg ccctgccctc    3780 ctttgccttc caccccacc atccaggtgg agaccctgag aaggaccctg ggagctctgg    3840
gaatttggag tgaccaaagg tgtgccctgt acacaggcga ggaccctgca cctggatggg    3900
ggtccctgtg ggtcaaattg gggggaggtg ctgtgggagt aaaatactga atatatgagt    3960
ttttcagttt tgaaaaaaa                                                 3979
```

<210> SEQ ID NO 10

<211> LENGTH: 1120
<212> TYPE: PRT
<213> ORGANISM: Homo sapiens

<400> SEQUENCE: 10

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
```

```
              385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
                420                 425                 430
Gly Ser Val Ala Ala Pro Glu Glu Asp Thr Asp Pro Arg Arg Leu
                435                 440                 445
Val Gln Leu Leu Arg Gln His Ser Ser Pro Trp Gln Val Tyr Gly Phe
                450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
                500                 505                 510
Ser Val Arg Asp Cys Ala Trp Leu Arg Arg Ser Pro Gly Val Gly Cys
                515                 520                 525
Val Pro Ala Ala Glu His Arg Leu Arg Glu Glu Ile Leu Ala Lys Phe
                530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
                580                 585                 590
Leu Lys Arg Val Gln Leu Arg Glu Leu Ser Glu Ala Glu Val Arg Gln
                595                 600                 605
His Arg Glu Ala Arg Pro Ala Leu Leu Thr Ser Arg Leu Arg Phe Ile
                610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
                660                 665                 670
Pro Gly Leu Leu Gly Ala Ser Val Leu Gly Leu Asp Asp Ile His Arg
                675                 680                 685
Ala Trp Arg Thr Phe Val Leu Arg Val Arg Ala Gln Asp Pro Pro Pro
                690                 695                 700
Glu Leu Tyr Phe Val Lys Asp Arg Leu Thr Glu Val Ile Ala Ser Ile
705                 710                 715                 720
Ile Lys Pro Gln Asn Thr Tyr Cys Val Arg Arg Tyr Ala Val Val Gln
                725                 730                 735
Lys Ala Ala His Gly His Val Arg Lys Ala Phe Lys Ser His Val Ser
                740                 745                 750
Thr Leu Thr Asp Leu Gln Pro Tyr Met Arg Gln Phe Val Ala His Leu
                755                 760                 765
Gln Glu Thr Ser Pro Leu Arg Asp Ala Val Val Ile Glu Gln Ser Ser
                770                 775                 780
Ser Leu Asn Glu Ala Ser Ser Gly Leu Phe Asp Val Phe Leu Arg Phe
785                 790                 795                 800
Met Cys His His Ala Val Arg Ile Arg Gly Lys Ser Tyr Val Gln Cys
                805                 810                 815
```

```
Gln Gly Ile Pro Gln Gly Ser Ile Leu Ser Thr Leu Leu Cys Ser Leu
            820                 825                 830
Cys Tyr Gly Asp Met Glu Asn Lys Leu Phe Ala Gly Ile Arg Arg Asp
        835                 840                 845
Gly Leu Leu Arg Leu Val Asp Asp Phe Leu Leu Val Thr Pro His
    850                 855                 860
Leu Thr His Ala Lys Thr Phe Leu Arg Thr Leu Val Arg Gly Val Pro
865                 870                 875                 880
Glu Tyr Gly Cys Val Val Asn Leu Arg Lys Thr Val Val Asn Phe Pro
            885                 890                 895
Val Glu Asp Glu Ala Leu Gly Gly Thr Ala Phe Val Gln Met Pro Ala
        900                 905                 910
His Gly Leu Phe Pro Trp Cys Gly Leu Leu Leu Asp Thr Arg Thr Leu
    915                 920                 925
Glu Val Gln Ser Asp Tyr Ser Ser Tyr Ala Arg Thr Ser Ile Arg Ala
930                 935                 940
Ser Leu Thr Phe Asn Arg Gly Phe Lys Ala Gly Arg Asn Met Arg Arg
945                 950                 955                 960
Lys Leu Phe Gly Val Leu Arg Leu Lys Cys His Ser Leu Phe Leu Asp
            965                 970                 975
Leu Gln Val Asn Ser Leu Gln Thr Val Cys Thr Asn Ile Tyr Lys Ile
        980                 985                 990
Leu Leu Leu Gln Ala Tyr Arg Phe His Ala Cys Val Leu Gln Leu Pro
    995                 1000                1005
Phe His Gln Gln Val Trp Lys Asn Pro Thr Phe Phe Leu Arg Val Ile
    1010                1015                1020
Ser Asp Thr Ala Ser Leu Cys Tyr Ser Ile Leu Lys Ala Lys Asn Ala
1025                1030                1035                1040
Gly Met Ser Leu Gly Ala Lys Gly Ala Ala Gly Pro Leu Pro Ser Glu
            1045                1050                1055
Ala Val Gln Trp Leu Cys His Gln Ala Phe Leu Leu Lys Leu Thr Arg
        1060                1065                1070
His Arg Val Thr Tyr Val Pro Leu Leu Gly Ser Leu Arg Thr Ala Gln
    1075                1080                1085
Thr Gln Leu Ser Arg Lys Leu Pro Gly Thr Thr Leu Thr Ala Leu Glu
    1090                1095                1100
Ala Ala Ala Asn Pro Ala Leu Pro Ser Asp Phe Lys Thr Ile Leu Asp
1105                1110                1115                1120

<210> SEQ ID NO 11
<211> LENGTH: 3644
<212> TYPE: DNA
<213> ORGANISM: Homo sapiens

<400> SEQUENCE: 11
gcagcgctgc gtcctgctgc gcacgtggga agccctggcc ccggccaccc ccgcgatgcc    60
gcgcgctccc cgctgccgag ccgtgcgctc cctgctgcgc agccactacc gcgaggtgct   120
gccgctggcc acgttcgtgc ggcgcctggg gccccagggc tggcggctgg tgcagcgcgg   180
ggacccggcg gctttccgcg cgctggtggc ccagtgcctg gtgtgcgtgc ctgggacgc    240
acggccgccc ccgccgcccc cctccttccg ccaggtgtcc tgcctgaagg agctggtggc   300
ccgagtgctg cagaggctgt gcgagcgcgg cgcgaagaac gtgctggcct tcggcttcgc   360
gctgctggac ggggcccgcg ggggcccccc cgaggccttc accaccagcg tgcgcagcta   420
```

-continued

```
cctgcccaac acggtgaccg acgcactgcg ggggagcggg gcgtggggc tgctgctgcg      480
ccgcgtgggc gacgacgtgc tggttcacct gctggcacgc tgcgcgctct tgtgctggt      540
ggctcccagc tgcgcctacc aggtgtgcgg ccgccgctg taccagctcg cgcctgccac     600
tcaggcccgg cccccgccac acgctagtgg accccgaagg cgtctgggat gcgaacgggc     660
ctggaaccat agcgtcaggg aggccggggt cccctgggc ctgccagccc cgggtgcgag      720
gaggcgcggg ggcagtgcca gccgaagtct gccgttgccc aagaggccca ggcgtggcgc     780
tgccctgag ccggagcgga cgcccgttgg cagggtcc tgggcccacc cgggcaggac        840
gcgtggaccg agtgaccgtg gtttctgtgt ggtgtcacct gccagacccg ccgaagaagc     900
cacctctttg gagggtgcgc tctctggcac gcgccactcc cacccatccg tgggccgcca     960
gcaccacgcg ggccccccat ccacatcgcg gccaccacgt ccctgggaca cgccttgtcc    1020
cccggtgtac gccgagacca agcacttcct ctactcctca ggcgacaagg agcagctgcg    1080
gccctccttc ctactcagct ctctgaggcc cagcctgact ggcgctcgga ggctcgtgga    1140
gaccatcttt ctgggttcca ggccctggat gccaggact ccccgcaggt tgccccgcct    1200
gccccagcgc tactggcaaa tgcggcccct gtttctggag ctgcttggga accacgcgca    1260
gtgcccctac ggggtgctcc tcaagacgca ctgcccgctg cgagctgcgg tcaccccagc    1320
agccggtgtc tgtgcccggg agaagcccca gggtctgtg gcggccccg aggaggagga     1380
cacagacccc cgtcgcctgg tgcagctgct ccgccagcac agcagcccct ggcaggtgta    1440
cggcttcgtg cgggcctgcc tgcgccggct ggtgcccca ggcctctggg gctccaggca    1500
caacgaacgc cgcttcctca ggaacaccaa gaagttcatc tccctgggga agcatgccaa    1560
gctctcgctg caggagctga cgtggaagat gagcgtgcgg gactgcgctt ggctgcgcag    1620
gagcccaggg gttggctgtg ttccggccgc agagcaccgt ctgcgtgagg agatcctggc    1680
caagttcctg cactggctga tgagtgtgta cgtcgtcgag ctgctcaggt ctttctttta    1740
tgtcacggag accacgtttc aaaagaacag gctcttttc taccggaaga gtgtctggag    1800
caagttgcaa agcattggaa tcagacagca cttgaagagg gtgcagctgc gggagctgtc    1860
ggaagcagag gtcaggcagc atcgggaagc caggcccgcc ctgctgacgt ccagactccg    1920
cttcatcccc aagcctgacg gctgcggcc gattgtgaac atggactacg tcgtgggagc    1980
cagaacgttc cgcagagaaa agagggccga gcgtctcacc tcgagggtga aggcactgtt    2040
cagcgtgctc aactacgagc gggcgcggcg ccccggcctc ctgggcgcct ctgtgctggg    2100
cctggacgat atccacaggg cctggcgcac cttcgtgctg cgtgtgcggg cccaggaccc    2160
gccgcctgag ctgtactttg tcaaggtgga tgtgacgggc gcgtacgaca ccatccccca    2220
ggacaggctc acggaggtca tcgccagcat catcaaaccc cagaacacgt actgcgtgcg    2280
tcggtatgcc gtggtccaga aggccgccca tgggcacgtc cgcaaggcct tcaagagcca    2340
cgtcctacgt ccagtgccag gggatcccgc agggctccat cctctccacg ctgctctgca    2400
gcctgtgcta cggcgacatg gagaacaagc tgtttgcggg gattcggcgg acgggctgc    2460
tcctgcgttt ggtggatgat tcttgttgg tgacacctca cctcacccac gcgaaaacct    2520
tcctcagcta tgcccggacc tccatcgag ccagtctcac cttcaaccgc ggcttcaagg    2580
ctgggaggaa catgcgtcgc aaactcttg gggtcttgcg gctgaagtgt cacagcctgt    2640
ttctggattt gcaggtgaac agcctccaga cggtgtgcac caacatctac aagatcctcc    2700
tgctgcaggc gtacaggttt cacgcatgtg tgctgcagct cccatttcat cagcaagttt    2760
```

```
ggaagaaccc cacattttc ctgcgcgtca tctctgacac ggcctccctc tgctactcca    2820
tcctgaaagc caagaacgca gggatgtcgc tgggggccaa gggcgccgcc ggccctctgc    2880
cctccgaggc cgtgcagtgg ctgtgccacc aagcattcct gctcaagctg actcgacacc    2940
gtgtcaccta cgtgccactc ctggggtcac tcaggacagc ccagacgcag ctgagtcgga    3000
agctcccggg gacgacgctg actgccctgg aggccgcagc caacccggca ctgccctcag    3060
acttcaagac catcctggac tgatggccac ccgcccacag ccaggccgag agcagacacc    3120
agcagccctg tcacgccggg ctctacgtcc cagggaggga ggggcggccc acacccaggc    3180
ccgcaccgct gggagtctga ggcctgagtg agtgtttggc cgaggcctgc atgtccggct    3240
gaaggctgag tgtccggctg aggcctgagc gagtgtccag ccaagggctg agtgtccagc    3300
acacctgccg tcttcacttc cccacaggct ggcgctcggc tccacccag  ggccagcttt    3360 tcctcaccag gagcccggct tccactcccc acataggaat agtccatccc cagattcgcc    3420
attgttcacc cctcgccctg ccctcctttg ccttccaccc ccaccatcca ggtggagacc    3480
ctgagaagga ccctgggagc tctgggaatt tggagtgacc aaaggtgtgc cctgtacaca    3540
ggcgaggacc ctgcacctgg atggggtcc ctgtgggtca aattggggg aggtgctgtg    3600 ggagtaaaat actgaatata tgagttttc agttttgaaa aaaa                     3644
```

<210> SEQ ID NO 12
<211> LENGTH: 807
<212> TYPE: PRT
<213> ORGANISM: Homo sapiens

<400> SEQUENCE: 12

```
Met Pro Arg Ala Pro Arg Cys Arg Ala Val Arg Ser Leu Leu Arg Ser
1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220
```

```
Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
            245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
            290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Ser Ser Leu Arg Pro
                340                 345                 350

Ser Leu Thr Gly Ala Arg Arg Leu Val Glu Thr Ile Phe Leu Gly Ser
                355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
    515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
            610                 615                 620

Pro Lys Pro Asp Gly Leu Arg Pro Ile Val Asn Met Asp Tyr Val Val
625                 630                 635                 640
```

```
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Leu Arg Pro Val Pro
        755                 760                 765
Gly Asp Pro Ala Gly Leu His Pro Leu His Ala Ala Leu Gln Pro Val
    770                 775                 780
Leu Arg Arg His Gly Glu Gln Ala Val Cys Gly Asp Ser Ala Gly Arg
785                 790                 795                 800
Ala Ala Pro Ala Phe Gly Gly
                805

<210> SEQ ID NO 13
<211> LENGTH: 3608
<212> TYPE: DNA
<213> ORGANISM: Homo sapiens

<400> SEQUENCE: 13
gcagcgctgc gtcctgctgc gcacgtggga agccctggcc ccggccaccc ccgcgatgcc      60
gcgcgctccc cgctgccgag ccgtgcgctc cctgctgcgc agccactacc gcgaggtgct     120
gccgctggcc acgttcgtgc ggcgcctggg gccccagggc tggcggctgg tgcagcgcgg     180
ggacccggcg gctttccgcg cgctggtggc ccagtgcctg gtgtgcgtgc cctgggacgc     240
acggccgccc ccgccgcccc cctccttccg ccaggtgtcc tgcctgaagg agctggtggc     300
ccgagtgctg cagaggctgt gcgagcgcgg cgcgaagaac gtgctggcct tcggcttcgc     360
gctgctggac ggggcccgcg ggggcccccc cgaggccttc accaccagcg tgcgcagcta     420
cctgcccaac acggtgaccg acgcactgcg ggggagcggg gcgtgggggc tgctgctgcg     480
ccgcgtgggc gacgacgtgc tggttcacct gctggcacgc tgcgcgctct tgtgctggt     540
ggctcccagc tgcgcctacc aggtgtgcgc gccgccgctg taccagctcg cgctgccac     600
tcaggcccgg ccccgccac acgctagtgg accccgaagg cgtctgggat gcgaacgggc     660
ctggaaccat agcgtcaggg aggccggggt cccctgggc ctgccagccc cgggtgcgag     720
gaggcgcggg ggcagtgcca gccgaagtct gccgttgccc aagaggccca ggcgtggcgc     780
tgccctgag ccgagcgga cgcccgttgg caggggtcc tgggcccacc cgggcaggac     840
gcgtggaccg agtgaccgtg gtttctgtgt ggtgtcacct gccagacccg ccgaagaagc     900
cacctctttg gagggtgcgc tctctggcac gcgccactcc cacccatccg tgggccgcca     960
gcaccacgcg ggccccccat ccacatcgcg gccaccacgt cctgggaca cgccttgtcc    1020
cccggtgtac gccagaccaa agcacttcct ctactcctca ggcgacaagg agcagctgcg    1080
gccctccttc ctactcagct ctctgaggcc cagcctgact ggcgctcgga ggctcgtgga    1140
```

```
gaccatctttt ctgggttcca ggccctggat gccagggact ccccgcaggt tgccccgcct    1200
gccccagcgc tactggcaaa tgcggcccct gtttctggag ctgcttggga accacgcgca    1260
gtgcccctac ggggtgctcc tcaagacgca ctgcccgctg cgagctgcgg tcacccagc     1320 agccggtgtc tgtgcccggg agaagcccca gggtctgtg gcggccccg aggaggagga      1380 cacagacccc cgtcgcctgg tgcagctgct ccgccagcac agcagcccct ggcaggtgta    1440
cggcttcgtg cgggcctgcc tgcgccggct ggtgccccca ggcctctggg ctccaggca    1500 caacgaacgc cgcttcctca ggaacaccaa gaagttcatc tccctgggga agcatgccaa    1560
gctctcgctg caggagctga cgtggaagat gagcgtgcgg gactgcgctt ggctgcgcag    1620
gagcccaggg gttggctgtg ttccggccgc agagcaccgt ctgcgtgagg agatcctggc    1680
caagttcctg cactggctga tgagtgtgta cgtcgtcgag ctgctcaggt cttctcttta    1740
tgtcacggag accacgtttc aaaagaacag gctctttttc taccggaaga gtgtctggag    1800
caagttgcaa agcattggaa tcagacagca cttgaagagg gtgcagctgc gggagctgtc    1860
ggaagcagag gtcaggcagc atcgggaagc caggcccgcc ctgctgacgt ccagactccg    1920
cttcatcccc aagcctgacg ggctgcggcc gattgtgaac atggactacg tcgtgggagc    1980
cagaacgttc cgcagagaaa agagggccga gcgtctcacc tcgagggtga aggcactgtt    2040
cagcgtgctc aactacgagc gggcgcggcg ccccggcctc ctgggcgcct ctgtgctggg    2100
cctggacgat atccacaggg cctggcgcac cttcgtgctg cgtgtgcggg cccaggaccc    2160
gccgcctgag ctgtactttg tcaaggacag gctcacggag gtcatcgcca gcatcatcaa    2220
accccagaac acgtactgcg tgcgtcggta tgccgtggtc cagaaggccg cccatgggca    2280
cgtccgcaag gccttcaaga gccacgtcct acgtccagtg ccaggggatc ccgcagggct    2340
ccatcctctc cacgctgctc tgcagcctgt gctacggcga catggagaac aagctgtttg    2400
cggggattcg gcgggacggg ctgctcctgc gtttggtgga tgatttcttg ttggtgacac    2460
ctcacctcac ccacgcgaaa accttcctca gctatgcccg gacctccatc agagccagtc    2520
tcaccttcaa ccgcggcttc aaggctggga ggaacatgcg tcgcaaactc tttggggtct    2580
tgcggctgaa gtgtcacagc ctgtttctgg atttgcaggt gaacagcctc cagacggtgt    2640
gcaccaacat ctacaagatc ctcctgctgc aggcgtacag gtttcacgca tgtgtgctgc    2700
agctcccatt tcatcagcaa gtttggaaga accccacatt tttcctgcgc gtcatctctg    2760
acacggcctc cctctgctac tccatcctga aagccaagaa cgcagggatg tcgctggggg    2820
ccaagggcgc cgccggccct ctgccctccg aggccgtgca gtggctgtgc accaagcat    2880 tcctgctcaa gctgactcga caccgtgtca cctacgtgcc actcctgggg tcactcagga    2940
cagcccagac gcagctgagt cggaagctcc cggggacgac gctgactgcc ctggaggccg    3000
cagccaaccc ggcactgccc tcagacttca agaccatcct ggactgatgg ccacccgccc    3060
acagccaggc cgagagcaga caccagcagc cctgtcacgc cgggctctac gtcccaggga    3120
gggaggggcg gccacaccc aggcccgcac cgctgggagt ctgaggcctg agtgagtgtt    3180 tggccgagc ctgcatgtcc ggctgaaggc tgagtgtccg gctgaggcct gagcgagtgt     3240
ccagccaagg gctgagtgtc cagcacacct gccgtcttca cttccccaca ggctggcgct    3300
cggctccacc ccagggccag cttttcctca ccagagcccc ggcttccact ccccacatag    3360
gaatagtcca tccccagatt cgccattgtt caccctcgc cctgccctcc tttgccttcc     3420 accccccacca tccaggtgga gaccctgaga aggaccctgg gagctctggg aatttggagt    3480
gaccaaaggt gtgccctgta cacaggcgag gaccctgcac ctggatgggg gtccctgtgg    3540
```

```
gtcaaattgg ggggaggtgc tgtgggagta aaatactgaa tatatgagtt tttcagtttt    3600
gaaaaaaa                                                             3608
```

<210> SEQ ID NO 14
<211> LENGTH: 795
<212> TYPE: PRT
<213> ORGANISM: Homo sapiens

<400> SEQUENCE: 14

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350
```

```
Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Asp Arg Leu Thr Glu Val Ile Ala Ser Ile
705                 710                 715                 720

Ile Lys Pro Gln Asn Thr Tyr Cys Val Arg Arg Tyr Ala Val Val Gln
                725                 730                 735

Lys Ala Ala His Gly His Val Arg Lys Ala Phe Lys Ser His Val Leu
            740                 745                 750

Arg Pro Val Pro Gly Asp Pro Ala Gly Leu His Pro Leu His Ala Ala
        755                 760                 765

Leu Gln Pro Val Leu Arg Arg His Gly Glu Gln Ala Val Cys Gly Asp
```

Ser Ala Gly Arg Ala Ala Pro Ala Phe Gly Gly
785             790                 795

<210> SEQ ID NO 15
<211> LENGTH: 5748
<212> TYPE: DNA
<213> ORGANISM: Homo sapiens

<400> SEQUENCE: 15

| | | | | | |
|---|---|---|---|---|---|
| gagaagaaag | ccagtgcgtc | tctgggcgca | ggggccagtg | gggctcggag | gcacaggcac | 60 |
| cccgcgacac | tccaggttcc | ccgacccacg | tccctggcag | ccccgattat | ttacagcctc | 120 |
| agcagagcac | ggggcggggg | cagaggggcc | cgcccgggag | ggctgctact | tcttaaaacc | 180 |
| tctgcgggct | gcttagtcac | agcccccctt | gcttgggtgt | gtccttcgct | cgctccctcc | 240 |
| ctccgtctta | ggtcactgtt | ttcaacctcg | aataaaaact | gcagccaact | tccgaggcag | 300 |
| cctcattgcc | cagcggaccc | cagcctctgc | caggttcggt | ccgccatcct | cgtcccgtcc | 360 |
| tccgccggcc | cctgccccgc | gcccagggat | cctccagctc | ctttcgcccg | cgccctccgt | 420 |
| tcgctccgga | caccatggac | aagttttggt | ggcacgcagc | ctggggactc | tgcctcgtgc | 480 |
| cgctgagcct | ggcgcagatc | gatttgaata | taacctgccg | cttttgcaggt | gtattccacg | 540 |
| tggagaaaaa | tggtcgctac | agcatctctc | ggacggaggc | cgctgacctc | tgcaaggctt | 600 |
| tcaatagcac | cttgcccaca | atggcccaga | tggagaaagc | tctgagcatc | ggatttgaga | 660 |
| cctgcaggta | tgggttcata | gaagggcacg | tggtgattcc | ccggatccac | cccaactcca | 720 |
| tctgtgcagc | aaacaacaca | ggggtgtaca | tcctcacatc | caacacctcc | cagtatgaca | 780 |
| catattgctt | caatgcttca | gctccacctg | aagaagattg | tacatcagtc | acagacctgc | 840 |
| ccaatgcctt | tgatggacca | attaccataa | ctattgttaa | ccgtgatggc | acccgctatg | 900 |
| tccagaaagg | agaatacaga | acgaatcctg | aagcatccta | cccagcaac | cctactgatg | 960 |
| atgacgtgag | cagcggctcc | tccagtgaaa | ggagcagcac | ttcaggaggt | tacatctttt | 1020 |
| acacccttttc | tactgtacac | cccatcccag | acgaagacag | tccctggatc | accgacagca | 1080 |
| cagacagaat | ccctgctacc | actttgatga | gcactagtgc | tacagcaact | gagacagcaa | 1140 |
| ccaagaggca | agaaacctgg | gattggtttt | catggttgtt | tctaccatca | gagtcaagga | 1200 |
| atcatcttca | cacaacaaca | caaatggctg | gtacgtcttc | aaataccatc | tcagcaggct | 1260 |
| gggagccaaa | tgaagaaaat | gaagatgaaa | gagacagaca | cctcagtttt | tctggatcag | 1320 |
| gcattgatga | tgatgaagat | tttatctcca | gcaccatttc | aaccacacca | cgggcttttg | 1380 |
| accacacaaa | acagaaccag | gactggaccc | agtggaaccc | aagccattca | aatccggaag | 1440 |
| tgctacttca | gacaaccaca | aggatgactg | atgtagacag | aaatggcacc | actgcttatg | 1500 |
| aaggaaactg | gaacccagaa | gcacaccctc | ccctcattca | ccatgagcat | catgaggaag | 1560 |
| aagagacccc | acattctaca | agcacaatcc | aggcaactcc | tagtagtaca | acggaagaaa | 1620 |
| cagctaccca | gaaggaacag | tggtttggca | acagatggca | tgagggatat | cgccaaacac | 1680 |
| ccaaagaaga | ctcccattcg | acaacaggga | cagctgcagc | ctcagctcat | accagccatc | 1740 |
| caatgcaagg | aaggacaaca | ccaagcccag | aggacagttc | ctggactgat | tcttcaacc | 1800 |
| caatctcaca | ccccatggga | cgaggtcatc | aagcaggaag | aaggatggat | atggactcca | 1860 |
| gtcatagtat | aacgcttcag | cctactgcaa | atcaaacac | aggtttggtg | aagatttgg | 1920 |
| acaggacagg | acctctttca | atgacaacgc | agcagagtaa | ttctcagagc | ttctctacat | 1980 |

```
cacatgaagg cttggaagaa gataaagacc atccaacaac ttctactctg acatcaagca   2040
ataggaatga tgtcacaggt ggaagaagag acccaaatca ttctgaaggc tcaactactt   2100
tactggaagg ttatacctct cattacccac acacgaagga aagcaggacc ttcatcccag   2160
tgacctcagc taagactggg tcctttggag ttactgcagt tactgttgga gattccaact   2220
ctaatgtcaa tcgttcctta tcaggagacc aagacacatt ccaccccagt gggggtccc    2280 ataccactca tggatctgaa tcagatggac actcacatgg gagtcaagaa ggtggagcaa   2340
acacaacctc tggtcctata aggacacccc aaattccaga atggctgatc atcttggcat   2400
ccctcttggc cttggcttg attcttgcag tttgcattgc agtcaacagt cgaagaaggt    2460
gtgggcagaa gaaaaagcta gtgatcaaca gtggcaatgg agctgtggag acagaaagc    2520 caagtggact caacgagag gccagcaagt ctcaggaaat ggtgcatttg gtgaacaagg    2580
agtcgtcaga aactccagac cagtttatga cagctgatga gacaaggaac ctgcagaatg   2640
tggacatgaa gattggggtg taacacctac accattatct tggaaagaaa caaccgttgg   2700
aaacataacc attacaggga gctgggacac ttaacagatg caatgtgcta ctgattgttt   2760
cattgcgaat cttttttagc ataaaatttt ctactctttt tgttttttgt gttttgttct   2820
ttaaagtcag gtccaatttg taaaaacagc attgctttct gaaattaggg cccaattaat   2880
aatcagcaag aatttgatcg ttccagttcc cacttggagg cctttcatcc ctcgggtgtg   2940
ctatggatgg cttctaacaa aaactacaca tatgtattcc tgatcgccaa ccttccccc    3000 accagctaag gacatttccc agggttaata gggcctggtc cctgggagga aatttgaatg   3060
ggtccatttt gcccttccat agcctaatcc ctgggcattg ctttccactg aggttggggg   3120
ttggggtgta ctagttacac atcttcaaca gacccctct agaaatttt cagatgcttc     3180 tgggagacac ccaaagggtg aagctattta tctgtagtaa actatttatc tgtgttttg    3240 aaatattaaa ccctggatca gtcctttgat cagtataatt ttttaaagtt actttgtcag   3300
aggcacaaaa gggtttaaac tgattcataa taaatatctg tacttcttcg atcttcacct   3360
tttgtgctgt gattcttcag tttctaaacc agcactgtct gggtccctac aatgtatcag   3420
gaagagctga gaatggtaag gagactcttc taagtcttca tctcagagac cctgagttcc   3480
cactcagacc cactcagcca aatctcatgg aagaccaagg agggcagcac tgttttgtt    3540 ttttgttttt tgtttttttt ttttgacact gtccaaaggt tttccatcct gtcctggaat   3600
cagagttgga agctgaggag cttcagcctc ttttatggtt taatggccac ctgttctctc   3660
ctgtgaaagg ctttgcaaag tcacattaag tttgcatgac ctgttatccc tggggcccta   3720
tttcatagag gctggcccta ttagtgattt ccaaaaacaa tatggaagtg ccttttgatg   3780
tcttacaata agagaagaag ccaatggaaa tgaaagagat tggcaaaggg aaggatgat    3840 gccatgtaga tcctgtttga catttttatg gctgtatttg taaacttaaa cacaccagtg   3900
tctgttcttg atgcagttgc tatttaggat gagttaagtg cctggggagt ccctcaaaag   3960
gttaaaggga ttcccatcat tggaatctta tcaccagata ggcaagttta tgaccaaaca   4020
agagagtact ggctttatcc tctaacctca tattttctcc cacttggcaa gtcctttgtg   4080
gcatttattc atcagtcagg gtgtccgatt ggtcctagaa cttccaaagg ctgcttgtca   4140
tagaagccat tgcatctata aagcaacggc tcctgttaaa tggtatctcc tttctgaggc   4200
tcctactaaa agtcatttgt tacctaaact tatgtgctta acaggcaatg cttctcagac   4260
cacaaagcag aaagaagaag aaaagctcct gactaaatca gggctgggct tagacagagt   4320
tgatctgtag aatatctta aaggagagat gtcaactttc tgcactattc ccagcctctg    4380
```

```
ctcctccctg tctaccctct cccctccctc tctccctcca cttcacccca caatcttgaa    4440
aaacttcctt tctcttctgt gaacatcatt ggccagatcc attttcagtg gtctggattt    4500 cttttattt tcttttcaac ttgaaagaaa ctggacatta ggccactatg tgttgttact    4560
gccactagtg ttcaagtgcc tcttgttttc ccagagattt cctgggtctg ccagaggccc    4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaagaggc tgagacagga    4800 ggttattttc aatttatttt tggaattaaa tacttttttc cctttattac tgttgtagtc    4860
cctcacttgg atatacctct gttttcacga tagaaataag ggaggtctag agcttctatt    4920
ccttggccat tgtcaacgga gagctggcca agtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcattt    5100
aaactgggtc tttataaaag taaaaggcca acatttaatt attttgcaaa gcaacctaag    5160
agctaaagat gtaattttc ttgcaattgt aaatcttttg tgtctcctga agacttccct    5220
taaaattagc tctgagtgaa aaatcaaaag agacaaaaga catcttcgaa tccatatttc    5280
aagcctggta gaattggctt ttctagcaga acctttccaa aagttttata ttgagattca    5340
taacaacacc aagaattgat tttgtagcca acattcattc aatactgtta tatcagagga    5400
gtaggagaga ggaaacattt gacttatctg gaaaagcaaa atgtacttaa gaataagaat    5460
aacatggtcc attcacccttt atgttataga tatgtctttg tgtaaatcat ttgttttgag    5520
ttttcaaaga atagcccatt gttcattctt gtgctgtaca atgaccactg ttattgttac    5580 tttgacttt cagagcacac ccttcctctg gttttgtat atttattgat ggatcaataa    5640
taatgaggaa agcatgatat gtatattgct gagttgaaag cacttattgg aaaatattaa    5700
aaggctaaca ttaaaagact aaaggaaaca gaaaaaaaaa aaaaaaaa                 5748
```

<210> SEQ ID NO 16
<211> LENGTH: 742
<212> TYPE: PRT
<213> ORGANISM: Homo sapiens

<400> SEQUENCE: 16

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125
```

```
Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
    275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
    435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
            515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
```

```
545                 550                 555                 560
Thr Ser His Tyr Pro His Thr Lys Glu Ser Arg Thr Phe Ile Pro Val
                565                 570                 575
Thr Ser Ala Lys Thr Gly Ser Phe Gly Val Thr Ala Val Thr Val Gly
                580                 585                 590
Asp Ser Asn Ser Asn Val Asn Arg Ser Leu Ser Gly Asp Gln Asp Thr
                595                 600                 605
Phe His Pro Ser Gly Gly Ser His Thr Thr His Gly Ser Glu Ser Asp
                610                 615                 620
Gly His Ser His Gly Ser Gln Glu Gly Ala Asn Thr Thr Ser Gly
625                 630                 635                 640
Pro Ile Arg Thr Pro Gln Ile Pro Glu Trp Leu Ile Ile Leu Ala Ser
                645                 650                 655
Leu Leu Ala Leu Ala Leu Ile Leu Ala Val Cys Ile Ala Val Asn Ser
                660                 665                 670
Arg Arg Arg Cys Gly Gln Lys Lys Lys Leu Val Ile Asn Ser Gly Asn
                675                 680                 685
Gly Ala Val Glu Asp Arg Lys Pro Ser Gly Leu Asn Gly Glu Ala Ser
                690                 695                 700
Lys Ser Gln Glu Met Val His Leu Val Asn Lys Glu Ser Ser Glu Thr
705                 710                 715                 720
Pro Asp Gln Phe Met Thr Ala Asp Glu Thr Arg Asn Leu Gln Asn Val
                725                 730                 735
Asp Met Lys Ile Gly Val
                740

<210> SEQ ID NO 17
<211> LENGTH: 5619
<212> TYPE: DNA
<213> ORGANISM: Homo sapiens

<400> SEQUENCE: 17
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccct tgcttgggtgt gtccttcgct cgctccctcc    240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagttttggt ggcacgcagc ctgggactc tgcctcgtgc      480
cgctgagcct ggcgcagatc gatttgaata taacctgccg ctttgcaggt gtattccacg     540
tggagaaaaa tggtcgctac agcatctctc ggacggaggc cgctgacctc tgcaaggctt     600
tcaatagcac cttgcccaca atggcccaga tggagaaagc tctgagcatc ggatttgaga     660
cctgcaggta tgggttcata gaagggcacg tggtgattcc ccggatccac cccaactcca     720
tctgtgcagc aaacaacaca ggggtgtaca tcctcacatc caacacctcc agtatgaca     780
catattgctt caatgcttca gctccacctg aagaagattg tacatcagtc acagacctgc     840
ccaatgcctt tgatggacca attaccataa ctattgttaa ccgtgatggc acccgctatg     900
tccagaaagg agaatacaga acgaatcctg aagacatcta ccccagcaac ctactgatg     960
atgacgtgag cagcggctcc tccagtgaaa ggagcagcac ttcaggaggt tacatctttt    1020
```

-continued

```
acacctttc tactgtacac cccatcccag acgaagacag tccctggatc accgacagca    1080
cagacagaat ccctgctacc agtacgtctt caaataccat ctcagcaggc tgggagccaa    1140
atgaagaaaa tgaagatgaa agagacagac acctcagttt ttctggatca ggcattgatg    1200
atgatgaaga tttatctcc agcaccattt caaccacacc acgggctttt gaccacacaa     1260
aacagaacca ggactggacc cagtggaacc caagccattc aaatccggaa gtgctacttc    1320
agacaaccac aaggatgact gatgtagaca gaaatggcac cactgcttat gaaggaaact    1380
ggaacccaga agcacaccct cccctcattc accatgagca tcatgaggaa gagagaccc     1440
cacattctac aagcacaatc caggcaactc ctagtagtac aacggaagaa acagctaccc    1500
agaaggaaca gtggtttggc aacagatggc atgagggata tcgccaaaca cccaaagaag    1560
actcccattc gacaacaggg acagctgcag cctcagctca taccagccat ccaatgcaag    1620
gaaggacaac accaagccca gaggacagtt cctggactga tttcttcaac ccaatctcac    1680
accccatggg acgaggtcat caagcaggaa gaaggatgga tatggactcc agtcatagta    1740
taacgcttca gcctactgca aatccaaaca caggtttggt ggaagatttg acaggacag     1800
gacctctttc aatgacaacg cagcagagta attctcagag cttctctaca tcacatgaag    1860
gcttggaaga agataaagac catccaacaa cttctactct gacatcaagc aataggaatg    1920
atgtcacagg tggaagaaga gacccaaatc attctgaagg ctcaactact ttactggaag    1980
gttatacctc tcattaccca cacacgaagg aaagcaggac cttcatccca gtgacctcag    2040
ctaagactgg gtcctttgga gttactgcag ttactgttgg agattccaac tctaatgtca    2100
atcgttcctt atcaggagac caagacacat tccaccccag tgggggtcc cataccactc      2160
atggatctga atcagatgga cactcacatg ggagtcaaga aggtggagca aacacaacct    2220
ctggtcctat aaggacaccc caaattccag aatggctgat catcttggca tccctcttgg    2280
ccttggcttt gattcttgca gtttgcattg cagtcaacag tcgaagaagg tgtgggcaga    2340
agaaaaagct agtgatcaac agtggcaatg gagctgtgga ggacagaaag ccaagtggac    2400
tcaacggaga ggccagcaag tctcaggaaa tggtgcattt ggtgaacaag gagtcgtcag    2460
aaactccaga ccagtttatg acagctgatg agacaaggaa cctgcagaat gtggacatga    2520
agattggggt gtaacaccta caccattatc ttggaaagaa acaaccgttg gaaacataac    2580
cattacaggg agctgggaca cttaacagat gcaatgtgct actgattgtt tcattgcgaa    2640
tctttttag cataaaattt tctactcttt ttgttttgtt tgttttgttc tttaaagtca     2700
ggtccaattt gtaaaaacag cattgctttc tgaaattagg gcccaattaa taatcagcaa    2760
gaatttgatc gttccagttc ccacttggag gcctttcatc cctcgggtgt gctatggatg    2820
gcttctaaca aaaactacac atatgtattc ctgatcgcca acctttcccc caccagctaa    2880
ggacatttcc cagggttaat agggcctggt ccctgggagg aaatttgaat gggtccattt    2940
tgcccttcca tagcctaatc cctgggcatt gctttccact gaggttgggg gttgggtgt     3000
actagttaca catcttcaac agacccccct ctagaaatttt tcagatgctt ctgggagaca   3060
cccaaagggt gaagctattt atctgtagta aactatttat ctgtgttttt gaaatattaa    3120
accctggatc agtcctttga tcagtataat tttttaaagt tactttgtca gaggcacaaa    3180
agggtttaaa ctgattcata ataaatatct gtacttcttc gatcttcacc ttttgtgctg    3240
tgattcttca gtttctaaac cagcactgtc tgggtcccta caatgtatca ggaagagctg    3300
agaatggtaa ggagactctt ctaagtcttc atctcagaga ccctgagttc ccactcagac    3360
```

```
ccactcagcc aaatctcatg gaagaccaag gagggcagca ctgttttgt tttttgtttt      3420
ttgttttttt ttttgacac tgtccaaagg ttttccatcc tgtcctggaa tcagagttgg       3480
aagctgagga gcttcagcct cttttatggt ttaatggcca cctgttctct cctgtgaaag      3540
gctttgcaaa gtcacattaa gtttgcatga cctgttatcc ctggggccct atttcataga     3600
ggctggccct attagtgatt tccaaaaaca atatggaagt gccttttgat gtcttacaat     3660
aagagaagaa gccaatggaa atgaaagaga ttggcaaagg ggaaggatga tgccatgtag     3720
atcctgtttg acatttttat ggctgtattt gtaaacttaa acacaccagt gtctgttctt     3780
gatgcagttg ctatttagga tgagttaagt gcctggggag tccctcaaaa ggttaaaggg     3840
attcccatca ttggaatctt atcaccagat aggcaagttt atgaccaaac aagagagtac    3900
tggctttatc ctctaacctc atattttctc ccacttggca agtcctttgt ggcatttatt      3960
catcagtcag ggtgtccgat tggtcctaga acttccaaag gctgcttgtc atagaagcca    4020
ttgcatctat aaagcaacgg ctcctgttaa atggtatctc ctttctgagg ctcctactaa    4080
aagtcatttg ttacctaaac ttatgtgctt aacaggcaat gcttctcaga ccacaaagca    4140
gaaagaagaa gaaaagctcc tgactaaatc agggctgggc ttagacagag ttgatctgta   4200
gaatatcttt aaaggagaga tgtcaacttt ctgcactatt cccagcctct gctcctccct     4260
gtctaccctc tccctccct ctctccctcc acttcaccc acaatcttga aaaacttcct      4320
ttctcttctg tgaacatcat tggccagatc cattttcagt ggtctggatt tctttttatt      4380
ttcttttcaa cttgaaagaa actggacatt aggccactat gtgttgttac tgccactagt    4440
gttcaagtgc ctcttgtttt cccagagatt tcctgggtct gccagaggcc cagacaggct    4500
cactcaagct ctttaactga aaagcaacaa gccactccag acaaggttc aaaatggtta     4560
caacagcctc tacctgtcgc cccagggaga aagggggtagt gatacaagtc tcatagccag   4620
agatggtttt ccactccttc tagatattcc caaaaagagg ctgagacagg aggttatttt    4680
caatttatt ttggaattaa atactttttt ccctttatta ctgttgtagt ccctcacttg      4740
gatatacctc tgttttcacg atagaaataa gggaggtcta gagcttctat tccttggcca   4800
ttgtcaacgg agagctggcc aagtcttcac aaacccttgc aacattgcct gaagtttatg    4860
gaataagatg tattctcact cccttgatct caagggcgta actctggaag cacagcttga   4920
ctacacgtca tttttaccaa tgattttcag gtgacctggg ctaagtcatt taaactgggt    4980
ctttataaaa gtaaaaggcc aacatttaat tattttgcaa agcaacctaa gagctaaaga    5040
tgtaattttt cttgcaattg taaatctttt gtgtctcctg aagacttccc ttaaaattag    5100
ctctgagtga aaaatcaaaa gagacaaaag acatcttcga atccatattt caagcctggt    5160
agaattggct tttctagcag aacctttcca aaagttttat attgagattc ataacaacac    5220
caagaattga ttttgtagcc aacattcatt caatactgtt atatcagagg agtaggagag    5280
aggaaacatt tgacttatct ggaaaagcaa aatgtactta agaataagaa taacatggtc   5340
cattcacctt tatgttatag atatgtcttt gtgtaaatca tttgttttga gttttcaaag    5400
aatagcccat tgttcattct tgtgctgtac aatgaccact gttattgtta ctttgacttt   5460
tcagagcaca cccttcctct ggttttgta tatttattga tggatcaata ataatgagga    5520
aagcatgata tgtatattgc tgagttgaaa gcacttattg gaaatatta aaggctaac    5580
attaaaagac taaggaaac agaaaaaaaa aaaaaaaa                            5619

<210> SEQ ID NO 18
<211> LENGTH: 699
```

```
<212> TYPE: PRT
<213> ORGANISM: Homo sapiens

<400> SEQUENCE: 18

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Ser Thr
    210                 215                 220

Ser Ser Asn Thr Ile Ser Ala Gly Trp Glu Pro Asn Glu Glu Asn Glu
225                 230                 235                 240

Asp Glu Arg Asp Arg His Leu Ser Phe Ser Gly Ser Gly Ile Asp Asp
                245                 250                 255

Asp Glu Asp Phe Ile Ser Ser Thr Ile Ser Thr Thr Pro Arg Ala Phe
            260                 265                 270

Asp His Thr Lys Gln Asn Gln Asp Trp Thr Gln Trp Asn Pro Ser His
        275                 280                 285

Ser Asn Pro Glu Val Leu Leu Gln Thr Thr Thr Arg Met Thr Asp Val
    290                 295                 300

Asp Arg Asn Gly Thr Thr Ala Tyr Glu Gly Asn Trp Asn Pro Glu Ala
305                 310                 315                 320

His Pro Pro Leu Ile His His Glu His His Glu Glu Glu Thr Pro
                325                 330                 335

His Ser Thr Ser Thr Ile Gln Ala Thr Pro Ser Ser Thr Thr Glu Glu
            340                 345                 350

Thr Ala Thr Gln Lys Glu Gln Trp Phe Gly Asn Arg Trp His Glu Gly
        355                 360                 365

Tyr Arg Gln Thr Pro Lys Glu Asp Ser His Ser Thr Thr Gly Thr Ala
    370                 375                 380

Ala Ala Ser Ala His Thr Ser His Pro Met Gln Gly Arg Thr Thr Pro
385                 390                 395                 400
```

Ser Pro Glu Asp Ser Ser Trp Thr Asp Phe Phe Asn Pro Ile Ser His
            405                 410                 415

Pro Met Gly Arg Gly His Gln Ala Gly Arg Arg Met Asp Met Asp Ser
        420                 425                 430

Ser His Ser Ile Thr Leu Gln Pro Thr Ala Asn Pro Asn Thr Gly Leu
    435                 440                 445

Val Glu Asp Leu Asp Arg Thr Gly Pro Leu Ser Met Thr Thr Gln Gln
450                 455                 460

Ser Asn Ser Gln Ser Phe Ser Thr Ser His Glu Gly Leu Glu Glu Asp
465                 470                 475                 480

Lys Asp His Pro Thr Thr Ser Thr Leu Thr Ser Ser Asn Arg Asn Asp
            485                 490                 495

Val Thr Gly Gly Arg Arg Asp Pro Asn His Ser Glu Gly Ser Thr Thr
        500                 505                 510

Leu Leu Glu Gly Tyr Thr Ser His Tyr Pro His Thr Lys Glu Ser Arg
    515                 520                 525

Thr Phe Ile Pro Val Thr Ser Ala Lys Thr Gly Ser Phe Gly Val Thr
530                 535                 540

Ala Val Thr Val Gly Asp Ser Asn Ser Asn Val Asn Arg Ser Leu Ser
545                 550                 555                 560

Gly Asp Gln Asp Thr Phe His Pro Ser Gly Ser His Thr Thr His
            565                 570                 575

Gly Ser Glu Ser Asp Gly His Ser His Gly Ser Gln Glu Gly Gly Ala
        580                 585                 590

Asn Thr Thr Ser Gly Pro Ile Arg Thr Pro Gln Ile Pro Glu Trp Leu
    595                 600                 605

Ile Ile Leu Ala Ser Leu Leu Ala Leu Ala Leu Ile Leu Ala Val Cys
610                 615                 620

Ile Ala Val Asn Ser Arg Arg Arg Cys Gly Gln Lys Lys Lys Leu Val
625                 630                 635                 640

Ile Asn Ser Gly Asn Gly Ala Val Glu Asp Arg Lys Pro Ser Gly Leu
            645                 650                 655

Asn Gly Glu Ala Ser Lys Ser Gln Glu Met Val His Leu Val Asn Lys
        660                 665                 670

Glu Ser Ser Glu Thr Pro Asp Gln Phe Met Thr Ala Asp Glu Thr Arg
    675                 680                 685

Asn Leu Gln Asn Val Asp Met Lys Ile Gly Val
690                 695

<210> SEQ ID NO 19
<211> LENGTH: 5001
<212> TYPE: DNA
<213> ORGANISM: Homo sapiens

<400> SEQUENCE: 19
gagaagaaag ccagtgcgtc tctgggcgca ggggccagtg gggctcggag gcacaggcac      60
cccgcgacac tccaggttcc ccgacccacg tccctggcag cccgattat ttacagcctc     120 agcagagcac ggggcggggg cagagggggcc cgcccgggag ggctgctact tcttaaaacc    180
tctgcgggct gcttagtcac agccccccctt gcttgggtgt gtccttcgct cgctccctcc   240
ctccgtctta ggtcactgtt ttcaacctcg aataaaaact gcagccaact tccgaggcag    300
cctcattgcc cagcggaccc cagcctctgc caggttcggt ccgccatcct cgtcccgtcc    360
tccgccggcc cctgccccgc gcccagggat cctccagctc ctttcgcccg cgccctccgt    420

-continued

```
tcgctccgga caccatggac aagttttggt ggcacgcagc ctggggactc tgcctcgtgc    480
cgctgagcct ggcgcagatc gatttgaata taacctgccg ctttgcaggt gtattccacg    540
tggagaaaaa tggtcgctac agcatctctc ggacggaggc cgctgacctc tgcaaggctt    600
tcaatagcac cttgcccaca atggcccaga tggagaaagc tctgagcatc ggatttgaga    660
cctgcaggta tgggttcata gaagggcacg tggtgattcc ccggatccac cccaactcca    720
tctgtgcagc aaacaacaca ggggtgtaca tcctcacatc caacacctcc cagtatgaca    780
catattgctt caatgcttca gctccacctg aagaagattg tacatcagtc acagacctgc    840
ccaatgcctt tgatggacca attaccataa ctattgttaa ccgtgatggc acccgctatg    900
tccagaaagg agaatacaga acgaatcctg aagacatcta ccccagcaac cctactgatg    960
atgacgtgag cagcggctcc tccagtgaaa ggagcagcac ttcaggaggt tacatctttt   1020 acacctttc tactgtacac cccatcccag acgaagacag tccctggatc accgacagca   1080
```
(line 1020: acacctttc tactgtacac should read acaccttttc)

```
cagacagaat ccctgctacc aatatggact ccagtcatag tataacgctt cagcctactg   1140
caaatccaaa cacaggtttg gtggaagatt tggacaggac aggacctctt tcaatgacaa   1200
cgcagcagag taattctcag agcttctcta catcacatga aggcttggaa gaagataaag   1260
accatccaac aacttctact ctgacatcaa gcaataggaa tgatgtcaca ggtggaagaa   1320
gagacccaaa tcattctgaa ggctcaacta ctttactgga aggttatacc tctcattacc   1380
cacacacgaa ggaaagcagg accttcatcc cagtgacctc agctaagact gggtcctttg   1440
gagttactgc agttactgtt ggagattcca actctaatgt caatcgttcc ttatcaggag   1500
accaagacac attccacccc agtggggggt cccataccac tcatggatct gaatcagatg   1560
gacactcaca tgggagtcaa gaaggtggag caaacacaac ctctggtcct ataaggacac   1620
cccaaattcc agaatggctg atcatcttgg catccctctt ggccttggct ttgattcttg   1680
cagtttgcat tgcagtcaac agtcgaagaa ggtgtgggca aagaaaaag ctagtgatca   1740 acagtggcaa tggagctgtg gaggacagaa agccaagtgg actcaacgga gaggccagca   1800
agtctcagga aatggtgcat ttggtgaaca aggagtcgtc agaaactcca gaccagttta   1860
tgacagctga tgagacaagg aacctgcaga atgtggacat gaagattggg gtgtaacacc   1920
tacaccatta tcttggaaag aaacaaccgt tggaaacata accattacag ggagctggga   1980
cacttaacag atgcaatgtg ctactgattg tttcattgcg aatctttttt agcataaaat   2040
tttctactct ttttgttttt tgtgttttgt tctttaaagt caggtccaat ttgtaaaaac   2100
agcattgctt tctgaaatta gggcccaatt aataatcagc aagaatttga tcgttccagt   2160
tcccacttgg aggcctttca tccctcgggt gtgctatgga tggcttctaa caaaaactac   2220
acatatgtat tcctgatcgc caacctttcc cccaccagct aaggacattt cccagggtta   2280
atagggcctg gtccctggga ggaaatttga atgggtccat tttgcccttc catagcctaa   2340
tccctgggca ttgctttcca ctgaggttgg gggttggggt gtactagtta cacatcttca   2400 acagacccc tctagaaatt tttcagatgc ttctgggaga cacccaaagg gtgaagctat   2460
ttatctgtag taaactattt atctgtgttt ttgaaatatt aaaccctgga tcagtccttt   2520
gatcagtata atttttttaaa gttactttgt cagaggcaca aaagggttta aactgattca   2580
taataaatat ctgtacttct tcgatcttca ccttttgtgc tgtgattctt cagtttctaa   2640
accagcactg tctgggtccc tacaatgtat caggaagagc tgagaatggt aaggagactc   2700
ttctaagtct tcatctcaga gaccctgagt tcccactcag acccactcag ccaaatctca   2760
```

```
tggaagacca aggagggcag cactgttttt gtttttgtt ttttgttttt ttttttgac    2820
actgtccaaa ggttttccat cctgtcctgg aatcagagtt ggaagctgag gagcttcagc   2880
ctcttttatg gtttaatggc cacctgttct ctcctgtgaa aggctttgca aagtcacatt   2940
aagtttgcat gacctgttat ccctggggcc ctatttcata gaggctggcc ctattagtga   3000
tttccaaaaa caatatggaa gtgccttttg atgtcttaca ataagagaag aagccaatgg   3060
aaatgaaaga gattggcaaa ggggaaggat gatgccatgt agatcctgtt tgacattttt   3120
atggctgtat ttgtaaactt aaacacacca gtgtctgttc ttgatgcagt tgctatttag   3180
gatgagttaa gtgcctgggg agtccctcaa aaggttaaag ggattccat cattggaatc    3240
ttatcaccag ataggcaagt ttatgaccaa acaagagagt actggcttta tcctctaacc   3300
tcatattttc tcccacttgg caagtccttt gtggcattta ttcatcagtc agggtgtccg   3360
attggtccta gaacttccaa aggctgcttg tcatagaagc cattgcatct ataaagcaac   3420
ggctcctgtt aaatggtatc tcctttctga ggctcctact aaaagtcatt tgttacctaa   3480
acttatgtgc ttaacaggca atgcttctca gaccacaaag cagaaagaag aagaaaagct   3540
cctgactaaa tcagggctgg gcttagacag agttgatctg tagaatatct ttaaaggaga   3600
gatgtcaact ttctgcacta ttcccagcct ctgctcctcc ctgtctaccc tctcccctcc   3660
ctctctccct ccacttcacc ccacaatctt gaaaaacttc ctttctcttc tgtgaacatc   3720
attggccaga tccattttca gtggtctgga tttcttttta ttttcttttc aacttgaaag   3780
aaactggaca ttaggccact atgtgttgtt actgccacta gtgttcaagt gcctcttgtt   3840
ttcccagaga tttcctgggt ctgccagagg cccagacagg ctcactcaag ctctttaact   3900
gaaaagcaac aagccactcc aggacaaggt tcaaaatggt tacaacagcc tctacctgtc   3960
gccccaggga gaaggggta gtgatacaag tctcatagcc agagatggtt ttccactcct   4020
tctagatatt cccaaaaaga ggctgagaca ggaggttatt ttcaatttta ttttggaatt   4080
aaatactttt ttcccttta tactgttgta gtccctcact tggatatacc tctgttttca   4140
cgatagaaat aagggaggtc tagagcttct attccttggc cattgtcaac ggagagctgg   4200
ccaagtcttc acaaacccct gcaacattgc ctgaagttta tggaataaga tgtattctca   4260
ctcccttgat ctcaagggcg taactctgga agcacagctt gactacacgt cattttacc    4320
aatgattttc aggtgacctg gctaagtca tttaaactgg gtcttata aagtaaaagg     4380
ccaacattta attattttgc aaagcaacct aagagctaaa gatgtaattt ttcttgcaat   4440
tgtaaatctt ttgtgtctcc tgaagacttc ccttaaaatt agctctgagt gaaaaatcaa   4500
aagagacaaa agacatcttc gaatccatat ttcaagcctg gtagaattgg cttttctagc   4560
agaacctttc caaaagtttt atattgagat tcataacaac accaagaatt gattttgtag   4620
ccaacattca ttcaatactg ttatatcaga ggagtaggag agaggaaaca tttgacttat   4680
ctggaaaagc aaaatgtact taagaataag aataacatgg tccattcacc tttatgttat   4740
agatatgtct ttgtgtaaat catttgtttt gagttttcaa agaatagccc attgttcatt   4800
cttgtgctgt acaatgacca ctgttattgt tactttgact tttcagagca cacccttcct   4860
ctggttttg tatatttatt gatggatcaa taataatgag gaaagcatga tatgtatatt    4920
gctgagttga aagcacttat tggaaaatat taaaaggcta acattaaaag actaaggaa    4980
acagaaaaaa aaaaaaaaa a                                              5001
```

<210> SEQ ID NO 20
<211> LENGTH: 493

```
<212> TYPE: PRT
<213> ORGANISM: Homo sapiens

<400> SEQUENCE: 20

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Asn Met
210                 215                 220

Asp Ser Ser His Ser Ile Thr Leu Gln Pro Thr Ala Asn Pro Asn Thr
225                 230                 235                 240

Gly Leu Val Glu Asp Leu Asp Arg Thr Gly Pro Leu Ser Met Thr Thr
                245                 250                 255

Gln Gln Ser Asn Ser Gln Ser Phe Ser Thr Ser His Glu Gly Leu Glu
            260                 265                 270

Glu Asp Lys Asp His Pro Thr Thr Ser Thr Leu Thr Ser Ser Asn Arg
        275                 280                 285

Asn Asp Val Thr Gly Gly Arg Arg Asp Pro Asn His Ser Glu Gly Ser
290                 295                 300

Thr Thr Leu Leu Glu Gly Tyr Thr Ser His Tyr Pro His Thr Lys Glu
305                 310                 315                 320

Ser Arg Thr Phe Ile Pro Val Thr Ser Ala Lys Thr Gly Ser Phe Gly
                325                 330                 335

Val Thr Ala Val Thr Val Gly Asp Ser Asn Ser Asn Val Asn Arg Ser
            340                 345                 350

Leu Ser Gly Asp Gln Asp Thr Phe His Pro Ser Gly Gly Ser His Thr
        355                 360                 365

Thr His Gly Ser Glu Ser Asp Gly His Ser His Gly Ser Gln Glu Gly
370                 375                 380

Gly Ala Asn Thr Thr Ser Gly Pro Ile Arg Thr Pro Gln Ile Pro Glu
385                 390                 395                 400
```

```
Trp Leu Ile Ile Leu Ala Ser Leu Leu Ala Leu Ala Leu Ile Leu Ala
                405                 410                 415

Val Cys Ile Ala Val Asn Ser Arg Arg Cys Gly Gln Lys Lys
            420                 425                 430

Leu Val Ile Asn Ser Gly Asn Gly Ala Val Glu Asp Arg Lys Pro Ser
            435                 440                 445

Gly Leu Asn Gly Glu Ala Ser Lys Ser Gln Glu Met Val His Leu Val
            450                 455                 460

Asn Lys Glu Ser Ser Glu Thr Pro Asp Gln Phe Met Thr Ala Asp Glu
465                 470                 475                 480

Thr Arg Asn Leu Gln Asn Val Asp Met Lys Ile Gly Val
                485                 490

<210> SEQ ID NO 21
<211> LENGTH: 4605
<212> TYPE: DNA
<213> ORGANISM: Homo sapiens

<400> SEQUENCE: 21
```

| | | | | | |
|---|---|---|---|---|---|
| gagaagaaag | ccagtgcgtc | tctgggcgca | ggggccagtg | gggctcggag | gcacaggcac | 60 |
| cccgcgacac | tccaggttcc | ccgacccacg | tccctggcag | ccccgattat | ttacagcctc | 120 |
| agcagagcac | ggggcggggg | cagaggggcc | cgcccgggag | ggctgctact | tcttaaaacc | 180 |
| tctgcgggct | gcttagtcac | agccccccctt | gcttgggtgt | gtccttcgct | cgctccctcc | 240 |
| ctccgtctta | ggtcactgtt | ttcaacctcg | aataaaaact | gcagccaact | tccgaggcag | 300 |
| cctcattgcc | cagcggaccc | cagcctctgc | caggttcggt | ccgccatcct | cgtcccgtcc | 360 |
| tccgccggcc | cctgccccgc | gcccagggat | cctccagctc | ctttcgcccg | cgccctccgt | 420 |
| tcgctccgga | caccatggac | aagttttggt | ggcacgcagc | ctggggactc | tgcctcgtgc | 480 |
| cgctgagcct | ggcgcagatc | gatttgaata | taacctgccg | ctttgcaggt | gtattccacg | 540 |
| tggagaaaaa | tggtcgctac | agcatctctc | ggacggaggc | cgctgacctc | tgcaaggctt | 600 |
| tcaatagcac | cttgcccaca | atggcccaga | tggagaaagc | tctgagcatc | ggatttgaga | 660 |
| cctgcaggta | tgggttcata | gaagggcacg | tggtgattcc | ccggatccac | cccaactcca | 720 |
| tctgtgcagc | aaacaacaca | ggggtgtaca | tcctcacatc | caacacctcc | cagtatgaca | 780 |
| catattgctt | caatgcttca | gctccacctg | aagaagattg | tacatcagtc | acagacctgc | 840 |
| ccaatgcctt | tgatggacca | attaccataa | ctattgttaa | ccgtgatggc | acccgctatg | 900 |
| tccagaaagg | agaatacaga | acgaatcctg | aagacatcta | ccccagcaac | cctactgatg | 960 |
| atgacgtgag | cagcggctcc | tccagtgaaa | ggagcagcac | ttcaggaggt | tacatctttt | 1020 |
| acaccttttc | tactgtacac | cccatcccag | acgaagacag | tccctggatc | accgacagca | 1080 |
| cagacagaat | ccctgctacc | agagaccaag | acacattcca | ccccagtggg | gggtcccata | 1140 |
| ccactcatgg | atctgaatca | gatggacact | cacatgggag | tcaagaaggt | ggagcaaaca | 1200 |
| caacctctgg | tcctataagg | acaccccaaa | ttccagaatg | gctgatcatc | ttggcatccc | 1260 |
| tcttggcctt | ggctttgatt | cttgcagttt | gcattgcagt | caacagtcga | agaaggtgtg | 1320 |
| ggcagaagaa | aaagctagtg | atcaacagtg | gcaatggagc | tgtggaggac | agaaagccaa | 1380 |
| gtggactcaa | cggagaggcc | agcaagtctc | aggaaatggt | gcatttggtg | aacaaggagt | 1440 |
| cgtcagaaac | tccagaccag | tttatgacag | ctgatgagac | aaggaacctg | cagaatgtgg | 1500 |
| acatgaagat | tggggtgtaa | cacctacacc | attatcttgg | aaagaaacaa | ccgttggaaa | 1560 |

```
cataaccatt acagggagct gggacactta acagatgcaa tgtgctactg attgtttcat   1620
tgcgaatctt ttttagcata aaattttcta ctcttttgt ttttgtgtt ttgttcttta    1680
aagtcaggtc caatttgtaa aaacagcatt gctttctgaa attagggccc aattaataat   1740
cagcaagaat ttgatcgttc cagttcccac ttggaggcct tcatcctc gggtgtgcta    1800
tggatggctt ctaacaaaaa ctacacatat gtattcctga tcgccaacct ttcccccacc   1860
agctaaggac atttcccagg gttaataggg cctggtccct ggggaaat ttgaatgggt    1920
ccattttgcc cttccatagc ctaatccctg ggcattgctt tccactgagg ttggggttg    1980
gggtgtacta gttacacatc ttcaacagac cccctctaga aatttttcag atgcttctgg   2040
gagacaccca aagggtgaag ctatttatct gtagtaaact atttatctgt gttttttgaaa  2100
tattaaaccc tggatcagtc ctttgatcag tataatttt taaagttact ttgtcagagg    2160
cacaaaaggg tttaaactga ttcataataa atatctgtac ttcttcgatc ttcacctttt   2220
gtgctgtgat tcttcagttt ctaaaccagc actgtctggg tccctacaat gtatcaggaa   2280
gagctgagaa tggtaaggag actcttctaa gtcttcatct cagagaccct gagttcccac   2340
tcagacccac tcagccaaat ctcatggaag accaaggagg gcagcactgt ttttgttttt   2400
tgttttttgt ttttttttt tgacactgtc caaaggtttt ccatcctgtc ctggaatcag    2460
agttggaagc tgaggagctt cagcctcttt tatggtttaa tggccacctg ttctctcctg   2520
tgaaaggctt tgcaaagtca cattaagttt gcatgacctg ttatccctgg ggccctattt   2580
catagaggct ggccctatta gtgatttcca aaaacaatat ggaagtgcct tttgatgtct   2640
tacaataaga gaagaagcca atggaaatga aagagattgg caaggggaa ggatgatgcc    2700
atgtagatcc tgtttgacat ttttatggct gtatttgtaa acttaaacac accagtgtct   2760
gttcttgatg cagttgctat ttaggatgag ttaagtgcct ggggagtccc tcaaaaggtt   2820
aaagggattc ccatcattgg aatcttatca ccagataggc aagtttatga ccaaacaaga   2880
gagtactggc tttatcctct aacctcatat tttctcccac ttggcaagtc ctttgtggca   2940
tttattcatc agtcagggtg tccgattggt cctagaactt ccaaaggctg cttgtcatag   3000
aagccattgc atctataaag caacggctcc tgttaaatgg tatctccttt ctgaggctcc   3060
tactaaaagt catttgttac ctaaacttat gtgcttaaca ggcaatgctt ctcagaccac   3120
aaagcagaaa gaagaagaaa agctcctgac taaatcaggg ctgggcttag acagagttga   3180
tctgtagaat atctttaaag gagagatgtc aactttctgc actattccca gcctctgctc   3240
ctccctgtct accctctccc ctccctctct ccctccactt caccccacaa tcttgaaaaa   3300
cttcctttct cttctgtgaa catcattggc cagatccatt ttcagtggtc tggatttctt   3360
tttatttct tttcaacttg aaagaaactg gacattaggc cactatgtgt tgttactgcc    3420
actagtgttc aagtgcctct tgttttccca gagatttcct gggtctgcca gaggcccaga   3480
caggctcact caagctcttt aactgaaaag caacaagcca ctccaggaca aggttcaaaa   3540
tggttacaac agcctctacc tgtcgcccca gggagaaagg ggtagtgata caagtctcat   3600
agccagagat ggttttccac tccttctaga tattcccaaa aagaggctga acaggaggt    3660
tattttcaat tttatttgg aattaaatac tttttccct ttattactgt tgtagtccct     3720
cacttggata tacctctgtt ttcacgatag aaataaggga ggtctagagc ttctattcct   3780
tggccattgt caacggagag ctggccaagt cttcacaaac ccttgcaaca ttgcctgaag   3840
tttatggaat aagatgtatt ctcactccct tgatctcaag gcgtaactc tggaagcaca    3900
gcttgactac acgtcatttt taccaatgat tttcaggtga cctgggctaa gtcatttaaa   3960
```

-continued

```
ctgggtcttt ataaaagtaa aaggccaaca tttaattatt ttgcaaagca acctaagagc    4020
taaagatgta attttcttg caattgtaaa tcttttgtgt ctcctgaaga cttcccttaa     4080
aattagctct gagtgaaaaa tcaaaagaga caaaagacat cttcgaatcc atatttcaag    4140
cctggtagaa ttggcttttc tagcagaacc tttccaaaag ttttatattg agattcataa    4200
caacaccaag aattgatttt gtagccaaca ttcattcaat actgttatat cagaggagta    4260
ggagagagga aacatttgac ttatctggaa aagcaaaatg tacttaagaa taagaataac    4320
atggtccatt caccttatg ttatagatat gtctttgtgt aaatcatttg ttttgagttt     4380
tcaaagaata gcccattgtt cattcttgtg ctgtacaatg accactgtta ttgttacttt    4440
gacttttcag agcacaccct tcctctggtt tttgtatatt tattgatgga tcaataataa    4500
tgaggaaagc atgatatgta tattgctgag ttgaaagcac ttattggaaa atattaaaag    4560
gctaacatta aaagactaaa ggaaacagaa aaaaaaaaa aaaaa                     4605
```

<210> SEQ ID NO 22
<211> LENGTH: 361
<212> TYPE: PRT
<213> ORGANISM: Homo sapiens

<400> SEQUENCE: 22

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Arg Asp
    210                 215                 220

Gln Asp Thr Phe His Pro Ser Gly Gly Ser His Thr Thr His Gly Ser
225                 230                 235                 240

Glu Ser Asp Gly His Ser His Gly Ser Gln Glu Gly Gly Ala Asn Thr
                245                 250                 255
```

```
       Thr Ser Gly Pro Ile Arg Thr Pro Gln Ile Pro Glu Trp Leu Ile Ile
               260                 265                 270

Leu Ala Ser Leu Leu Ala Leu Ala Leu Ile Leu Ala Val Cys Ile Ala
                   275                 280                 285

Val Asn Ser Arg Arg Arg Cys Gly Gln Lys Lys Leu Val Ile Asn
               290                 295                 300

Ser Gly Asn Gly Ala Val Glu Asp Arg Lys Pro Ser Gly Leu Asn Gly
       305                 310                 315                 320

Glu Ala Ser Lys Ser Gln Glu Met Val His Leu Val Asn Lys Glu Ser
                       325                 330                 335

Ser Glu Thr Pro Asp Gln Phe Met Thr Ala Asp Glu Thr Arg Asn Leu
                   340                 345                 350

Gln Asn Val Asp Met Lys Ile Gly Val
                   355                 360

<210> SEQ ID NO 23
<211> LENGTH: 3985
<212> TYPE: DNA
<213> ORGANISM: Homo sapiens

<400> SEQUENCE: 23
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agcccccctt gcttgggtgt gtccttcgct cgctccctcc     240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagttttggt ggcacgcagc ctgggactc tgcctcgtgc      480
cgctgagcct ggcgcagatc gatttgaata taacctgccg ctttgcaggt gtattccacg     540
tggagaaaaa tggtcgctac agcatctctc ggacggaggc cgctgacctc tgcaaggctt     600
tcaatagcac cttgcccaca atggcccaga tggagaaagc tctgagcatc ggatttgaga     660
cctgcagttt gcattgcagt caacagtcga agaaggtgtg ggcagaagaa aaagctagtg     720
atcaacagtg gcaatggagc tgtggaggac agaaagccaa gtggactcaa cggagaggcc     780
agcaagtctc aggaaatggt gcatttggtg aacaaggagt cgtcagaaac tccagaccag     840
tttatgacag ctgatgagac aaggaacctg cagaatgtgg acatgaagat tggggtgtaa     900
cacctacacc attatcttgg aaagaaacaa ccgttggaaa cataaccatt acagggagct     960
gggacactta acagatgcaa tgtgctactg attgtttcat tgcgaatctt ttttagcata    1020
aaattttcta ctcttttgt ttttttgtgtt ttgttcttta aagtcaggtc caatttgtaa    1080
aaacagcatt gctttctgaa attagggccc aattaataat cagcaagaat ttgatcgttc    1140
cagttcccac ttggaggcct ttcatccctc gggtgtgcta tggatggctt ctaacaaaaa    1200
ctacacatat gtattcctga tcgccaacct ttcccccacc agctaaggac atttcccagg    1260
gttaataggg cctggtccct gggaggaaat ttgaatgggt ccattttgcc cttccatagc    1320
ctaatccctg ggcattgctt tccactgagg ttgggggttg gggtgtacta gttacacatc    1380
ttcaacagac cccctctaga aattttcag atgcttctgg gagacaccca aagggtgaag     1440
ctatttatct gtagtaaact atttatctgt gttttttgaaa tattaaaccc tggatcagtc    1500
```

```
ctttgatcag tataatttttt taaagttact ttgtcagagg cacaaaaggg tttaaactga    1560
ttcataataa atatctgtac ttcttcgatc ttcacctttt gtgctgtgat tcttcagttt    1620
ctaaaccagc actgtctggg tccctacaat gtatcaggaa gagctgagaa tggtaaggag    1680
actcttctaa gtcttcatct cagagaccct gagttcccac tcagacccac tcagccaaat    1740
ctcatggaag accaaggagg gcagcactgt ttttgttttt tgtttttgt ttttttttt     1800 tgacactgtc caaaggtttt ccatcctgtc ctggaatcag agttggaagc tgaggagctt    1860
cagcctcttt tatggtttaa tggccacctg ttctctcctg tgaaaggctt gcaaagtca     1920 cattaagttt gcatgacctg ttatccctgg ggccctattt catagaggct ggccctatta    1980
gtgatttcca aaacaatat ggaagtgcct tttgatgtct acaataaga gaagaagcca      2040 atggaaatga aagagattgg caaaggggaa ggatgatgcc atgtagatcc tgtttgacat    2100
ttttatggct gtatttgtaa acttaaacac accagtgtct gttcttgatg cagttgctat    2160
ttaggatgag ttaagtgcct ggggagtccc tcaaaaggtt aaaggattc ccatcattgg     2220 aatcttatca ccagataggc aagtttatga ccaaacaaga gagtactggc tttatcctct    2280
aacctcatat tttctcccac ttggcaagtc ctttgtggca tttattcatc agtcagggtg    2340
tccgattggt cctagaactt ccaaaggctg cttgtcatag aagccattgc atctataaag    2400
caacggctcc tgttaaatgg tatctccttt ctgaggctcc tactaaaagt catttgttac    2460
ctaaacttat gtgcttaaca ggcaatgctt ctcagaccac aaagcagaaa gaagaagaaa    2520
agctcctgac taaatcaggg ctgggcttag acagagttga tctgtagaat atctttaaag    2580
gagagatgtc aactttctgc actattccca gcctctgctc ctccctgtct accctctccc    2640
ctccctctct ccctccactt cacccccacaa tcttgaaaaa cttcctttct cttctgtgaa   2700
catcattggc cagatccatt ttcagtggtc tggatttctt tttattttct tttcaacttg    2760
aaagaaactg gacattaggc cactatgtgt tgttactgcc actagtgttc aagtgcctct    2820
tgttttccca gagatttcct gggtctgcca gaggcccaga caggctcact caagctcttt    2880
aactgaaaag caacaagcca ctccaggaca aggttcaaaa tggttacaac agcctctacc    2940
tgtcgcccca gggagaaagg ggtagtgata caagtctcat agccagagat ggttttccac    3000
tccttctaga tattcccaaa aagaggctga gacaggaggt tattttcaat tttattttgg    3060
aattaaatac tttttttccct ttattactgt tgtagtccct cacttggata tacctctgtt   3120
ttcacgatag aaataaggga ggtctagagc ttctattcct tggccattgt caacggagag    3180
ctggccaagt cttcacaaac ccttgcaaca ttgcctgaag tttatggaat aagatgtatt    3240
ctcactccct tgatctcaag ggcgtaactc tggaagcaca gcttgactac acgtcatttt    3300
taccaatgat tttcaggtga cctgggctaa gtcatttaaa ctgggtcttt ataaaagtaa    3360
aaggccaaca tttaattatt ttgcaaagca acctaagagc taaagatgta atttttcttg    3420
caattgtaaa tcttttgtgt ctcctgaaga cttcccttaa aattagctct gagtgaaaaa    3480
tcaaaagaga caaagacat cttcgaatcc atatttcaag cctggtagaa ttggcttttc     3540
tagcagaacc tttccaaaag tttttatattg agattcataa caacaccaag aattgatttt   3600
gtagccaaca ttcattcaat actgttatat cagaggagta ggagagagga aacatttgac    3660
ttatctggaa aagcaaaatg tacttaagaa taagaataac atggtccatt caccctttatg   3720 ttatagatat gtcttttgtgt aaatcatttg ttttgagttt tcaaagaata gcccattgtt    3780
cattcttgtg ctgtacaatg accactgtta ttgttacttt gacttttcag agcacaccct    3840
tcctctggtt tttgtatatt tattgatgga tcaataataa tgaggaaagc atgatatgta    3900
```

```
tattgctgag ttgaaagcac ttattggaaa atattaaaag gctaacatta aaagactaaa    3960
ggaaacagaa aaaaaaaaaa aaaaa                                          3985

<210> SEQ ID NO 24
<211> LENGTH: 139
<212> TYPE: PRT
<213> ORGANISM: Homo sapiens

<400> SEQUENCE: 24

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Ser Leu His
65                  70                  75                  80

Cys Ser Gln Gln Ser Lys Lys Val Trp Ala Glu Lys Ala Ser Asp
                85                  90                  95

Gln Gln Trp Gln Trp Ser Cys Gly Gly Gln Lys Ala Lys Trp Thr Gln
            100                 105                 110

Arg Arg Gly Gln Gln Val Ser Gly Asn Gly Ala Phe Gly Glu Gln Gly
        115                 120                 125

Val Val Arg Asn Ser Arg Pro Val Tyr Asp Ser
    130                 135

<210> SEQ ID NO 25
<211> LENGTH: 4350
<212> TYPE: DNA
<213> ORGANISM: Homo sapiens

<400> SEQUENCE: 25
agttgaggga ttgacacaaa tggtcaggcg gcggcggcgg agaaggaggc ggaggcgcag     60
gggggagccg agcccgctgg gctgcggaga gttgcgctct ctacgggccc gcggccacta    120
gcgcggcgcc gccagccggg agccagcgag ccgagggcca ggaaggcggg acacgacccc    180
ggcgcgccct agccacccgg gttctccccg ccgcccgcgc ttcatgaatc gcaagtttcc    240 gcggcggcg cggctgcggt acgcagaaca ggagccgggg gagcgggccg aaagcggctt     300
gggctcgacg gagggcaccc gcgcagaggt ctccctggcc gcaggggag ccgccgccgg     360 ccgtgccccc ggcagcccca gcggagcggc gccaagagag gagccgagaa agtatggctg    420
aggaggaggc gcctaagaag tcccgggccg ccggcggtgg cgcgagctgg gaactttgtg    480
ccggggcgct ctcggcccgg ctggcggagg agggcagcgg ggacgccggt ggccgccgcc    540
gcccgccagt tgaccccggc gattggcgc gccagctgct gctgctgctt tggctgctgg     600
aggctccgct gctgctgggg gtccgggccc aggcggcggg ccaggggcca ggccaggggc    660
ccgggccggg gcagcaaccg ccgccgccgc ctcagcagca acagagcggg cagcagtaca    720
acggcgagcg gggcatctcc gtcccggacc acggctattg ccagcccatc tccatcccgc    780
tgtgcacgga catcgcgtac aaccagacca tcatgcccaa cctgctgggc cacacgaacc    840
aggaggacgc gggcctggag gtgcaccagt tctaccctct agtgaaagtg cagtgttccg    900
ctgagctcaa gttcttcctg tgctccatgt acgcgcccgt gtgcaccgtg ctagagcagg    960
```

```
cgctgccgcc ctgccgctcc ctgtgcgagc gcgcgcgcca gggctgcgag gcgctcatga    1020
acaagttcgg cttccagtgg ccagacacgc tcaagtgtga aagttcccg gtgcacggcg     1080 ccggcgagct gtgcgtgggc cagaacacgt ccgacaaggg caccccgacg ccctcgctgc    1140
ttccagagtt ctggaccagc aaccctcagc acggcggcgg agggcaccgt ggcggcttcc    1200
cggggggcgc cggcgcgtcg gagcgaggca agttctcctg cccgcgcgcc ctcaaggtgc    1260
cctcctacct caactaccac ttcctggggg agaaggactg cggcgcacct tgtgagccga    1320
ccaaggtgta tggctcatg tacttcgggc ccgaggagct gcgcttctcg cgcacctgga    1380
ttggcatttg gtcagtgctg tgctgcgcct ccacgctctt cacggtgctt acgtacctgg    1440
tggacatgcg gcgcttcagc tacccggagc ggcccatcat cttcttgtcc ggctgttaca    1500
cggccgtggc cgtggcctac atcgccggct tcctcctgga agaccgagtg gtgtgtaatg    1560
acaagttcgc cgaggacggg gcacgcactg tggcgcaggg caccaagaag agggctgca    1620 ccatcctctt catgatgctc tacttcttca gcatggccag ctccatctgg tgggtgatcc    1680
tgtcgctcac ctggttcctg gcggctggca tgaagtgggg ccacgaggcc atcgaagcca    1740
actcacagta ttttcacctg gccgcctggg ctgtgccggc catcaagacc atcaccatcc    1800
tggcgctggg ccaggtggac ggcgatgtgc tgagcggagt gtgcttcgtg gggcttaaca    1860
acgtggacgc gctgcgtggc ttcgtgctgg cgcccctctt cgtgtacctg tttatcggca    1920
cgtcctttct gctggccggc tttgtgtcgc tcttccgcat ccgcaccatc atgaagcacg    1980
atggcaccaa gaccgagaag ctggagaagc tcatggtgcg cattggcgtc ttcagcgtgc    2040
tgtacactgt gccagccacc atcgtcatcg cctgctactt ctacgagcag gccttccggg    2100
accagtggga acgcagctgg gtggcccaga gctgcaagag ctacgctatc ccctgccctc    2160
acctccaggc gggcggaggc gccccgccgc acccgcccat gagcccggac ttcacggtct    2220
tcatgattaa gtaccttatg acgctgatcg tgggcatcac gtcgggcttc tggatctggt    2280
ccggcaagac cctcaactcc tggaggaagt tctacacgag gctcaccaac agcaaacaag    2340
gggagactac agtctgagac ccggggctca gcccatgccc aggcctcggc cggggcgcag    2400
cgatccccca aagccagcgc cgtggagttc gtgccaatcc tgacatctcg aggtttcctc    2460
actagacaac tctcttttcg caggctccttt gaacaactca gctcctgcaa aagcttccgt    2520
ccctgaggca aaaggacacg agggcccgac tgccagaggg aggatggaca gacctcttgc    2580
cctcacactc tggtaccagg actgttcgct tttatgattg taaatagcct gtgtaagatt    2640
tttgtaagta tatttgtatt taaatgacga ccgatcacgc gttttctttt tcaaaagtt    2700 tttaattatt tagggcggtt taaccatttg aggcttttcc ttcttgccct tttcggagta    2760
ttgcaaagga gctaaaactg gtgtgcaacc gcacagcgct cctggtcgtc ctcgcgcgcc    2820
tctccctacc acgggtgctc gggacggctg ggcgccagct ccggggcgag ttcagcactg    2880
cggggtgcga ctagggctgc gctgccaggg tcacttcccg cctcctcctt ttgccccctc    2940 ccctccttc tgtcccctcc ctttctttcc tggcttgagg taggggctct taaggtacag    3000
aactccacaa accttccaaa tctggaggag ggccccata cattacaatt cctcccttgc    3060
tcggcggtgg attgcgaagg cccgtccctt cgacttcctg aagctggatt tttaactgtc    3120
cagaactttc ctccaacttc atgggggccc acgggtgtgg gcgctggcag tctcagcctc    3180
cctccacggt caccttcaac gcccagacac tccttctcc cacctagtt ggttacaggg    3240 tgagtgagat aaccaatgcc aaactttttg aagtctaatt tttgaggggt gagctcattt    3300
```

```
cattctctag tgtctaaaac ctggtatggg tttggccagc gtcatggaaa gatgtggtta    3360
ctgagatttg ggaagaagca tgaagctttg tgtgggttgg aagagactga agatatgggt    3420
tataaaatgt taattctaat tgcatacgga tgcctggcaa ccttgccttt gagaatgaga    3480
cagcctgcgc ttagattta ccggtctgta aatggaaat gttgaggtca ctggaaagc      3540 tttgttaagg agttgatgtt tgctttcctt aacaagacag caaaacgtaa acagaaattg    3600
aaaacttgaa ggatatttca gtgtcatgga cttcctcaaa atgaagtgct atttcttat    3660 ttttaatcaa ataactagac atatatcaga aactttaaaa tgtaaaagtt gtacactttc    3720 aacatttat tacgattatt attcagcagc acattctgag gggggaacaa ttcacaccac    3780
caataataac ctggtaagat ttcaggaggt aaagaaggtg gaataattga cggggagata    3840
gcgcctgaaa taaacaaaat atgggcatgc atgctaaagg gaaatgtgt gcaggtctac     3900 tgcattaaat cctgtgtgct cctcttttgg atttacagaa atgtgtcaaa tgtaaatctt    3960
tcaaagccat ttaaaaatat tcactttagt tctctgtgaa gaagaggaga aaagcaatcc    4020
tcctgattgt attgttttaa actttaagaa tttatcaaaa tgccggtact taggacctaa    4080
atttatctat gtctgtcata cgctaaaatg atattggtct ttgaatttgg tatacattta    4140
ttctgttcac tatcacaaaa tcatctatat ttatagagga atagaagttt atatatatat    4200
aataccatat ttttaattc acaaataaaa aattcaaagt tttgtacaaa attatatgga    4260
ttttgtgcct gaaataata gagcttgagc tgtctgaact attttacatt ttatggtgtc    4320
tcatagccaa tcccacagtg taaaaattca                                     4350
```

<210> SEQ ID NO 26
<211> LENGTH: 647
<212> TYPE: PRT
<213> ORGANISM: Homo sapiens

<400> SEQUENCE: 26

```
Met Ala Glu Glu Glu Ala Pro Lys Lys Ser Arg Ala Ala Gly Gly Gly
 1               5                  10                  15

Ala Ser Trp Glu Leu Cys Ala Gly Ala Leu Ser Ala Arg Leu Ala Glu
            20                  25                  30

Glu Gly Ser Gly Asp Ala Gly Gly Arg Arg Pro Pro Val Asp Pro
        35                  40                  45

Arg Arg Leu Ala Arg Gln Leu Leu Leu Leu Trp Leu Leu Glu Ala
    50                  55                  60

Pro Leu Leu Leu Gly Val Arg Ala Gln Ala Ala Gly Gln Gly Pro Gly
65                  70                  75                  80

Gln Gly Pro Gly Pro Gly Gln Gln Pro Pro Pro Gln Gln Gln
            85                  90                  95

Gln Ser Gly Gln Gln Tyr Asn Gly Glu Arg Gly Ile Ser Val Pro Asp
           100                 105                 110

His Gly Tyr Cys Gln Pro Ile Ser Ile Pro Leu Cys Thr Asp Ile Ala
       115                 120                 125

Tyr Asn Gln Thr Ile Met Pro Asn Leu Leu Gly His Thr Asn Gln Glu
   130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
               165                 170                 175

Cys Thr Val Leu Glu Gln Ala Leu Pro Pro Cys Arg Ser Leu Cys Glu
           180                 185                 190
```

-continued

```
Arg Ala Arg Gln Gly Cys Glu Ala Leu Met Asn Lys Phe Gly Phe Gln
        195                 200                 205
Trp Pro Asp Thr Leu Lys Cys Glu Lys Phe Pro Val His Gly Ala Gly
210                 215                 220
Glu Leu Cys Val Gly Gln Asn Thr Ser Asp Lys Gly Thr Pro Thr Pro
225                 230                 235                 240
Ser Leu Leu Pro Glu Phe Trp Thr Ser Asn Pro Gln His Gly Gly Gly
                245                 250                 255
Gly His Arg Gly Gly Phe Pro Gly Gly Ala Gly Ala Ser Glu Arg Gly
            260                 265                 270
Lys Phe Ser Cys Pro Arg Ala Leu Lys Val Pro Ser Tyr Leu Asn Tyr
        275                 280                 285
His Phe Leu Gly Glu Lys Asp Cys Gly Ala Pro Cys Glu Pro Thr Lys
    290                 295                 300
Val Tyr Gly Leu Met Tyr Phe Gly Pro Glu Glu Leu Arg Phe Ser Arg
305                 310                 315                 320
Thr Trp Ile Gly Ile Trp Ser Val Leu Cys Cys Ala Ser Thr Leu Phe
                325                 330                 335
Thr Val Leu Thr Tyr Leu Val Asp Met Arg Arg Phe Ser Tyr Pro Glu
            340                 345                 350
Arg Pro Ile Ile Phe Leu Ser Gly Cys Tyr Thr Ala Val Ala Val Ala
        355                 360                 365
Tyr Ile Ala Gly Phe Leu Leu Glu Asp Arg Val Val Cys Asn Asp Lys
    370                 375                 380
Phe Ala Glu Asp Gly Ala Arg Thr Val Ala Gln Gly Thr Lys Lys Glu
385                 390                 395                 400
Gly Cys Thr Ile Leu Phe Met Met Leu Tyr Phe Phe Ser Met Ala Ser
                405                 410                 415
Ser Ile Trp Trp Val Ile Leu Ser Leu Thr Trp Phe Leu Ala Ala Gly
            420                 425                 430
Met Lys Trp Gly His Glu Ala Ile Glu Ala Asn Ser Gln Tyr Phe His
        435                 440                 445
Leu Ala Ala Trp Ala Val Pro Ala Ile Lys Thr Ile Thr Ile Leu Ala
    450                 455                 460
Leu Gly Gln Val Asp Gly Asp Val Leu Ser Gly Val Cys Phe Val Gly
465                 470                 475                 480
Leu Asn Asn Val Asp Ala Leu Arg Gly Phe Val Leu Ala Pro Leu Phe
                485                 490                 495
Val Tyr Leu Phe Ile Gly Thr Ser Phe Leu Leu Ala Gly Phe Val Ser
            500                 505                 510
Leu Phe Arg Ile Arg Thr Ile Met Lys His Asp Gly Thr Lys Thr Glu
        515                 520                 525
Lys Leu Glu Lys Leu Met Val Arg Ile Gly Val Phe Ser Val Leu Tyr
    530                 535                 540
Thr Val Pro Ala Thr Ile Val Ile Ala Cys Tyr Phe Tyr Glu Gln Ala
545                 550                 555                 560
Phe Arg Asp Gln Trp Glu Arg Ser Trp Val Ala Gln Ser Cys Lys Ser
                565                 570                 575
Tyr Ala Ile Pro Cys Pro His Leu Gln Ala Gly Gly Gly Ala Pro Pro
            580                 585                 590
His Pro Pro Met Ser Pro Asp Phe Thr Val Phe Met Ile Lys Tyr Leu
        595                 600                 605
```

```
Met Thr Leu Ile Val Gly Ile Thr Ser Gly Phe Trp Ile Trp Ser Gly
    610                 615                 620

Lys Thr Leu Asn Ser Trp Arg Lys Phe Tyr Thr Arg Leu Thr Asn Ser
625                 630                 635                 640

Lys Gln Gly Glu Thr Thr Val
                645
```

<210> SEQ ID NO 27
<211> LENGTH: 1203
<212> TYPE: DNA
<213> ORGANISM: Homo sapiens

<400> SEQUENCE: 27

```
gtggaaattg aggggagaaa aaaaaaggga aaaaaagggt ctgtccttcc tgggattcct      60
agccgaggcc agtctgctgc cgtgtgcgtg tgcgtcaggg ctctccgggc ggcaatgggg     120
gcttgagagc cggtccccac gcgcggaa ggagcgcgg tggccgccac cgccaccgcc        180
ccggagtccg gcgccgaagc tgcgggcggg cgggcgggca ccagctcggt caggggctgc     240
ttggcgcggc actgtgcggt gcagcggcgg cgcggcgcgg tgcgggcttt tcccaggcgc     300
cccggggtcg ggtggccaac ggcgcggccg cgggcgctga gcgcgaccgg ttcgcggtag     360
cggtggcggc ggcgtgcgtg ccaggggctg ggggctccgc cgcctctctt gcggctcacc     420
gagctccgcg cttccctctc tccagggcag gcggcttctc agagcacaac agctccagct     480
ggcagcatca cttcccgcca atttatccaa cttctgccaa ggctctgaaa tgccaacaac     540
gtcgaggcct gcacttgatg tcaagggtgg cacctcacct gcgaaggagg atgccaacca     600
agagatgagc tccgtggcct actccaacct tgcggtgaaa gatcgcaaag cagtggccat     660
tctgcactac cctggggtag cctcaaatgg aaccaaggcc agtggggctc ccactagttc     720
ctcgggatct ccaataggct ctcctacaac caccctccc actaaacccc catccttcaa      780
cctgcacccc gcccctcact tgctggctag tatgcagctg cagaaactta atagccagta     840
tcagggggatg gctgctgcca ctccaggcca acccggggag gcaggacccc tgcaaaactg    900
ggactttggg gcccaggcgg gaggggcaga atcactctct ccttctgctg gtgcccagag     960
ccctgctatc atcgattcgg acccagtgga tgaggaagtg ctgatgtcgc tggtggtgga    1020
actggggttg gaccgagcca atgagcttcc ggagctgtgg ctgggcaga atgagtttga    1080
cttcactgcg gactttccat ctagctgcta atgccaagtg tccctaaaga tggaggaata    1140
aagccaccaa ttctgttgta aataaaaata aagttactta caaaaaaaaa aaaaaaaaa    1200
aaa                                                                  1203
```

<210> SEQ ID NO 28
<211> LENGTH: 193
<212> TYPE: PRT
<213> ORGANISM: Homo sapiens

<400> SEQUENCE: 28

```
Met Pro Thr Thr Ser Arg Pro Ala Leu Asp Val Lys Gly Gly Thr Ser
1               5                   10                  15

Pro Ala Lys Glu Asp Ala Asn Gln Glu Met Ser Ser Val Ala Tyr Ser
                20                  25                  30

Asn Leu Ala Val Lys Asp Arg Lys Ala Val Ala Ile Leu His Tyr Pro
            35                  40                  45

Gly Val Ala Ser Asn Gly Thr Lys Ala Ser Gly Ala Pro Thr Ser Ser
        50                  55                  60
```

```
Ser Gly Ser Pro Ile Gly Ser Pro Thr Thr Thr Pro Pro Thr Lys Pro
 65                  70                  75                  80

Pro Ser Phe Asn Leu His Pro Ala Pro His Leu Leu Ala Ser Met Gln
                 85                  90                  95

Leu Gln Lys Leu Asn Ser Gln Tyr Gln Gly Met Ala Ala Ala Thr Pro
            100                 105                 110

Gly Gln Pro Gly Glu Ala Gly Pro Leu Gln Asn Trp Asp Phe Gly Ala
        115                 120                 125

Gln Ala Gly Gly Ala Glu Ser Leu Ser Pro Ser Ala Gly Ala Gln Ser
    130                 135                 140

Pro Ala Ile Ile Asp Ser Asp Pro Val Asp Glu Val Leu Met Ser
145                 150                 155                 160

Leu Val Val Glu Leu Gly Leu Asp Arg Ala Asn Glu Leu Pro Glu Leu
                165                 170                 175

Trp Leu Gly Gln Asn Glu Phe Asp Phe Thr Ala Asp Phe Pro Ser Ser
                180                 185                 190

Cys

<210> SEQ ID NO 29
<211> LENGTH: 1642
<212> TYPE: DNA
<213> ORGANISM: Homo sapiens

<400> SEQUENCE: 29
gctctgcgtt gggccagccc ctcacagctg gtttcttacc acgtattgcg caagcggaat      60
ctatgcctgt tacccacact ccctgcgccc ccgcaccccg ctcctgtgcg caagtcggaa     120
tataaaaccg cggaggagtg agctcttggg gtgtccagtt ggttgccgcg gcagtctctc     180
cgagcagcgc atttgtcttc taggctgctt ggttcgtgcc tccgagaaag gggtctcctg     240
ctgccagcta agtgtgggag aacttgtgca cgtatctccc ctccgaatcc caacgatggg     300
taacgccagc tttggctcca aggaacagaa gctgctgaag cggttgcggc ttctgcccgc     360
cctgcttatc ctccgcgcct tcaagcccca caggaagatc agagattacc gcgtcgtggt     420
agtcggcacc gctggtgtgg ggaaaagtac gctgctgcac aagtgggcga gcggcaactt     480
ccgtcatgag tacctgccga ccattgaaaa tacctactgc cagttgctgg gctgcagcca     540
cggtgtgctt tccctgcaca tcaccgacag caagagtggc gacggcaacc gcgctctgca     600
gcgccacgtt atagcccggg gccacgcctt cgtcctggtc tactcagtca ccaagaagga     660
aaccctggaa gagctgaagg ccttctatga gctgatctgc aagatcaaag gtaacaacct     720
gcataagttc cccatcgtgc tggtgggcaa taaaagtgat gacacccacc gggaggtggc     780
cctgaatgat ggtgccacct gtgcgatgga gtggaattgc gccttcatgg agatttcagc     840
caagaccgat gtgaatgtgc aggagctgtt ccacatgctg ctgaattaca gaaaaagcc     900 caccaccggc ctccaggagc ccgagaagaa atcccagatg cccaacacca ctgagaagct     960
gcttgacaag tgcataatca tgtgagcccct gggccttaag agccagctct tcctatcctg    1020
tagcgtgtag aaaacgtgga ctcatttcac tatgttacat gtacatggtt gattttgtgc    1080
tgttgtttgg actgtaacat ccatgttgtc aatacgtata ccttgtaagt ggataacttt    1140 tcttttttccc aggccagaga attcaaattg ttaaaacatt ggcatttgaa gaggagaaca    1200
aaatgtagca tgatgtattt aaagtaaggc ctttagtaat gaatgtaatg agagaaaatg    1260
ttttgaaaag aacaaaacat caaaatgaat agaaagaaaa attggaaggc gtcctttttgg    1320 taacccgatt attgtgtatt accttttaaat atttcacatc ctgtaagtgc ttaatcatat    1380
```

```
cttttaattg tgtatttaag aaaagtgttt tcacaacaaa agcttttgat aaattgctgc    1440
gtgacatata ctaaataaaa aaatgaatat gttgatcatt aggggtgtgg gagcagagaa    1500
aattgtgaaa gtgactctca ctaaagatgt tagtagtttc tcatgtcatt taaaaatgtt    1560
tgagtattct gcatagcagt ttgtaaaagt gtaacagctt attgacttaa taaagctttt    1620
cctgcatgca aaaaaaaaaa aa                                              1642

<210> SEQ ID NO 30
<211> LENGTH: 229
<212> TYPE: PRT
<213> ORGANISM: Homo sapiens

<400> SEQUENCE: 30

Met Gly Asn Ala Ser Phe Gly Ser Lys Glu Gln Lys Leu Leu Lys Arg
1               5                   10                  15

Leu Arg Leu Leu Pro Ala Leu Leu Ile Leu Arg Ala Phe Lys Pro His
            20                  25                  30

Arg Lys Ile Arg Asp Tyr Arg Val Val Val Gly Thr Ala Gly Val
        35                  40                  45

Gly Lys Ser Thr Leu Leu His Lys Trp Ala Ser Gly Asn Phe Arg His
    50                  55                  60

Glu Tyr Leu Pro Thr Ile Glu Asn Thr Tyr Cys Gln Leu Leu Gly Cys
65                  70                  75                  80

Ser His Gly Val Leu Ser Leu His Ile Thr Asp Ser Lys Ser Gly Asp
                85                  90                  95

Gly Asn Arg Ala Leu Gln Arg His Val Ile Ala Arg Gly His Ala Phe
            100                 105                 110

Val Leu Val Tyr Ser Val Thr Lys Glu Thr Leu Glu Glu Leu Lys
            115                 120                 125

Ala Phe Tyr Glu Leu Ile Cys Lys Ile Lys Gly Asn Asn Leu His Lys
    130                 135                 140

Phe Pro Ile Val Leu Val Gly Asn Lys Ser Asp Asp Thr His Arg Glu
145                 150                 155                 160

Val Ala Leu Asn Asp Gly Ala Thr Cys Ala Met Glu Trp Asn Cys Ala
                165                 170                 175

Phe Met Glu Ile Ser Ala Lys Thr Asp Val Asn Val Gln Glu Leu Phe
            180                 185                 190

His Met Leu Leu Asn Tyr Lys Lys Pro Thr Thr Gly Leu Gln Glu
        195                 200                 205

Pro Glu Lys Lys Ser Gln Met Pro Asn Thr Thr Glu Lys Leu Leu Asp
    210                 215                 220

Lys Cys Ile Ile Met
225

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggctgcttt taactctggt aa                                              22

<210> SEQ ID NO 32
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atgggtggaa tcatattgga ac                                              22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtcatactc ctgcttgctg                                                 20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccagatcatt gctcctcctg a                                               21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cacttgtgat gccctgactg                                                 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acggtactgc tgcaggctat                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caaccagagc tgggaagatt                                                 20

<210> SEQ ID NO 38
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agagatacgc aggtgcaggt                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gccatggtga aaatggctaa                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gagtgtcagc accaacttgc                                              20
```

METHOD FOR DIFFERENTIATING MALIGNANT FROM BENIGN THYROID TISSUE

CROSS REFERENCE TO RELATED APPLICATIONS

This application claims priority to and any other benefit of U.S. Provisional Application Ser. No. 60/773,477, filed on Feb. 15, 2006, the entire content of which is incorporated by reference herein.

GOVERNMENT RIGHTS

Work leading to this invention was supported at least in part by National Cancer Institute grants CA16058 and CA16059. The government has certain rights in this invention.

FIELD OF THE INVENTION

This invention generally relates to tests for determining whether tissue is malignant. In particular, the tests relate to thyroid tissue, and more particularly, to thyroid nodules. The tests generally involve testing for the expression of two or more of the three genes identified and known in the art as CCND2, PCSK2, and PLAB. In some embodiments, the testing involves assaying for the expression of at least two of the three, and in other embodiments, the testing involves assaying for the expression of all three. The test involves measuring and comparing the relative expression levels of the genes in sample tissues and in normal or non-malignant thyroid tissues ("controls"), wherein differences between the expression levels of the genes indicative of the presence or absence of malignancy.

BACKGROUND OF THE INVENTION

Thyroid cancer derived from the follicular epithelial cell is the most common endocrine cancer. Papillary thyroid carcinoma (PTC) and follicular thyroid carcinoma (FTC) account for the great majority of all thyroid malignancies (1). An estimated 7% of the adult population (275,000 in 1999 in the United States alone) develops clinically significant thyroid nodules during their lifetime (2). The advent of thyroid ultrasound now allows for an increasing number of nodules to be diagnosed, and it is now recognized that nodules are present in an estimated 50% of the general population and are detected at a subclinical level. Because only 10% of these nodules will be a true malignancy, preoperative testing to differentiate benign from malignant nodules has been developed (3,4). Currently, fine needle aspiration (FNA) biopsy is the best diagnostic tool available for preoperative diagnosis. The FNA-based cytological diagnosis can be straightforward. However, approximately 20% (ranging from 9.2-42%) of all FNA will result in an inconclusive or suspicious outcome, especially if a follicular proliferation is found; the differentiation between a benign follicular neoplasia, especially follicular adenomas (FAs), and FTC based on the morphological features on FNA cytology is virtually impossible (5-8).

Therefore, because of the obvious difficulty in such preoperative diagnoses, surgical removal of the involved thyroid gland is routinely performed for diagnostic purposes in the setting of thyroid nodules and follicular cytology. However, in only 10-20% of these cases would a follicular thyroid malignancy be found on final histology, resulting in unnecessary surgery for the vast majority of patients (4-6, 8, 9). More importantly, false-negative cytologies can lead to delayed treatment with potentially serious consequences for the patient (10).

Regarding the obvious limitation of FNA cytology in the preoperative diagnosis, there is a clinical need for new, reliable preoperative markers to distinguish benign from malignant thyroid nodules. Nonetheless, whereas numerous assays have been developed in an attempt to reduce these inconclusive preoperative diagnoses, none has yet proven more successful than FNA cytology in the clinical setting (4, 11-13). A possible underlying cause for this clinical problem is the continued limited understanding of the biological relationship of the different benign thyroid neoplasias to each other and to thyroid carcinoma, despite much research in this field (11, 14-17).

Therefore, to directly address the clinically relevant issue, we sought to elucidate further the molecular differences between benign follicular neoplasia and FTC. We took a global expression array approach to dissect out the minimal number of genes that can play a fundamental role in the early steps of FTC carcinogenesis, thus, not only giving new biological insight, but also allowing us to differentiate FTC, even at the minimally invasive stage, from benign follicular neoplasia by evaluating expression of a limited set of genes. The use of objective molecular markers will serve as an adjunct in the preoperative diagnosis of follicular thyroid cancer.

SUMMARY OF THE INVENTION

In various embodiments, the invention provides methods for identifying malignant thyroid tissue and methods for differentiating between malignant and non-malignant neoplasms of thyroid tissue. According to the various embodiments, a thyroid tissue sample is tested for the expression of at least two genes chosen from CCND2, PCSK2, and PLAB, wherein the level of expression is determined by measuring the amount of mRNA corresponding to the gene of interest. FIGS. 5, 7, and 9, respectively, each show one embodiment of each the mRNA sequences of interest. In some embodiments, the thyroid tissue sample is tested for the expression of CCND2 and PCSK2. In other embodiments, the thyroid tissue sample is tested for the expression of CCND2 and PLAB. And in yet other embodiments, the thyroid tissue sample is tested for the expression of PCSK2 and PLAB. In some embodiments according to the invention, the thyroid tissue sample is tested for the expression of CCND2, PLAB, and PCSK2. In yet other embodiments, the expression of other genes such as those noted herein, may be used to assist in the identification of malignant tissue. A variety of methods and tools are known in the art for measuring levels of expression, including direct measurement of mRNA levels. The examples provided herein are not intended to be limiting, and other methods as described in the references noted herein and incorporated by reference may also be used in carrying out the invention.

In some embodiments, a determination of the presence of malignant thyroid tissue is obtained wherein the level of expression of two or more of the genes CCND2, PCSK2, and PLAB show changes as follows when compared with normal thyroid tissue or tissue having otherwise benign nodules: decreased expression of CCND2, decreased expression of PCSK2 and increased expression of PLAB. In other embodiments, variations in the levels of expression of at least two of the three genes are indicative of the presence of malignancy, according to the examples provided herein.

The invention also provides kits for identifying malignant thyroid tissue comprising means for assaying a thyroid tissue sample for the expression of at least two genes chosen from CCND2, PCSK2, and PLAB. In some embodiments, the kits comprise at least two of the following: (a) a container containing at least one CCND2 primer; (b) a container containing at least one PCSK2 primer; and (c) a container containing at least one PLAB primer.

Additional features and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings are incorporated in and constitute a part of this specification, and together with the description, serve to explain the principles of the invention.

BRIEF DESCRIPTION OF THE DRAWINGS

FIG. 5: CCND2 (cyclin D2) mRNA sequence (SEQ ID NO: 1). Other aliases for CCND2 include KIAK0002 and MGC102758.

FIG. 6: CCND2 (cyclin D2) amino acid sequence (SEQ ID NO: 2). Other aliases for CCND2 include KIAK0002 and MGC102758.

FIG. 7: PCSK2 (proprotein convertase subtilisin/kexin type 2) mRNA sequence (SEQ ID NO: 3). Other aliases for PCSK2 include NEC2 (neuroendocrine convertase 2), PC2 (prohormone convertase 2), and SPC2 (subtilisin-like prohormone convertase 2).

FIG. 8: PCSK2 (proprotein convertase subtilisin/kexin type 2) amino acid sequence (SEQ ID NO: 4). Other aliases for PCSK2 include NEC2 (neuroendocrine convertase 2), PC2 (prohormone convertase 2), and SPC2 (subtilisin-like prohormone convertase 2).

FIG. 9: PLAB mRNA sequence (SEQ ID NO: 5). Other aliases for PLAB include GDF-15 (growth differentiation factor 15), GDF15, MIC-1, MIC1, NAG-1, PDF (prostate differentiation factor), NSAID (non-steroidal anti-inflammatory drug)-activated protein, com1, and PTGFB (PTGF-beta).

FIG. 10: PLAB amino acid sequence (SEQ ID NO: 6). Other aliases for PLAB include GDF-15 (growth differentiation factor 15), GDF15, MIC-1, MIC1, NAG-1, PDF (prostate differentiation factor), NSAID (non-steroidal anti-inflammatory drug)-activated protein, com1, and PTGFB (PTGF-beta).

FIG. 11: hTERT (human telomerase reverse transcriptase) mRNA sequence of transcript variant #1 (SEQ ID NO: 7). Variant #1 represents the longest transcript. Other aliases for hTERT include TERT (telomerase reverse transcriptase), TP2, TRT (telomerase reverse transcriptase), EST2, TCS1 (telomerase catalytic subunit), and hEST2.

FIG. 12: hTERT (human telomerase reverse transcriptase) amino acid sequence of isoform 1 (SEQ ID NO: 8). Other aliases for hTERT include TERT (telomerase reverse transcriptase), TP2, TRT (telomerase reverse transcriptase), EST2, TCS1 (telomerase catalytic subunit), and hEST2.

FIG. 13: hTERT (human telomerase reverse transcriptase) mRNA sequence of transcript variant #2 (SEQ ID NO: 9). Variant #2, also called alpha, uses an in-frame alternate splice site in the coding region, compared to variant #1. Isoform 2 is shorter than isoform 1 and lacks part of reverse transcriptase (RT) motif 3. Isoform 2 is a dominant-negative inhibitor of telomerase activity. Other aliases for hTERT include TERT (telomerase reverse transcriptase), TP2, TRT (telomerase reverse transcriptase), EST2, TCS1 (telomerase catalytic subunit), and hEST2.

FIG. 14: hTERT (human telomerase reverse transcriptase) amino acid sequence of isoform 2 (SEQ ID NO: 10). Other aliases for hTERT include TERT (telomerase reverse transcriptase), TP2, TRT (telomerase reverse transcriptase), EST2, TCS1 (telomerase catalytic subunit), and hEST2.

FIG. 15: hTERT (human telomerase reverse transcriptase) mRNA sequence of transcript variant #3 (SEQ ID NO: 11). Variant #3 lacks two exons in its coding region, resulting in a frameshift and early termination compared to variant #1. Isoform 3 has a shorter and distinct C-terminus compared to isoform 1. Other aliases for hTERT include TERT (telomerase reverse transcriptase), TP2, TRT (telomerase reverse transcriptase), EST2, TCS1 (telomerase catalytic subunit), and hEST2.

FIG. 16: hTERT (human telomerase reverse transcriptase) amino acid sequence of isoform 3 (SEQ ID NO: 12). Other aliases for hTERT include TERT (telomerase reverse transcriptase), TP2, TRT (telomerase reverse transcriptase), EST2, TCS1 (telomerase catalytic subunit), and hEST2.

FIG. 17: hTERT (human telomerase reverse transcriptase) mRNA sequence of transcript variant #4 (SEQ ID NO: 13). Variant #4 has multiple differences in the coding region, resulting in a frameshift and early termination compared to variant #1. Isoform 4 has a shorter and distinct C-terminus, compared to variant #1. Other aliases for hTERT include TERT (telomerase reverse transcriptase), TP2, TRT (telomerase reverse transcriptase), EST2, TCS1 (telomerase catalytic subunit), and hEST2.

FIG. 18: hTERT (human telomerase reverse transcriptase) amino acid sequence of isoform 4 (SEQ ID NO: 14). Other aliases for hTERT include TERT (telomerase reverse transcriptase), TP2, TRT (telomerase reverse transcriptase), EST2, TCS1 (telomerase catalytic subunit), and hEST2.

FIG. 19: CD44 mRNA sequence of transcript variant #1 (SEQ ID NO: 15). Variant #1 represents the longest transcript. It encodes the longest isoform 1. Other aliases for CD44 include IN, LHR, MC56, MDU2, MDU3, MIC4, Pgp1, CDW44, MUTCH-I, ECMR-III, and MGC10468.

FIG. 20: CD44 amino acid sequence of isoform 1 (SEQ ID NO: 16). Other aliases for CD44 include IN, LHR, MC56, MDU2, MDU3, MIC4, Pgp1, CDW44, MUTCH-I, ECMR-III, and MGC10468.

FIG. 21: CD44 mRNA sequence of transcript variant #2 (SEQ ID NO: 17). Variant #2 lacks an in-frame coding exon compared to variant #1. The resulting isoform 2 lacks an internal region, as compared to isoform 1. Other aliases for CD44 include IN, LHR, MC56, MDU2, MDU3, MIC4, Pgp1, CDW44, MUTCH-I, ECMR-III, and MGC10468.

FIG. 22: CD44 amino acid sequence of isoform 2 (SEQ ID NO: 18). Other aliases for CD44 include IN, LHR, MC56, MDU2, MDU3, MIC4, Pgp1, CDW44, MUTCH-I, ECMR-III, and MGC10468.

FIG. 23: CD44 mRNA sequence of transcript variant #3 (SEQ ID NO: 19). Variant #3, also known as CD44R, lacks multiple coding-exons compared to variant #1. The translation remains in-frame. The resulting isoform 3 lacks an internal segment, as compared to isoform 1. Other aliases for CD44 include IN, LHR, MC56, MDU2, MDU3, MIC4, Pgp1, CDW44, MUTCH-I, ECMR-III, and MGC10468.

FIG. 24: CD44 amino acid sequence of isoform 3 (SEQ ID NO: 20). Other aliases for CD44 include IN, LHR, MC56, MDU2, MDU3, MIC4, Pgp1, CDW44, MUTCH-I, ECMR-III, and MGC10468.

FIG. 25: CD44 mRNA sequence of transcript variant #4 (SEQ ID NO: 21). Variant #4 lacks multiple coding-exons compared to variant #1. The translation remains in-frame. The resulting isoform 4 lacks an internal segment, as compared to isoform 1. Other aliases for CD44 include IN, LHR, MC56, MDU2, MDU3, MIC4, Pgp1, CDW44, MUTCH-I, ECMR-III, and MGC10468.

FIG. 26: CD44 amino acid sequence of isoform 4 (SEQ ID NO: 22). Other aliases for CD44 include IN, LHR, MC56, MDU2, MDU3, MIC4, Pgp1, CDW44, MUTCH-I, ECMR-III, and MGC10468.

FIG. 27: CD44 mRNA sequence of transcript variant #5 (SEQ ID NO: 23). Variant #5 lacks multiple coding-exons compared to variant #1. The translation frame is changed. The resulting isoform 5, also known as CD44 isoform RC, has a distinct and shorter C-terminus, as compared to isoform 1. Other aliases for CD44 include IN, LHR, MC56, MDU2, MDU3, MIC4, Pgp1, CDW44, MUTCH-I, ECMR-III, and MGC10468.

FIG. 28: CD44 amino acid sequence of isoform 5 (SEQ ID NO: 24). Other aliases for CD44 include IN, LHR, MC56, MDU2, MDU3, MIC4, Pgp1, CDW44, MUTCH-I, ECMR-III, and MGC10468.

FIG. 29: Frizzled-1 mRNA sequence (SEQ ID NO: 25). Other aliases for Frizzled-1 include FZD1, Wnt receptor, frizzled (Drosophila) homolog 1, frizzled 1, and frizzled, Drosophila, homolog of, 1.

FIG. 30: Frizzled-1 amino acid sequence (SEQ ID NO: 26). Other aliases for Frizzled-1 include FZD1, Wnt receptor, frizzled (Drosophila) homolog 1, frizzled 1, and frizzled, Drosophila, homolog of, 1.

FIG. 31: CITED1 mRNA sequence (SEQ ID NO: 27). Other aliases for CITED1 include MSG1.

FIG. 32: CITED1 amino acid sequence (SEQ ID NO: 28). Other aliases for CITED1 include MSG1.

FIG. 33: ARHI mRNA sequence (SEQ ID NO: 29). Other aliases for ARHI include DIRAS3 and NOEY2.

FIG. 34: ARHI amino acid sequence (SEQ ID NO: 30). Other aliases for ARHI include DIRAS3 and NOEY2.

FIG. 35: Primer sets for glyceraldehyde-3-phosphate dehydrogenase, β-actin, CCND2, PLAB, and PCSK2 (SEQ ID NOS 31-40, respectively, in order or appearance).

DESCRIPTION OF THE EMBODIMENTS

Figure 1:
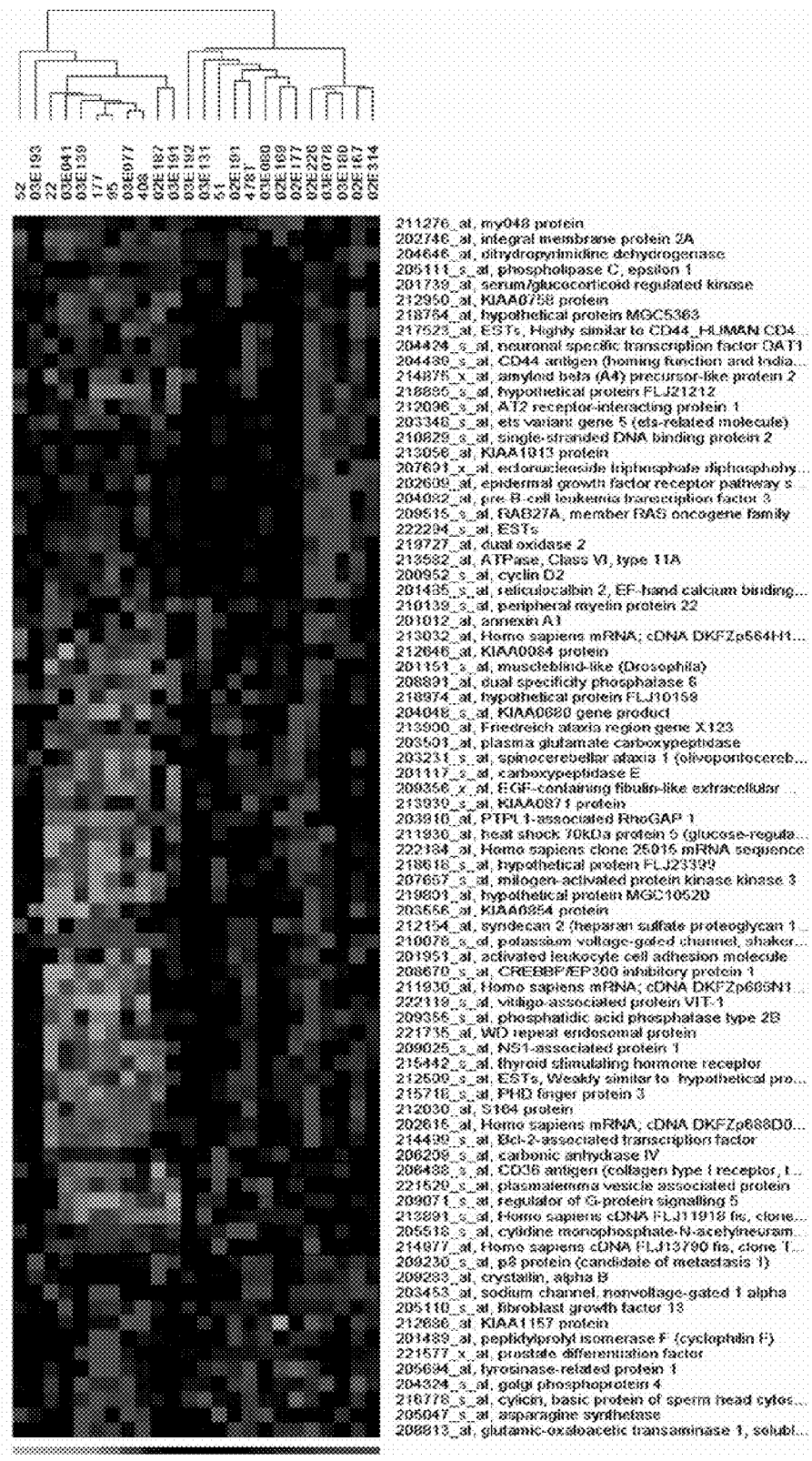
FIG. 1: Supervised hierarchical cluster analysis based on a set of 80 genes differentiates FTC from FA. Expression values of each gene across all samples were linearly scaled (standardized) to have a mean of 0 and SD of 1. These standardized values were used to calculate the correlation between genes, based on the distance metric (1-correlation). The average linkage model was used for merging nodes. Red represents overexpression and green represents underexpression.

The present invention may be understood more readily by reference to the following detailed description of the embodiments of the invention and the Examples included herein. However, before the present methods and compositions are disclosed and described, it is to be understood that this invention is not limited to specific methods, specific nucleic acids, specific polypeptides, specific cell types, specific host cells or specific conditions, etc., as such may, of course, vary, and the numerous modifications and variations therein will be apparent to those skilled in the art. It is also to be understood that the terminology used herein is for the purpose of describing specific embodiments only and is not intended to be limiting.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

As used herein, "cDNA" means a DNA prepared using messenger RNA (mRNA) as template. In contrast to genomic DNA and DNA polymerized from a genomic, non- or partially-processed RNA template, cDNA contains coding sequences of the corresponding protein in the absence of introns and other non-translated nucleic acids.

"Gene" refers broadly to any region or segment of DNA associated with a biological molecule or function. Thus, genes include coding sequence, and may further include regulatory regions or segments required for their expression. Genes may also include non-expressed DNA segments that, for example, form recognition sequences for other proteins. Genes can be obtained from a variety of sources, including cloning from a source of interest, or synthesizing from known or predicted sequence information, and may include sequences encoding desired parameters.

"Isolated," when used herein in the context of a nucleic acid or protein, denotes that the nucleic acid or protein is essentially free of other cellular components with which it is associated in the natural state. It is preferably in a homogeneous state although it can be in either dry form or an aqueous solution. Purity and homogeneity are typically determined using analytical chemistry techniques such as polyacrylamide gel electrophoresis or high performance liquid chromatography. A protein that is the predominant molecular species present in a preparation is substantially purified. An isolated gene is separated from open reading frames that flank the gene and encode a protein other than the gene of interest.

"Malignant" or "cancerous" or "cancer" refers to the properties of cells or tissue that distinguish them from benign or normal cells. Malignant, cancerous, and cancer cells invade, grow and destroy adjacent tissue, metastasize, and usually grow more rapidly than benign cells.

"Normal cell" means a non-cancerous or non-malignant cell.

"Nucleic acid" and "polynucleotide" refer to deoxyribonucleotides or ribonucleotides, nucleotides, oligonucleotides, polynucleotide polymers and fragments thereof in either single- or double-stranded form. A nucleic acid may be of natural or synthetic origin, double-stranded or single-stranded, and separate from or combined with carbohydrate, lipids, protein, other nucleic acids, or other materials, and may perform a particular activity such as transformation or form a useful composition such as a peptide nucleic acid (PNA). Unless specifically limited, the term encompasses nucleic acids containing known analogues of natural nucleotides that have similar binding properties as the reference nucleic acid and may be metabolized in a manner similar to naturally-occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19: 5081; Ohtsuka et al. (1985) J. Biol. Chem. 260: 2605-2608; Cassol et al. (1992); Rossolini et al. (1994) Mol. Cell. Probes 8: 91-98). The term nucleic acid is used interchangeably with gene, cDNA, and mRNA encoded by a gene.

"Sample" refers to an isolated sample of material, such as material obtained from an organism, containing nucleic acid molecules. A sample may comprise a bodily fluid; a cell; an extract from a cell, chromosome, organelle, or membrane isolated from a cell; genomic DNA, RNA, or cDNA in solution or bound to a substrate; or a biological tissue or biopsy thereof. A sample may generally be obtained from any bodily fluid (blood, urine, saliva, phlegm, gastric juices, etc.), cultured cells, biopsies, or other tissue preparations.

"Stringent hybridization conditions" and "stringent hybridization wash conditions" in the context of nucleic acid hybridization experiments such as Southern and northern hybridizations are sequence dependent, and are different under different environmental parameters. Nucleic acids having longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays," Elsevier, N.Y. Generally, highly stringent hybridization and wash conditions are selected to be 5° C. lower than the thermal melting point ($T_m$) for the specific sequence at a defined ionic strength and pH. Typically, under "stringent conditions" a probe will hybridize to its target subsequence, but to no other sequences. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids that have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., 10 to 50 nucleotides), stringent conditions typically involve salt concentrations of less than 1.0 M Na ion, typically 0.01 to 1.0 M Na ion concentration (or other salts) at pH 7.0 to 8.3, and the temperature is typically at least 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially similar if the polypeptides that they encode are substantially similar. This occurs, e.g., when a copy of a nucleic acid is created using the maximum codon degeneracy permitted by the genetic code.

Identification of Thyroid Carcinoma

Thyroid carcinoma is a common endocrine cancer with a favorable prognosis if subjected to timely treatment. However, the clinical identification of follicular thyroid carcinoma (FTC) among patients with benign thyroid nodules is still a challenge. Preoperative fine needle aspiration-based cytology cannot always differentiate follicular carcinoma as from benign follicular neoplasias. Because current methods fail to improve preoperative diagnosis of thyroid nodules, we explored new molecular-based diagnoses.

Briefly, we conducted a microarray-based study to reveal the genetic profiles unique to FTC and follicular adenomas (FAs), to identify the most parsimonious number of genes that could accurately differentiate between benign and malignant follicular thyroid neoplasia. We confirmed our data by quantitative RT-PCR and immunohistochemistry in two independent validation sets with a total of 114 samples. We were able to identify three genes, cyclin D2 (CCND2) (mRNA shown in FIG. 5), protein convertase 2 (PCSK2) (mRNA shown in FIG. 7), and prostate differentiation factor (PLAB) (mRNA shown in FIG. 9), that allow the accurate molecular classification of FTC and FA. Two independent validation sets revealed that the combination of these three genes could differentiate FTC from FA with a sensitivity of 100%, specificity of 94.7%, and accuracy of 96.7%. In addition, our model allowed the identification of follicular variants of papillary thyroid carcinoma with an accuracy of 85.7%. Three-gene profiling of thyroid nodules can accurately predict the diagnosis of FTC and FA with high sensitivity and specificity, thus identifying promising targets for further investigation to ultimately improve preoperative diagnosis.

The invention provides methods of identifying malignant thyroid tissue, and for differentiating between non-malignant and malignant neoplasms. According to the methods, in some embodiments a thyroid tissue sample is evaluated for the expression of at least two genes chosen from CCND2, PCSK2, and PLAB. Evaluation of expression of any two of the three can be combined in the test. Thus, in some embodiments, the thyroid tissue sample is tested for the expression of CCND2 and PCSK2, or alternatively for CCND2 and PLAB, or alternatively for PCSK2 and PLAB.

Of course, the assay can test for the presence of all three of the genes. Thus, in some embodiments, the thyroid tissue sample is tested for the expression of CCND2, PLAB, and PCSK2. Still further, the expression of additional genes may also be included, which may even further evidence the existence of malignant cells, or otherwise characterize a carcinoma. For example, in addition to testing for CCND2, PLAB, and PCSK2, one may also test for the expression of hTERT (mRNA sequences of hTERT variants are shown in FIGS. 11, 13, 15, and 17).

The invention also provides kits for identifying malignant thyroid tissue comprising means for assaying a thyroid tissue sample for the expression of at least two genes chosen from CCND2, PCSK2, and PLAB. In some embodiments, the kits comprise at least two of the following: (a) a container containing at least one CCND2 primer; (b) a container containing at least one PCSK2 primer; and (c) a container containing at least one PLAB primer. The kits may also include a container containing at least one hTERT primer. Kits according to the invention may also include additional molecular biology reagents for PCR reactions, including control primer sequences.

EXAMPLES

Materials and Methods

Tissue Specimens

In total, 55 samples (24 FTC and 31 benign thyroid samples) were independently acquired for gene expression analysis in our training and validation set mentioned below. All tissue specimens were snap frozen in liquid nitrogen after surgical removal and stored at $-80°$ C. Final histological classification for these samples was obtained from paraffin-embedded tissue. In addition, sections from each snap-frozen tumor sample were independently subjected to hematoxylin and eosin stain and evaluated by a pathologist. A panel (training set) of 12 FTCs and 12 FAs were accrued for microarray (GeneChip) analysis (Table 1).

TABLE 1

Histopathological classification of 12 FTC samples used for microarray analysis

| Sample ID | Sex/age | Pathologic diagnosis | TNM |
|---|---|---|---|
| 02E187 | n/a | FTC-Hurthle cell type; capsular Invasion | pT2 |
| 03E139 | F/61 | FTC-Hurthle cell type; widely Invasive | pT2 |
| 03E077 | F/48 | FTC-Hurthle cell type; minimal Invasive | pT2 |
| 03E193 | F/82 | FTC-Hurthle cell type; minimal Invasive | pT3 |
| 03E041 | F/72 | FTC-Hurthle cell type; hepatic Metastases | |
| 408 | F/71 | FTC-Hurthle cell type; recurrence | |
| 95 | F/69 | FTC; recurrence | |
| 22 | F/67 | FTC | pT4 |
| 177 | F/78 | FTC; widely invasive | pT3 |
| 52 | M/40 | FTC; recurrence | |
| 03E191 | F/62 | FTC; minimal invasive | pT2 |
| 03E192 | F/25 | FTC; minimal, angioinvasive | pT2 | n/a, Not available;
M, male;
F, female.

No atypical variant or Hurthle cell adenoma was included in our set of 12 FAs. RNA extraction of these 24 samples was performed for GeneChip analysis and quantitative RT-PCR. Furthermore, seven follicular variants of PTCs (FV-PTCs) and additional tissue samples from five normal thyroids have been obtained from unrelated patients and RNA was extracted for quantitative RT-PCR. To validate our findings from the training set, two independent validation sets were also obtained as follows. The first validation set comprised in total 31 samples among which were 12 FTCs, 12 nonfunctioning thyroid nodules (five FAs and seven adenomatous nodules), five autonomous adenomas (hot nodules), and two normal thyroid tissues. The first validation series was subjected to quantitative RT-PCR. The second independent validation set comprised paraffin-embedded archival material from 57 patients with FTC [including 14 minimally invasive FTC and seven minimally invasive Hurthle cell carcinomas (HCC)] and 26 patients with benign thyroid nodules (17FA and nine follicular hyperplasia) was subjected to immunohistochemistry (IHC). These samples were obtained through the Department of Pathology, The Ohio State University (Columbus, Ohio) and independently analyzed for histological diagnosis by the collaborating pathologist. All samples were obtained as anonymized materials without linked identifiers, with the approval of The Ohio State University's Institutional Review Board for Human Subjects' Protection.

RNA Extraction

Total RNA was isolated from 0.2 g of snap-frozen tissue using the TRizol Reagent (Invitrogen, Carlsbad, Calif.) and purified with the RNeasyKit (QIAGEN, Valencia, Calif.). Aliquots of 1 μg of total RNA were pretreated with DNase I (Invitrogen), after which 500 ng were reverse transcribed into cDNA using the SuperScript II System (Invitrogen) and a random hexamer anchored primer (Roche, Indianapolis, Ind.) according to the manufacturers' recommendations.

Oligonucleotide Expression Microarray Analysis

Sample preparation, hybridization, and analysis were performed as described previously, except that version U133A GeneChips were used, which contain 22283 probe sets (17). In addition RNA quality was assured by using the Bioanalyzer 2100 (Agilent, Palo Alto, Calif.) in accordance to the standards described by Auer et al. (18). Furthermore, a detailed description of the microarray experiment, according to the MIAME criteria, is available online at http://www.ebi.ac.uk/miamexpress/ (accession number E-MEXP-97). The cell intensity files (.CEL) were interrogated using the Affymetrix Microarray Suite 5.0 software. The percentage of probe-sets called present, the ratio of 3'-signal to 5'-signal of two housekeeping genes, the intensity of four hybridization controls, the scale factor between arrays and signal-to-background ratio were used for quality control assessment and to validate the in vitro transcription procedure. Furthermore, each array was cross-referenced to other arrays to identify array or single outliers by the method described by Li and Wong (19). All arrays passed these quality control steps. The DNA-Chip Analyzer Software (dChip) developed by Li and Wong (http://www.dchip.org) was used to normalize all arrays to a common array having a median overall brightness by using an invariant set of probes (19). A perfect match/mismatch difference model of the dChip software developed by Li and Wong was used to compute the model-based expression index (MBEI) (19). Raw data and computed expression values are available at http://www.ebi.ac.uk/miamexpress/. A summary table of the 80 differentially expressed genes is published as supplemental data on The Endocrine Society's Journals Online web site at http://jcem.endojournals.org (incorporated herein by reference, and referred to hereinafter as Supplemental FIG. 1).

Quantitative RT-PCR

Quantitative RT-PCR was performed using the primers noted below and the iQ SYBR Green RT-PCR system (Bio-Rad, Hercules, Calif.) on an iCycler Instrument (Bio-Rad) using the comparative threshold cycle (Ct) method (20). Equal efficiency of the reference and target amplification was determined by a validation experiment for all reference and target genes. Samples were analyzed in triplicate for the target gene and normalized to the average Ct value of the two reference genes, β-actin and glyceraldehyde-3-phosphate dehydrogenase (primers listed in FIG. 35), the latter two of which were analyzed as duplicate. ΔΔCt was determined by normalizing to the average ΔCt of five normal thyroid samples, indicating the relative difference in the expression level of the target gene between neoplasia and normal sample. The fold difference between FTC and FA is calculated by two to the power of the absolute difference in ΔΔCt between the two groups. All values are given as means and 95% confidence intervals of each group. Primer sequences were as follows: glyceraldehyde-3-phosphate dehydrogenase, 5'-GGGCTGCTTTTAACTCTGGTAA-3' (SEQ ID NO: 31) and 5'-ATGGGTGGAATCATATTGGAAC-3' (SEQ ID NO: 32); β-actin, 5'-CGTCATACTCCTGCTTGCTG-3' (SEQ ID NO: 33) and 5'-CCAGATCATTGCTCCTCCTGA-3' (SEQ ID NO: 34); cyclin D2 (CCND2), 5'-CACTTGTGATGC-CCTGACTG-3' (SEQ ID NO: 35) and 5'-ACGGTACTGCT-GCAGGCTAT-3' (SEQ ID NO: 36); prostate differentiation factor (PLAB), 5'-CAACCAGAGCTGGGAAGATT-3' (SEQ ID NO: 37) and 5'-AGAGATACGCAGGTGCAGGT (SEQ ID NO: 38); and protein convertase 2 (PCSK2), 5'-GC-CATGGTGAAAATGGCTAA-3' (SEQ ID NO: 39) and 5'-GAGTGTCAGCACCAACTTGC-3' (SEQ ID NO: 40) (FIG. 35). Primer sequence for ARHI and CITED1 have been described previously (21). One embodiment of the mRNA sequences for ARHI and CITED1 are shown in FIGS. 33 and 31 respectively.

Primers for quantitative RT-PCR were designed to span an exon-exon boundary or an intronic sequence, to avoid amplification of any genomic DNA. All quantitative RT-PCR products were initially visualized on a 2% agarose gel to ensure the presence of only a single amplicon product. The average sd between replicates was 0.15 and the average interassay sd for control genes was 0.32.

IHC

IHC was performed as described previously (22). Antibodies against CCND2 (Santa Cruz Biotechnology, Santa Cruz, Calif.) were used at a dilution 1:150 and against PCSK2A (US Biological, Swampscott, Mass.) were used at a dilution of 1:100. A total of 83 sections were analyzed, consisting of 57FTCs and 26 benign thyroid nodules (17FA and nine follicular hyperplasia). Additional sections from five normal thyroid glands and adjacent normal thyroid tissue were used for comparison. All slides were scored in a blinded fashion, and a second individual randomly validated the results. We regarded cells as immunoreactive when an obvious nuclear (CCND2) or cytoplasmic (PCSK2) expression was seen. We scored immunoreactivity as follows: retained (++) when more than 50% of nuclei/cytoplasm were strongly immunoreactive, reduced (+) when 10-50% of the nuclei/cytoplasm were immunoreactive, and absent (−) when less than 10% of the nuclei/cytoplasm were immunoreactive or all cells' nuclei showed no immunoreactivity at all [supplemental FIGS. 2 and 3 (published as supplemental data on The Endocrine Society's Journals Online web site at http://jcem.endojournals.org)]. The absence of a commercially available antibody that could reliable allow staining of thyroid tissue led to refine the IHC analysis to CCND2 and PCSK2.

Statistical Methods

Two-tailed Student's t test for independent samples, assuming equal variance, was used to determine difference between mean gene expression determined by RT-PCR of the three selected genes with 22 degrees of freedom (Table 2).

TABLE 2

Summary of quantitative RT-PCR data obtained for three genes, CCND2, PCSK2, and PLAB

| Gene | Affymetrix ID | NCBI public ID | ΔΔCt FTC[a]a | ΔΔCt FA[a]a | Fold change FTC vs .FA | P[b] |
|---|---|---|---|---|---|---|
| CCND2 | 200952_s_at | AW026491 | −4.03 (−5.19 to −2.87) | −0.68 (−1.18 to 0.18) | Down 10.2-fold | 0.00001 |
| PCSK2 | 204870_s_at | AL031664 | −7.46 (−9.17 to −5.75) | 0.58 (−1.79 to 2.95) | Down 263-fold | <0.00001 |
| PLAB | 221577_x_at | AF003934 | 4.12 (2.9 to 5.34) | 1.67 (0.53 to 2.81) | Up 5.5-fold | 0.0037 |

The approved gene symbol for PLAB by the Human Genome Organization Nomenclature Committee is GDF-15 (growth differentiation factor 15).
[a]Given are ΔΔCt as mean of each group and exact 95% confidence intervals in parentheses.
[b]P values are calculated with two-tailed Student's t-test for independent samples with 22 degrees of freedom.

The hierarchical cluster analysis we used to present our data are based on 96 probe sets that we filtered from the 22283 probe sets present on the HG-U133A chip by setting the thresholds to 2-fold expressional changes at the lower 90% confidence bound in either direction, a P value less than 0.05 for the difference in expression and no less than 50% present call for each gene in all 24 arrays. For our cluster analysis we choose the commonly used average linkage method. The distance measure in the clustering analysis is 1 minus the correlation coefficient (23).

When the expression of a single gene is used for diagnosis, it becomes necessary to find a desirable threshold value that is used to distinguish the two groups. We obtained for each possible threshold value the sensitivity and specificity of diagnoses, which are percentages of FTC ("test positive") and FA ("test negative", i.e., not FTC) samples correctly identified, respectively. The best threshold value is the one that maximizes an appropriate combination of the two. To use multiple genes in combination for the purpose of diagnosis, we applied linear discriminant analysis, which is based on the assumption of multivariate normal distributions of the joint expressions, and finds the best linear combination of the expression values that discriminates the two groups. In a first round, we applied the technique of cross-validation to the training set to assess the performances of the diagnostic tests, in which each sample is in turn left out of the data, a test developed based on the remaining samples and then applied to the sample being left out. The diagnoses can be compared with the true classes of the samples to indicate the performance of the method leading to the diagnostic test. In a second round, we applied the same technique of linear discriminant analysis, but this time using our validation set, to independently confirm our findings from the first round.

Results

To dissect out the most parsimonious gene expressional differences that accurately classify FTC from benign follicular neoplasias, in particular FAs, we used a global expression array approach on 12 FTCs and 12 FAs ("training set"). So that we could also differentiate the earliest signs of malignancy from benign neoplasia, we included two minimally invasive FTCs and two minimally invasive HCC within our set of FTCs (Table 1). Using the dChip compare sample function, we used, as a first step, a straight forward but conservative approach to identify those genes that could reliably differentiate between FTC and FA. Using these criteria defined in the Materials and Methods section, we identified 96 probe sets, which represent 80 genes. To statistically validate these finding, we performed a random permutation analysis, in which we randomly permuted the labels of FTCs and FAs a large number of times, repeated the gene selection procedure using the same criteria, and recorded the number of genes identified (24). It demonstrated that these 80 genes were uncovered due to biological relevance and not by random coincidence (i.e. chance). Hierarchical cluster analysis showed that based on this set of 80 genes, FTCs and FAs could be accurately classified according to their histological group (FIG. 1 and supplemental FIG. 1). Notably, three of four minimally invasive carcinomas and all HCC clustered within the FTC group. Only sample 03E192, a minimally invasive FTC, clustered with the FA group. From this set of 80 genes, we set out to find the smallest number of genes that could reliably classify FTC from FA in an independent validation set. After ranking the probe sets based on their fold change and significance (P value and t statistics), we identified those genes that also showed the highest difference in expression levels between minimally invasive FTCs and FA and we excluded expressed sequence tags and hypothetical proteins. Based on these criteria, we identified a list of 11 genes, and we focused, in the first instance, on the two highest ranking genes CCND2 (fold change −11.72; P value 0.0025), and PLAB (fold change 7.86; P value 0.0039; this gene has been annotated under different names, such as GDF-15, MIC-1, or com1) (25). Besides CCND2, we also found CD44 (MRNA sequences of CD44 variants are shown in FIGS. 19, 21, 23, 25, and 27), a gene targeted by the Wnt signaling pathway, markedly under-expressed in FTC (fold change −4.5; P value 0.0016). In addition, Frizzled-1 (one embodiment of Frizzled-1 mRNA is shown in FIG. 29), the membranous receptor for Wnt ligands, is also dysregulated (fold change −4.39; P value 0.0081). Neither CCND2 nor PLAB have been previously associated with thyroid carcinogenesis.

As a second step, we analyzed our gene expression data for probe sets with very high absent calls in only one group, either FTC or FA but not both, expecting that this approach will identify strongly under-expressed or silenced genes, which would in theory reliably differentiate these two histologies. Such high absent calls can lead to high P values, and consequently, the gene will not be detected by standard selection process. This approach revealed the gene encoding PCSK2 [present call 7% (MBEI 12.05) in FTC vs 0.75% (MBEI 1743.51) in FA; fold change 144.7, P value 0.011] on further analysis. Expressional differences of each of the three genes between FTC vs. FA in the training set was confirmed using quantitative RT-PCR (summarized in Table 2).

Genetic Classification of FTC and FA

Figure 2:
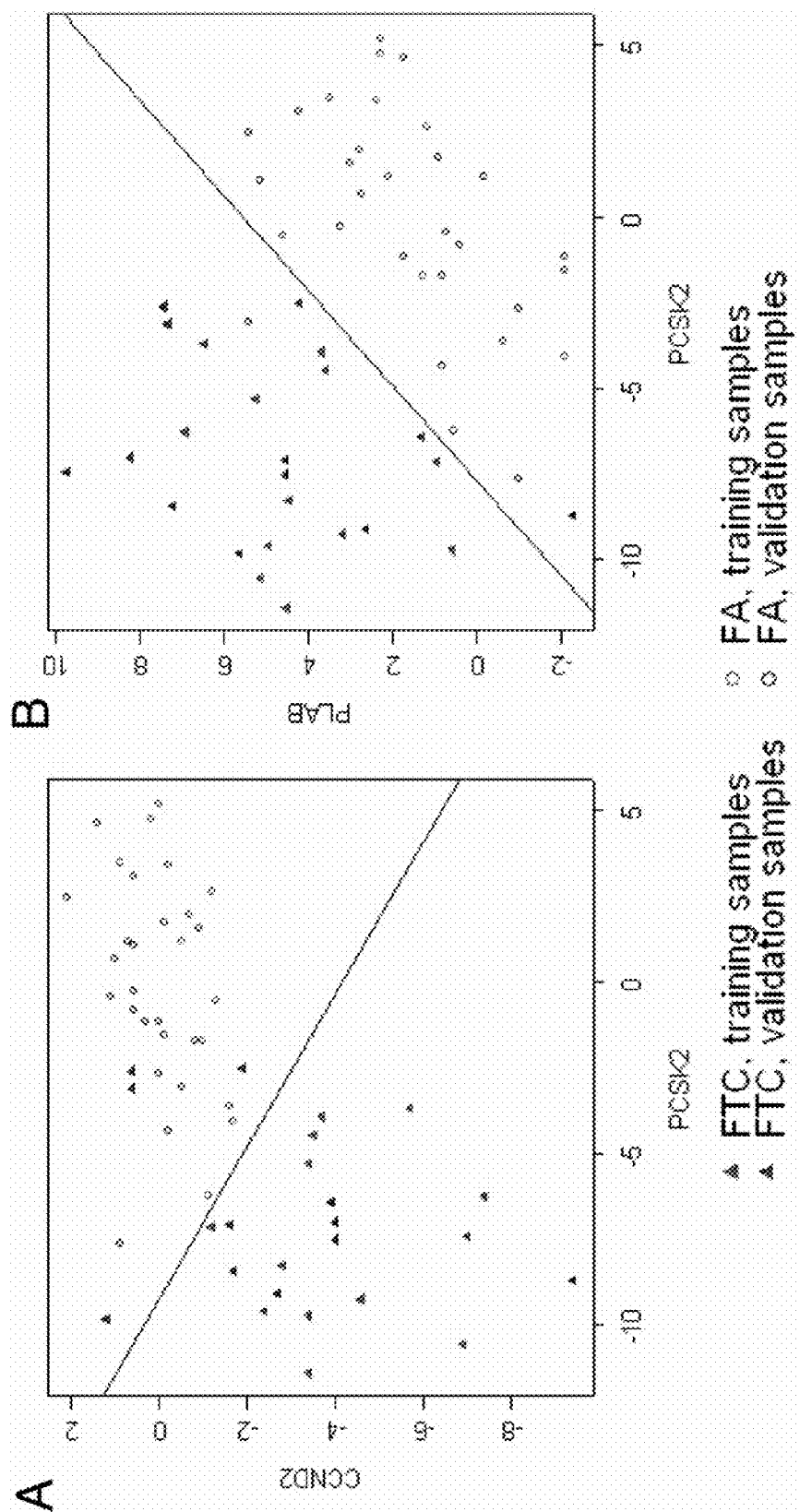
FIG. 2: Classification of 24 FTCs and 31 benign thyroid nodules (training set and validation set) by linear discriminant analysis. The two groups of samples (12 FTCs and 12 FAs) in the training set (red) can be distinguished perfectly based on the expression of CCND2 and PCSK2 (A). PCSK2 and PLAB have the same joint effect (B). The samples of the validation set (blue) can be classified with a sensitivity of 66.7% (exact 95% confidence interval, 34.9-90.1%) and specificity of 100% for the combination of CCND2 and PCSK2 (A). Using PLAB and PCSK2 combined, 91.7% (exact 95% confidence interval, 61.5-99.8%) of all FTCs in the validation set can be correctly identified and 94.7% (exact 95% confidence interval, 74.0-99.9%) of the benign thyroid nodules can be correctly classified as well (B). See also Table 3. The joint performance of all three genes is demonstrated in FIG. 3.

Based on our micro array data from the training set of 12 FTCs and 12 FAs, we then employed different statistical methods to predict the performance of our selected three genes in the accurate and reliable classification of FTC and FA. We employed receiver-operated characteristics (ROC) curve analysis to evaluate the performance of our genetic classification using the expression of each of the three genes (CCND2, PCSK2, and PLAB) individually. The ROC curves shows the sensitivity (proportion of FTC samples correctly classified) and one minus the specificity (where specificity is defined as proportion of FA samples correctly classified, i.e. not carcinoma) from using all possible threshold values of expression in the classification (graph not shown). Because a very low false-negative rate is desired, and we note that to perfectly identify all FTC samples (12 of 12), the minimum proportions of misclassified FA samples based on our data are 33% (four of 12), 16.7% (two of 12), and 75% (nine of 12) when the expression values of CCND2, PCSK2, and PLAB are used separately. Of significance, when expression values of CCND2 and PCSK2 were used jointly in the classification by applying the method of linear discriminant analysis, the two groups of samples, FTC and FA, can be distinguished perfectly (24 of 24) (FIG. 2A). PCSK2 and PLAB have the same joint effect (FIG. 2B). To validate this microarray-based classification, we blindly analyzed the expression levels of CCND2, PCSK2, and PLAB in an independent validation set of 12 FTCs, 12 nonfunctioning thyroid nodules (five FAs and seven follicular hyperplasia), two normal thyroids and five autonomous adenomas (hot nodules). Linear discriminant analysis of this in dependent validation series confirmed that dual combinations of CCND2 and PCSK2 or PCSK2 and PLAB were able to distinguish between FTCs and FAs with an accuracy of 87.1% (exact 95% confidence interval 70.2-96.4%) (27 of 31 samples) and 93.5% (exact 95% confidence interval 78.6-99.2%) (29 of 31 samples), respectively (FIG. 2 and Table 3). Furthermore, because both hot as well as cold nodules could be accurately identified, we showed that the differences between the two groups are in dependent from functional status of the thyroid nodule but due to malignant transformation. For an honest estimate of the clinical performance using all three genes together, i.e. CCND2, PCSK2, and PLAB jointly, we applied the classifier from linear discriminant analysis, which correctly identified all 12 FTC samples from the validation set, and we estimated a false-positive rate of 5.3% (exact 95% confidence interval 0.13-26.03%) (1 of 19 samples) allowing an accuracy of 96.7% (exact 95% confidence interval 83.3-99.9%) (30 of 31 samples) (FIG. 3 and Table 3).

TABLE 3

Figure 3:
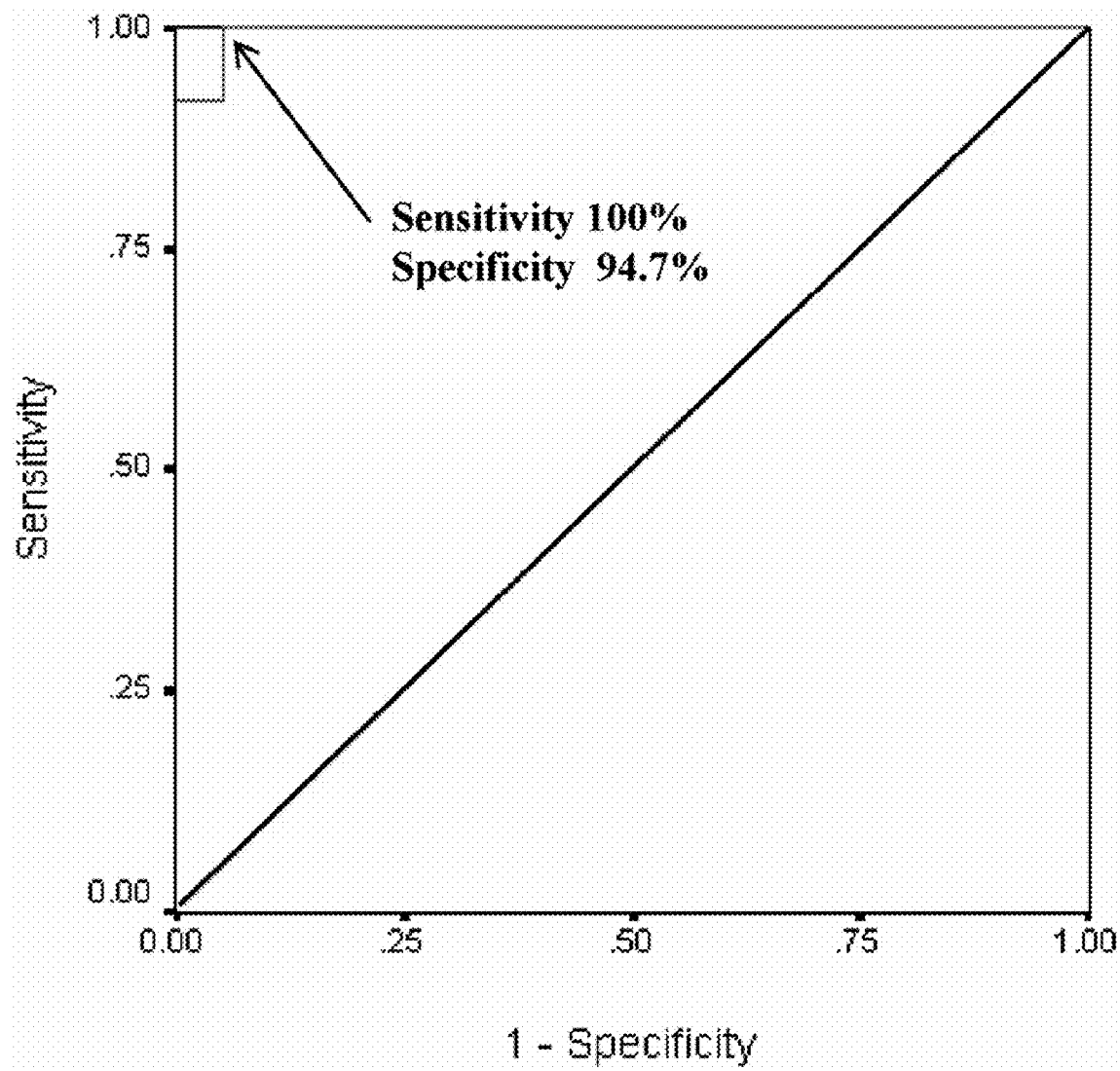
FIG. 3: ROC curve based on the joint performance of PCSK2, PLAB, and CCND2 in the classification of an independent validation set of 31 samples [12 FTCs, 12 nonfunctioning thyroid nodules (five FAs and seven adenomatous nodules), two normal tissue, and five autonomous adenomas] by linear discriminant analysis. The linear combination of gene expression levels of PCSK2, CCND2, and PLAB with the coefficients −0.2763, −0.1896, and 0.3666, respectively, is used for classification. The arrow indicates that when three genes are used together in this linear combination with a cutpoint of 2.0, a sensitivity of 100%, or 12 of 12, specificity of 94.7, or 18 of 19 (exact 95% confidence interval, 74.0-99.9%) and accuracy of 96.7, or 30 of 31 (exact 95% confidence interval, 83.3-99.9%) are reached. See also Table 3.

The performance of classifiers in terms of sensitivity and specificity in the validation set (see also FIGS. 2 and 3)

| Genes used in classification | Sensitivity in validation set | Specificity in validation set |
|---|---|---|
| PCSK2, CCND2 | 66.7% (8 of 12) | 100% (19 of 19) |
| PCSK2, PLAB | 91.7% (11 of 12) | 94.7% (18 of 19) |
| PCSK2, CCND2, PLAB | 100% (12 of 12) | 94.7% (18 of 19) |

Figure 4:
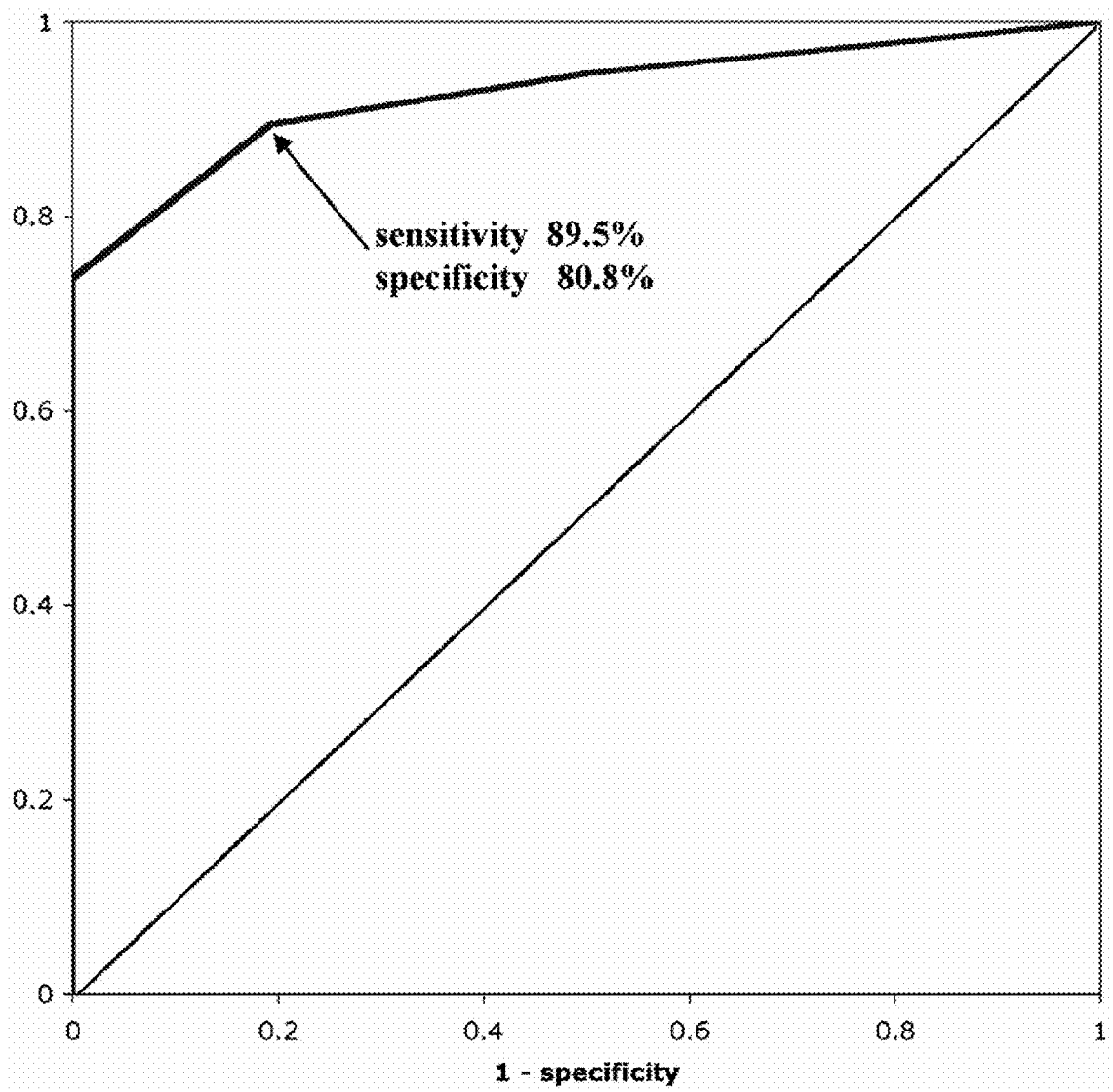
FIG. 4: ROC curve showing the performance of using antibodies against PCSK2 and CCND2 together in a second independent validation series of 83 samples. Each sample was assigned to one of five classes, according to the pattern of IHC-derived expression (Table 4). When categories 3, 4, and 5 are considered to represent test positive cases (FTC), the classification of follicular neoplasias based on the protein expression of CCND2 and PCSK2 shows a sensitivity of 89.5% (exact 95% confidence interval, 78.5-96.0%), a specificity of 80.8% (exact 95% confidence interval, 60.6-93.4%) and accuracy of 86.7% (exact 95% confidence interval, 77.5-93.2%; indicated by arrow in the curve), thus supporting the data derived from the more quantitative gene expression analysis (FIG. 3).

Furthermore, we validated our data by means of IHC for the most promising combination of two genes, CCND2 and PCSK2, in a second independent validation set of 57 FTCs and 26 benign thyroid nodules (supplemental FIGS. 2 and 3). Using PCSK2 and CCND2 jointly (ROC curve in FIG. 4), we observed a sensitivity of 89.5% (exact 95% confidence interval 78.5-96.0%), specificity of 80.8% (exact 95% confidence interval 60.6-93.4%) and accuracy of this test of 86.7% (exact 95% confidence interval 77.5-93.2%) when we chose the cutoff value for identifying FTC to be category 3 or larger (Table 4). Of note, complete absence of expression of PCSK2 and/or CCND2 was only seen in FTCs but never in benign thyroid nodules (Table 4). Furthermore, only 1 of 14 minimally invasive FTCs was misclassified due to retained immunostain for both antibodies, PCSK2 and CCND2. These observations affirm the accuracy of our genes to identify even minimally invasive neoplasias.

TABLE 4

Distribution of CCND2 and PCSK2 expression by immunohistochemistry[a] in 83 total follicular neoplasia samples

| | Category | | | | |
|---|---|---|---|---|---|
| | 1 (++/++) | 2 (++/+) | 3 (+/+) | 4 (−/+) | 5 (−/−) |
| Benign nodule | 13 (50%) | 8 (30.8%) | 5 (19.2%) | 0 | 0 |
| FTC | 3 (5.3%) | 3 (5.3%) | 9 (15.8%) | 06 (10.5%) | 36 (63.1%) |

[a]Images of samples are published as supplemental data on The Endocrine Society's Journals Online web site at http://jcem.endojournals.org.

Genetic Classification of FV-PTC

About 10% of suspicious FNA biopsies will be classified as FV-PTC in final histology. Therefore, we employed our three-gene based classifier system on a set of seven FV-PTC (Table 5). Six of seven FV-PTC samples analyzed were correctly identified as a malignant thyroid neoplasia (85.7%). In addition, we used CITED1 and ARHI, two other markers previously described by us, to further characterize these samples. It is of note that one sample (FV-PTC_269) does not show expression of CITED1, a predictive marker for FV-PTC and PTCs. Interestingly, only in this sample we see a clear underexpression of CCND2 as seen in all other FTCs analyzed. Furthermore, sample FV-PTC_345 shows expression of CITED1, but was not identified by our three-gene profile as a malignancy. It is note worthy that we found strong expression of the imprinted tumor suppressor gene ARHI in this sample. As we showed previously, silencing of this gene is associated with FTC carcinogenesis (21). These data might indicate that histological diagnosis of FV-PTC addresses a heterogeneous group of follicular neoplasia—an aspect that needs further elucidation. We note, by including the seven FV-PTC in our validation set, we can accurately identify 94.7% of all malignant samples (18 of 19) and 94.7% of all benign samples (18 of 19) as well.

TABLE 5

The performance of classifiers in a series of seven FV-PTCs

| Sample | ΔΔ Ct CCND2 | ΔΔ Ct PLAB | ΔΔ Ct PCSK2 | LDA value | Malignant | CITED1 | ARHI |
|---|---|---|---|---|---|---|---|
| FV-PTC_348 | −0.92 | 5.25 | −2.75 | 2.859 | True | + | + |
| FV-PTC_158 | −0.04 | 6.38 | −1.08 | 2.645 | True | + | − |
| FV-PTC_243 | −0.55 | 5.08 | −4.93 | 3.329 | True | + | − |

TABLE 5-continued

The performance of classifiers in a series of seven FV-PTCs

| Sample | ΔΔ Ct CCND2 | ΔΔ Ct PLAB | ΔΔ Ct PCSK2 | LDA value | Malignant | CITED1 | ARHI |
|---|---|---|---|---|---|---|---|
| FV-PTC__86 | −0.84 | 5.98 | −6.98 | 4.28 | True | + | − |
| FV-PTC__61 | 0.83 | 8.4 | −5.45 | 4.428 | True | + | − |
| FV-PTC__345 | −0.82 | 0.1 | −6.9 | 2.099 | False | + | + |
| FV-PTC__269 | −3.35 | 3.78 | −10.73 | 4.986 | True | − | − |

Values for the three-gene classifiers CCND2, PLAB, and PCSK2 are given in ΔΔCt (see also Table 2).
Six of seven FV-PTC (85.7%) have been correctly identified as malignant.
Sample FV-PTC__345 was not identified as malignant.
LDA value is the value of the linear combination of the three genes used to discriminate malignant and nonmalignant samples.
Expressions of the two genes CITED1 and ARHI are marked with +, where as no detectable expression is labeled −.

DISCUSSION

Currently, the diagnosis of thyroid nodules relies primarily on cytology (4, 8). For the majority of patients with PTC, non-FTC, or inflammatory lesions, FNA-based cytology can make a diagnosis with high accuracy (4). However, there is a significant proportion of follicular neoplasias in which this FNA-based preoperative cytologic diagnosis fails (4-6, 8-10). Several reports show that individual skill and experience largely affect the sensitivity of this diagnostic test, ranging from as low as 57% to as excellent as 98% (10). However, an estimated 20% (ranging from 9.2-42%) of all performed FNA-based cytologies will describe a suspicious follicular neoplasia, but only 10-20% of the patients that undergo surgery based on this diagnosis will actually have a malignant thyroid nodule (4, 5, 8). Based on investigative studies, immunohistochemical analysis has been proposed as a reliable marker for differentiating between FTC and FA (26). However, most of these markers showed their limitations in clinical practice and failed to become established (4, 27). One underlying reason might be that neoplasias do not show their distinct malignant phenotype and therefore cannot be diagnosed by these methods.

Different global gene expression studies have been conducted over the last years to identify novel targets. A recent study employing serial analysis of gene expression proposed a four-gene profile to improve preoperative diagnosis of FTC, but the accuracy of 80% for the gene expression based model is not superior to other algorithms (28). In addition other microarray-based studies, that allowed the highly accurate differentiation between FTC and FA by employing a 105-genes profile, still failed to identify minimally invasive FTCs, which comprise a large proportion of all FTCs (5,14). Our approach overcame this problem by including diverse phenotypes of follicular thyroid malignancies, especially minimally invasive variants, in the microarray-based training set. The inclusion of oncocytic variants of FTC (HCC) might appear distracting at first, because they are considered by some as a distinct clinicopathological entity and display unique molecular alterations (12, 29). Other groups have identified molecular alterations such as RET/PTC translocations or BRAF mutations in a subset of oncocytic thyroid cancer (29-31). Both these somatic alterations are common in PTC (15, 29). However, it is acknowledged that morphological features defining PTC and FV-PTC can be found in Huerthle cell carcinoma as well (29). Therefore, other reports endorse the idea of Huerthle cell PTC or FV of Huerthle cell PTC (29). Unsupervised cluster analysis and multidimensional scaling failed to differentiate FTC and HCC into two distinct classes, indicating that in our sample set, the similarities in gene expression out-weigh in FTC and HCC the differences. These findings and other reports support our hypothesis that FTC and some HCC may result from shared molecular alterations (21). Nonetheless, this area requires further clarification and it remains important to identify HCC separately.

Our approach has allowed us to identify genetic nuances in the initiation of follicular carcinogenesis. The dysregulation of CCND2, the first gene we identified as being an indictor of thyroid malignancies, and a cell cycle regulator, is intriguing because over-expression is associated with cancer progression and malignant transformation (32, 33). However, there are emerging data that CCND2 may act in different ways beyond cell cycle control. Other reports showed that CCND2 is under-expressed in various cancers due to hypermethylation of its promoter (34, 35). Our findings might provide further insight into the biological mechanism of CCND2 inactivation. Previous reports indicated that the dysregulation of the Wnt signaling pathway might play an important role in thyroid carcinogenesis (36). The membranous Frizzled receptors serve as binding targets for the Wnt proteins and subsequent activation of its intracellular Dishevelled proteins lead to transcription of targets genes such as CCND2 and CD44 (36, 37). Our data demonstrated dysregulation of this pathway from the receptor to the target genes in FTC. Corroborating our findings, a previous report identified 11 genes of the Wnt pathway, including CCND2 and CD44, under-expressed in prostate cancer (37). This seeming paradox that both over- and underexpression of the same gene can result in carcinogenesis is being explained by accumulating data showing that different signaling pathways and its downstream targets may act as oncogenes in some neoplasms and tumor suppressors in others (38, 39). Thus, further investigation would be required to determine how a profile of concurrent signaling pathways feed into directly opposed phenotypes.

The second gene we identified, PLAB, encodes a member of the TGF-β superfamily that is known to prevent apoptosis by activating the Akt pathway (25). The importance of Akt activation in follicular thyroid carcinogenesis has been previously shown by us (40). Therefore, PLAB might provide an upstream target of this pathway. Furthermore, an estimated 10% of all FNA do not result in sufficient material for a cytological diagnosis (4). Due to the lack of serum biomarkers that could identify FTCs, no preoperative noninvasive diagnosis is currently available for these patients. In this context, PLAB, a secreted protein, should be considered for further investigation to determine its feasibility as a diagnostic tool to identify thyroid malignancies from a simple blood test (41).

The third gene identified in our analysis is PCSK2. The members of this family process latent precursor proteins into their biologically active products. The mechanism by which the disruption of proprotein processing can promote tumorigenesis in thyroid tissue remains unknown. However, it has been shown that the inhibition of proprotein convertases enhances cell migration and metastases development of human colon carcinoma cells (42). Such a mechanism is plausible as well in thyroid carcinogenesis.

Even when we used only a combination of two of the three identified genes (CCND2 and PCSK2 or PLAB and PCSK2) we were still able to correctly classify 100% of the FTCs, including four minimally invasive ones, and all FAs. Indeed, using an independent validation series of 31 samples, we demonstrated that the combination of all three genes CCND2, PCSK2, and PLAB performed well in differentiating FTC from FA, resulting in an accuracy of 96.7% (exact 95% confidence interval of 83.3-99.9%). Furthermore, we were able to use a second validation series and a different technique, IHC, to examine a combination of only CCND2 and PCSK2, which resulted in an accuracy of 86.7%. Thus, our results appear to be superior to those reported using RT-PCR methods to detect gene expression of telomerase, galectin-3, or a number of other markers to discriminate benign from malignant follicular thyroid tumors (4, 13, 43, 44). The employment of galectin-3 IHC has been reported to reliably identify malignant thyroid lesions (26, 45). However, we and others have shown previously that this method does not succeed in improving the differentiation between FTCs and FAs in all cases (27, 43). Furthermore, analysis by means of IHC often has its limitations, not only due to variability of antibodies or Interinstitutional variation (artifact) but also because of nonuniform classification and interpretation. In contrast, the gene expression analysis described here, in a total of 24 FTCs and 31 benign thyroid nodules, using the combination of three genes, resulted in 100% of FTCs being identified and 30 of 31 of benign thyroid nodules definitively identified as well. A very recent FNA-based study employing hTERT as a molecular differentiator succeeded with recognizable sensitivity and specificity (46). However, the data indicate that this test performs much better in the identification of PTC and FV-PTC compared with FTC. Indeed, a full 20% of FTCs were missed. In addition, the performance of this test in identifying minimally invasive FTCs is unclear, and the authors conclude that additional molecular-based markers need to be explored (46). The robust results from our initial testing/training set confirmed by two independent validation sets have lent confidence that the invention as disclosed in its various embodiments herein might help to establish a new and reliable molecular adjunct for diagnosis of follicular thyroid nodules in the near future.

There exist other studies that reported accurate differentiation of thyroid carcinomas, but notably, all these models were either based on high-density gene profiles (100 or more genes), which would not work in a presurgical diagnostic setting due to limited tissue and RNA available in such a setting, or do not provide the accuracy needed (13, 14, 28, 47). Our classification model based on the limited number of genes, only three, provides the basis to pursue further evaluation. Whereas the technique to perform gene expression analysis in limited cell material has been well established (48), it needs to be shown how in adequate and/or contaminated FNA will affect the accuracy of the methods of the instant invention.

FV-PTC will be found in about 10% (range 0-22%) of inconclusive FNA cytologies (5, 6, 49, 50) and it is of note that when we employed our three-gene profile, we were able to identify FV-PTCs with an accuracy of 85.7%. Still, we need to acknowledge that FV-PTC might pose a special challenge when employing the three-gene predictor model into an FNA based setting. Our data indicate that the histological diagnosis of FV-PTC might describe a heterogeneous group of thyroid neoplasias. In this regard, it is of note that in a recent study by Lloyd et al. a concordant diagnosis of FV-PTC among 10 pathologists was made only in 39% of all cases (51). This high degree of observer variation can lead to a considerable bias of data if analysis is based on the unreviewed diagnosis of FV-PTC.

However, considering the recent studies that reported the differentiation between FV-PTC and FA using hTERT or CITED1, it may be plausible to use a four-gene test comprising CCND2, PCSK2, and PLAB plus hTERT (46, 52). Therefore, there is accumulating molecular evidence that suggest that, in the near future, the majority of, if not all, thyroid malignancies can be targeted for definitive surgery, abolishing the requirement of a completion surgery (46, 53, 54). More importantly, most of the FAs that currently would have gone to unnecessary surgery would have been spared an extensive operation.

In summary, we have demonstrated that genetic classification of follicular thyroid neoplasia with a minimal number of three genes is highly accurate and may provide a tool to overcome the difficulties in today's preoperative diagnosis of follicular malignancies. It is hoped that the quantitative nature of such a test will be a useful gene-based objective adjunct to the preoperative diagnosis of a disease that currently relies solely on cytology.

CITATIONS

1. Kinder B K 2003 Well-differentiated thyroid cancer. Curr Opin Oncol 15:71-77.
2. Welker M J, Orlov D 2003 Thyroid nodules. Am Fam Physician 67:559-566.
3. Ross D S 2002 Nonpalpable thyroid nodules—managing an epidemic. J Clin Endocrinol Metab 87:1938-1940.
4. Segev D L, Clark D P, Zeiger M A, Umbricht C 2003 Beyond the suspicious thyroid fine needle aspirate. A review. Acta Cytol 47:709-722.
5. Yang G C, Liebeskind D, Messina A V 2003 Should cytopathologists stop reporting follicular neoplasms on fine-needle aspiration of the thyroid? Cancer 99:69-74.
6. Sclabas G M, Staerkel G A, Shapiro S E, Formage B D, Sherman S I, Vassillo-poulou-Sellin R, Lee J E, Evans D B 2003 Fine-needle aspiration of the thyroid and correlation with histopathology in a contemporary series of 240 patients. Am J Surg 186:702-709; discussion, 709-710.
7. Chow L S, Gharib H, Goellner J R, van Heerden J A 2001 Nondiagnostic thyroid fine-needle aspiration cytology: management dilemmas. Thyroid 11:1147-1151.
8. Sherman S I 2003 Thyroid carcinoma. Lancet 361:501-511.
9. Raber W, Kaserer K, Niederle B, Vierhapper H 2000 Risk factors for malignancy of thyroid nodules initially identified as follicular neoplasia by fine-needle aspiration: results of a prospective study of one hundred twenty patients. Thyroid 10:709-712.
10. Yeh M W, Demircan O, Ituarte P, Clark O H 2004 False-negative fine-needle aspiration cytology results delay treatment and adversely affect outcome in patients with thyroid carcinoma. Thyroid 14:207-215.

11. Fagin J A 2002 Perspective: lessons learned from molecular genetic studies of thyroid cancer-insights into pathogenesis and tumor-specific therapeutic targets. Endocrinology 143:2025-2028.
12. Hoos A, Stojadinovic A, Singh B, Dudas M E, Leung D H, Shaha A R, Shah J P, Brennan M F, Cordon-Cardo C, Ghossein R 2002 Clinical significance of molecular expression profiles of Hurthle cell tumors of the thyroid gland analyzed via tissue microarrays. Am J Pathol 160:175-183.
13. Takano T, Miyauchi A, Yoshida H, Kuma K, Amino N 2004 High-through put differential screening of mRNAs by serial analysis of gene expression: decreased expression of trefoil factor 3 mRNA in thyroid follicular carcinomas. Br J Cancer 90:1600-1605.
14. Barden C B, Shister K W, Zhu B, Guiter G, Greenblatt D Y, Zeiger M A, Fahey 3rd T J 2003 Classification of follicular thyroid tumors by molecular signature: results of gene profiling. Clin Cancer Res 9:1792-1800.
15. Segev D L, Umbricht C, Zeiger M A 2003 Molecular pathogenesis of thyroid cancer. Surg Oncol 12:69-90.
16. Huang Y, Prasad M, Lemon W J, Hampel H, Wright F A, Kornacker K, LiVolsi V, Frankel W, Kloos R T, Eng C, Pellegata N S, de la Chapelle A 2001 Gene expression in papillary thyroid carcinoma reveals highly consistent profiles. Proc Natl Acad Sci USA 98:15044-15049.
17. Aldred M A, Morrison C, Gimm O, Hoang-Vu C, Krause U, Dralle H, Jhiang S, Eng C 2003 Peroxisome proliferator-activated receptor y is frequently down-regulated in a diversity of sporadic nonmedullary thyroid carcinomas. Oncogene 22:3412-3416.
18. Auer H, Lyianarachchi S, Newsom D, Klisovic M I, Marcucci G, Kornacker K, Marcucci U 2003 Chipping away at the chip bias: RNA degradation in microarray analysis. Nat Genet 35:292-293.
19. Li C, Wong W H 2001 Model-based analysis of Oligonucleotide arrays: expression index computation and outlier detection. Proc Natl Acad Sci USA 98:31-36.
20. Sledz C A, Holko M, de Veer M J, Silverman R H, Williams B R 2003 Activation of the interferon system by short-interfering RNAs. Nat Cell Biol 5:834-839.
21. Weber F, Aldred M A, Morrison C D, Plass C, Frilling A, Broelsch C E, Waite K A, Eng C 2005 Silencing of the maternally imprinted tumor suppressor ARHI contributes to follicular thyroid carcinogenesis. J Clin Endocrinol Metab 90:1149-1155.
22. Aldred M A, Ginn-Pease M E, Morrison C D, Popkie A P, Gimm O, Hoang-Vu C, Krause U, Dralle H, Jhiang S M, Plass C, Eng C 2003 Caveolin-1 and caveolin-2, together with three bone morphogenetic protein-related genes, may encode novel tumor suppressors down-regulated in sporadic follicular thyroid carcinogenesis. Cancer Res 63:2864-2871.
23. Hakak Y, Walker J R, Li C, Wong W H, Davis K L, Buxbaum J D, Haroutunian V, Fienberg, A A 2001 Genome-wide expression analysis reveals dysregulation of myelination-related genes in chronic schizophrenia. Proc Natl Acad Sci USA 98:4746-4751.
24. Tusher V G, Tibshirani R, Chu G 2001 Significance analysis of microarrays applied to the ionizing radiation response. Proc Natl Acad Sci USA 98:5116-5121.
25. Subramaniam S, Strelau J, Unsicker K 2003 Growth differentiation factor-15 prevents low potassium-induced cell death of cerebellar granule neurons by differential regulation of Akt and ERK pathways. J Biol Chem 278: 8904-8912.
26. Bartolazzi A, Gasbarri A, Papotti M, Bussolati G, Lucante T, Khan A, Inohara H, Marandino F, Orlandi F, Nardi F, Vecchione A, Tecce R, Larsson O 2001 Application of an immunodiagnostic method for improving preoperative diagnosis of nodular thyroid lesions. Lancet 357:1644-1650.
27. Niedziela M, Maceluch J, Korman E 2002 Galectin-3 is not an universal marker of malignancy in thyroid nodular disease in children and adolescents. J Clin Endocrinol Metab 87:4411-4415.
28. Cerutti J M, Delcelo R, Amadei M J, Nakabashi C, Maciel R M, Peterson B, Shoemaker J, Riggins G J 2004 A preoperative diagnostic test that distinguishes benign from malignant thyroid carcinoma based on gene expression. J Clin Invest 113:1234-1242.
29. Asa S L 2004 My approach to oncocytic tumours of the thyroid. J Clin Pathol 57:225-232.
30. Musholt P B, Imkamp F, von Wasielewski R, Schmid K W, Musholt T J 2003 RET rearrangements in archival oxyphilic thyroid tumors: new insights in tumorigenesis and classification of Hurthle cell carcinomas? Surgery 134:881-889; discussion 889.
31. Chiappetta G, Toti P, Cetta F, Giuliano A, Pentimalli F, Amendola I, Lazzi S, Monaco M, Mazzucchelli L, Tosi P, Santoro M, Fusco A 2002 The RET/PTC oncogene is frequently activated in oncocytic thyroid tumors (Hurthle cell adenomas and carcinomas), but not in oncocytic hyperplastic lesions. J Clin Endocrinol Metab 87:364-369.
32. Takano Y, Kato Y, van Diest P J, Masuda M, Mitomi H, Okayasu 1 2000 Cyclin D2 overexpression and lack of p27 correlate positively and cyclin E inversely with a poor prognosis in gastric cancer cases. Am J Pathol 156:585-594.
33. Takano Y, Kato Y, Masuda M, Ohshima Y, Okayasu 1 1999 Cyclin D2, but not cyclin D1, overexpression closely correlates with gastric cancer progression and prognosis. J Pathol 189:194-200.
34. Yu J, Leung W K, Ebert M P, Leong R W, Tse P C, Chan M W, Bai A H, To K F, Malfertheiner P, Sung J J 2003 Absence of cyclin D2 expression is associated with promoter hypermethylation in gastric cancer. Br J Cancer 88:1560-1565.
35. Padar A, Sathyanarayana U G, Suzuki M, Maruyama R, Hsieh J T, Frenkel E P, Minna J D, Gazdar A F 2003 Inactivation of cyclin D2 gene in prostate cancers by aberrant promoter methylation. Clin Cancer Res 9:4730-4734.
36. Helmbrecht K, Kispert A, von Wasielewski R, Brabant G 2001 Identification of a Wnt/β-catenin signaling pathway in human thyroid cells. Endocrinology 142:5261-5266.
37. Wissmann C, Wild P J, Kaiser S, Roepcke S, Stoehr R, Woenckhaus M, Kristiansen G, Hsieh J C, Hofstaedter F, Hartmann A, Knuechel R, Rosenthal A, Pilarsky C 2003 WIF1, a component of the Wnt pathway, is down-regulated in prostate, breast, lung, and bladder cancer. J Pathol 201:204-212.
38. Fan X, Mikolaenko I, Elhassan I, Ni X, Wang Y, Ball D, Brat D J, Perry A, Eberhart C G 2004 Notch1 and notch2 have opposite effects on embryonal brain tumor growth. Cancer Res 64:7787-7793.
39. Miller L D, Park K S, Guo Q M, Alkharouf N W, Malek R L, Lee N H, Liu E T, Cheng S Y 2001 Silencing of Wnt signaling and activation of multiple metabolic pathways in response to thyroid hormone-stimulated cell proliferation. Mol Cell Biol 21:6626-6639.
40. Vasko V, Saji M, Hardy E, Kruhlak M, Larin A, Savchenko V, Miyakawa M, Isozaki O, Murakami H, Tsushima T, Burman K D, De Micco C, Ringel M D 2004.

Akt activation and localization correlate with tumour invasion and oncogene expression in thyroid cancer. J Med Genet 41:161-170.
41. Brown D A, Ward R L, Buckhaults P, Liu T, Romans K E, Hawkins N J, Bauskin A R, Kinzler K W, Vogelstein B, Breit S N 2003 MIC-1 serum level and genotype: associations with progress and prognosis of colorectal carcinoma. Clin Cancer Res 9:2642-2650.
42. Nejjari M, Berthet V, Rigot V, Laforest S, Jacquier M F, Seidah N G, Remy L, Bruyneel E, Scoazec J Y, Marvaldi J, Luis J 2004 Inhibition of proprotein convertases enhances cell migration and metastases development of human colon carcinoma cells in a rat model. Am J Pathol 164:1925-1933.
43. Feilchenfeldt J, Totsch M, Sheu S Y, Robert J, Spiliopoulos A, Frilling A, Schmid K W, Meier C A 2003 Expression of galectin-3 in normal and malignant thyroid tissue by quantitative PCR and immunohistochemistry. Mod Pathol 16:1117-1123.
44. Saji M, Xydas S, Westra W H, Liang C K, Clark D P, Udelsman R, Umbricht C B, Sukumar S, Zeiger M A 1999 Human telomerase reverse transcriptase (hTERT) gene expression in thyroid neoplasms. Clin Cancer Res 5:1483-1489.
45. Saggiorato E, Cappia S, De Giuli P, Mussa A, Pancani G, Caraci P, Angeli A, Orlandi F 2001 Galectin-3 as a presurgical immunocytodiagnostic marker of minimally invasive follicular thyroid carcinoma. J Clin Endocrinol Metab 86:5152-5158.
46. Umbricht C B, Conrad G T, Clark D P, Westra W H, Smith D C, Zahurak M, Saji M, Smallridge R C, Goodman S, Zeiger M A 2004 Human telomerase reverse transcriptase gene expression and the surgical management of suspicious thyroid tumors. Clin Cancer Res 10:5762-5768.
47. Finley D J, Zhu B, Barden C B, Fahey 3rd T J 2004 Discrimination of benign and malignant thyroid nodules by molecular profiling. Ann Surg 240:425-436; discussion 436-7.
48. Giannini R, Faviana P, Cavinato T, Elisei R, Pacini F, Berti P, Fontanini G, Ugolini C, Camacci T, De Ieso K, Miccoli P, Pinchera A, Basolo F 2003 Galectin-3 and oncofetal-fibronectin expression in thyroid neoplasia as assessed by reverse transcription-polymerase chain reaction and immunochemistry in cytologic and pathologic specimens. Thyroid 13:765-770.
49. Kesmodel S B, Terhune K P, Canter R J, Mandel S J, LiVolsi V A, Baloch Z W, Fraker D L 2003 The diagnostic dilemma of follicular variant of papillary thyroid carcinoma. Surgery 134:1005-1012; discussion, 1012.
50. Bakshi N A, Mansoor I, Jones B A 2003 Analysis of inconclusive fine-needle aspiration of thyroid follicular lesions. Endocr Pathol 14:167-175.
51. Lloyd R V, Erickson L A, Casey M B, Lam K Y, Lohse C M, Asa S L, Chan J K, DeLellis R A, Harach H R, Kakudo K, LiVolsi V A, Rosai J, Sebo T J, Sobrinho-Simoes M, Wenig B M, Lae M E 2004 Observer variation in the diagnosis of follicular variant of papillary thyroid carcinoma. Am J Surg Pathol 28:1336-1340.
52. Aldred M A, Huang Y, Liyanarachchi S, Pellegata N S, Gimm O, Jhiang S, Davuluri R V, de la Chapelle A, Eng C 2004 Papillary and follicular thyroid carcinomas show distinctly different microarray expression profiles and can be distinguished by a minimum of five genes. J Clin Oncol 22:3531-3539.
53. Finley D J, Arora N, Zhu B, Gallagher L, Fahey 3rd T J 2004 Molecular profiling distinguishes papillary carcinoma from benign thyroid nodules. J Clin Endocrinol Metab 89:3214-3223.
54. Mazzanti C, Zeiger M A, Costourous N, Umbricht C, Westra W H, Smith D, Somervell H, Bevilacqua G, Alexander H R, Libutti S K 2004 Using gene expression profiling to differentiate benign versus malignant thyroid tumors. Cancer Res 64:2898-2903.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of differentially diagnosing non-malignant thyroid tissue from malignant thyroid tissue comprising testing a thyroid tissue sample for the expression of at least two genes chosen from CCND2, PCSK2, and PLAB, wherein a decreased level of expression of CCND2 as compared to a control, a decreased level of expression of PCSK2 as compared to a control, or an increased level of expression of PLAB as compared to a control indicates the presence of malignant thyroid tissue in the sample.

2. The method according to claim 1, wherein the thyroid tissue sample is tested for the expression of CCND2 and PCSK2.

3. The method according to claim 1, wherein the thyroid tissue sample is tested for the expression of CCND2 and PLAB.

4. The method according to claim 1, wherein the thyroid tissue sample is tested for the expression of PCSK2 and PLAB.

5. The method according to claim 1, wherein the thyroid tissue sample is tested for the expression of CCND2, PLAB, and PCSK2.

6. The method according to claim 1, further comprising testing a thyroid tissue sample for the expression of at least one gene chosen from hTERT, CD44, CITED1, ARHI, and Frizzled-1, wherein an increased level of expression of hTERT as compared to a control, a decreased level of expression of CD44 as compared to a control, an increased level of expression of CITED1 as compared to a control, a decreased level of expression of ARHI as compared to a control, or a decreased level of expression of Frizzled-1 as compared to a control indicates the presence of malignant thyroid tissue in the sample.

7. A kit for identifying malignant thyroid tissue comprising means for assaying a thyroid tissue sample for the expression of at least two genes chosen from CCND2, PCSK2, and PLAB, and at least two of the following:
   (a) at least one CCND2 primer, wherein the at least one CCND2 primer is chosen from 5'-CACTTGTGATGC-CCTGACTG-3' (SEQ ID NO: 35) and 5'-ACGGTACT-GCTGCAGGCTAT-3' (SEQ ID NO: 36);
   (b) at least one PCSK2 primer, wherein the at least one PCSK2 primer is chosen from 5'-GCCATGGT-GAAAATGGCTAA-3' (SEQ ID NO: 39) and 5'-GAGT-GTCAGCACCAACTTGC-3' (SEQ ID NO: 40) and
   (c) at least one PLAB primer, wherein the at least one PLAB primer is chosen from 5'-CAACCAGAGCTGG-GAAGATT (SEQ ID NO: 37) and 5'-AGAGATACG-CAGGTGCAGGT-3' (SEQ ID NO: 38).

8. The kit according to claim 7, wherein the kit further comprises a means for assaying a thyroid tissue sample for the expression of at least one gene chosen from hTERT, CD44, CITED1, ARHI, and Frizzled-1.

* * * * *